(12) United States Patent
Dudasik

(10) Patent No.: US 10,245,154 B2
(45) Date of Patent: Apr. 2, 2019

(54) INSTRUMENTS AND METHODS FOR INSERTING ARTIFICIAL INTERVERTEBRAL IMPLANTS

(71) Applicant: SpineCore, Inc., Allendale, NJ (US)

(72) Inventor: Michael W. Dudasik, Nutley, NJ (US)

(73) Assignee: SpineCore, Inc., Allendale, NJ (US)

( * ) Notice: Subject to any disclaimer, the term of this patent is extended or adjusted under 35 U.S.C. 154(b) by 150 days.

(21) Appl. No.: 15/364,848

(22) Filed: Nov. 30, 2016

(65) Prior Publication Data
US 2017/0079808 A1 Mar. 23, 2017

Related U.S. Application Data

(60) Continuation of application No. 14/051,086, filed on Oct. 10, 2013, now Pat. No. 9,539,114, which is a
(Continued)

(51) Int. Cl.
*A61F 2/46* (2006.01)
*A61F 2/00* (2006.01)
(Continued)

(52) U.S. Cl.
CPC ........ *A61F 2/4425* (2013.01); *A61B 17/1757* (2013.01); *A61F 2/4611* (2013.01); *A61F 2/4657* (2013.01); *A61F 2/4684* (2013.01); *A61B 17/1604* (2013.01); *A61B 17/1671* (2013.01); *A61F 2/0095* (2013.01); *A61F 2002/30131* (2013.01); *A61F 2002/30301* (2013.01); *A61F 2002/30713* (2013.01); *A61F 2002/30714* (2013.01); *A61F 2002/30841* (2013.01); *A61F 2002/30884* (2013.01);
(Continued)

(58) Field of Classification Search
CPC .................. A61F 2/0095; A61F 2/4611; A61F 2002/4624; A61F 2002/4628
See application file for complete search history.

(56) References Cited

U.S. PATENT DOCUMENTS 2,774,350 A 12/1956 Cleveland, Jr.
3,486,505 A 12/1969 Morrison
(Continued)

FOREIGN PATENT DOCUMENTS

DE 19903763 A1 8/2000
DE 10005880 8/2001
(Continued)

OTHER PUBLICATIONS

International Search Report, PCT/US2009/00392, dated May 14, 2009.
(Continued)

*Primary Examiner* — Nicholas W Woodall
(74) *Attorney, Agent, or Firm* — Lerner, David, Littenberg, Krumholz & Mentlik, LLP

(57) ABSTRACT

Apparatus and methods for preparing a disc space and inserting an intervertebral disc implant therein are disclosed. Among the various instruments disclosed are a midline marker, a reference pin drill and insertion guide, a pin drill guide, a chisel guide, a sizer, a serrated broach, an implant dispenser, and an implant insertion tool. Methods of utilizing these tools are also disclosed.

14 Claims, 88 Drawing Sheets

Related U.S. Application Data division of application No. 12/321,373, filed on Jan. 16, 2009, now Pat. No. 8,579,911.

(60) Provisional application No. 61/011,554, filed on Jan. 18, 2008.

(51) Int. Cl.
| | | |
|---|---|---|
| *A61F 2/44* | (2006.01) | |
| *A61B 17/17* | (2006.01) | |
| *A61F 2/76* | (2006.01) | |
| *A61B 17/16* | (2006.01) | |
| *A61F 2/30* | (2006.01) | |

(52) U.S. Cl.
CPC .............. *A61F 2002/30904* (2013.01); *A61F 2002/4619* (2013.01); *A61F 2002/4622* (2013.01); *A61F 2002/4624* (2013.01); *A61F 2002/4658* (2013.01); *A61F 2002/4687* (2013.01); *A61F 2002/7615* (2013.01); *A61F 2230/0013* (2013.01); *A61F 2230/0095* (2013.01); *A61F 2250/0087* (2013.01); *A61F 2250/0089* (2013.01)

(56) References Cited

U.S. PATENT DOCUMENTS

| | | | |
|---|---|---|---|
| 4,733,657 A | 3/1988 | Kluger | |
| 4,759,766 A | 7/1988 | Buettner-Janz et al. | |
| 4,917,704 A | 4/1990 | Frey et al. | |
| 4,955,908 A | 9/1990 | Frey et al. | |
| 4,997,432 A | 3/1991 | Keller | |
| 5,002,576 A | 3/1991 | Fuhrmann et al. | |
| 5,122,130 A | 6/1992 | Keller et al. | |
| 5,192,327 A | 3/1993 | Brantigan | |
| 5,236,460 A | 8/1993 | Barber | |
| 5,246,458 A | 9/1993 | Graham | |
| 5,258,031 A | 11/1993 | Salib et al. | |
| 5,312,412 A | 5/1994 | Whipple | |
| 5,314,477 A | 5/1994 | Marnay et al. | |
| 5,401,269 A | 3/1995 | Buttner-Janz et al. | |
| 5,425,773 A | 6/1995 | Boyd et al. | |
| 5,443,514 A | 8/1995 | Steffee | |
| 5,458,641 A | 10/1995 | Ramirez Jimenez et al. | |
| 5,507,816 A | 4/1996 | Bullivant et al. | |
| 5,556,431 A | 9/1996 | Buttner-Janz | |
| 5,562,738 A | 10/1996 | Boyd et al. | |
| 5,597,384 A | 1/1997 | Walker et al. | |
| 5,645,605 A | 7/1997 | Klawitter | |
| 5,674,296 A | 10/1997 | Bryan et al. | |
| 5,676,701 A | 10/1997 | Yuan et al. | |
| 5,683,464 A | 11/1997 | Wagner et al. | |
| 5,732,992 A | 3/1998 | Mauldin | |
| 5,755,796 A | 5/1998 | Ibo et al. | |
| 5,865,846 A | 2/1999 | Bryan et al. | |
| 5,888,223 A | 3/1999 | Bray, Jr. | |
| 5,888,226 A | 3/1999 | Rogozinski | |
| 5,899,941 A | 5/1999 | Nishijima | |
| 5,916,267 A | 6/1999 | Tienboon | |
| 6,001,130 A | 12/1999 | Bryan et al. | |
| 6,019,792 A | 2/2000 | Cauthen | |
| 6,022,356 A | 2/2000 | Noyes et al. | |
| 6,039,763 A | 3/2000 | Shelokov | |
| 6,045,552 A | 4/2000 | Zucherman et al. | |
| 6,063,121 A | 5/2000 | Xavier et al. | |
| 6,066,174 A | 5/2000 | Farris | |
| 6,066,175 A | 5/2000 | Henderson et al. | |
| 6,093,205 A | 7/2000 | McLeod et al. | |
| 6,110,179 A | 8/2000 | Flivik et al. | |
| 6,113,637 A | 9/2000 | Gill et al. | |
| 6,113,639 A | 9/2000 | Ray et al. | |
| 6,146,421 A | 11/2000 | Gordon et al. | |
| 6,156,067 A | 12/2000 | Bryan et al. | |
| 6,159,214 A | 12/2000 | Michelson | |
| 6,159,215 A | 12/2000 | Urbahns et al. | |
| 6,174,311 B1 | 1/2001 | Branch et al. | |
| 6,179,874 B1 | 1/2001 | Cauthen | |
| 6,190,413 B1 | 2/2001 | Sutcliffe et al. | |
| 6,214,005 B1 | 4/2001 | Benzel et al. | |
| 6,228,118 B1 | 5/2001 | Gordon | |
| 6,241,769 B1 | 6/2001 | Nicholson et al. | |
| 6,261,293 B1 | 7/2001 | Nicholson et al. | |
| 6,261,296 B1 | 7/2001 | Aebi et al. | |
| 6,290,724 B1 | 9/2001 | Marino | |
| 6,296,647 B1 | 10/2001 | Robioneck et al. | |
| 6,319,257 B1 | 11/2001 | Carignan et al. | |
| 6,332,887 B1 | 12/2001 | Knox | |
| 6,368,350 B1 | 4/2002 | Erickson et al. | |
| 6,395,030 B1 | 5/2002 | Songer et al. | |
| 6,395,032 B1 | 5/2002 | Gauchet | |
| 6,416,551 B1 | 7/2002 | Keller | |
| 6,425,920 B1 | 7/2002 | Hamada | |
| 6,432,106 B1 | 8/2002 | Fraser et al. | |
| 6,440,139 B2 | 8/2002 | Michelson | |
| 6,461,359 B1 | 10/2002 | Tribus et al. | |
| 6,478,800 B1 | 11/2002 | Fraser et al. | |
| 6,517,580 B1 | 2/2003 | Ramadan et al. | |
| 6,527,804 B1 | 3/2003 | Gauchet et al. | |
| 6,540,785 B1 | 4/2003 | Gill et al. | |
| 6,562,073 B2 | 5/2003 | Foley | |
| 6,576,017 B2 | 6/2003 | Foley et al. | |
| 6,579,320 B1 | 6/2003 | Gauchet et al. | |
| 6,582,466 B1 | 6/2003 | Gauchet et al. | |
| 6,582,468 B1 | 6/2003 | Gauchet et al. | |
| 6,607,559 B2 | 8/2003 | Ralph et al. | |
| 6,610,093 B1 | 8/2003 | Pisharodi | |
| 6,679,915 B1 | 1/2004 | Cauthen | |
| 6,682,562 B2 | 1/2004 | Viart et al. | |
| 6,706,068 B2 | 3/2004 | Ferree | |
| 6,712,825 B2 | 3/2004 | Aebi et al. | |
| 6,740,087 B2 | 5/2004 | Knox | |
| 6,740,118 B2 | 5/2004 | Eisermann et al. | |
| 6,755,841 B2 | 6/2004 | Fraser et al. | |
| 6,770,096 B2 | 8/2004 | Bolger et al. | |
| 6,840,941 B2 | 1/2005 | Rogers et al. | |
| 6,896,676 B2 | 5/2005 | Zubok et al. | |
| 6,908,484 B2 | 6/2005 | Zubok et al. | |
| 6,953,431 B2 | 10/2005 | Barthel | |
| 6,972,037 B2 | 12/2005 | Zubok et al. | |
| 6,972,038 B2 | 12/2005 | Zubok et al. | |
| 6,989,032 B2 | 1/2006 | Errico et al. | |
| 6,994,728 B2 | 2/2006 | Zubok et al. | |
| 6,994,729 B2 | 2/2006 | Zubok et al. | |
| 6,997,954 B2 | 2/2006 | Zubok et al. | |
| 7,022,139 B2 | 4/2006 | Errico et al. | |
| 7,060,098 B2 | 6/2006 | Errico et al. | |
| 7,066,959 B2 | 6/2006 | Errico et al. | |
| 7,101,399 B2 | 9/2006 | Errico et al. | |
| 7,118,580 B1 | 10/2006 | Beyersdorff et al. | |
| 7,118,599 B2 | 10/2006 | Errico et al. | |
| 7,141,069 B2 | 11/2006 | Errico et al. | |
| 7,147,642 B2 | 12/2006 | Grinberg et al. | |
| 7,153,304 B2 | 12/2006 | Robie et al. | |
| 7,169,182 B2 | 1/2007 | Errico et al. | |
| 7,204,852 B2 | 4/2007 | Marnay et al. | |
| 7,217,292 B2 | 5/2007 | Ralph et al. | |
| 7,226,452 B2 | 6/2007 | Zubok et al. | |
| 7,235,104 B2 | 6/2007 | Grinberg et al. | |
| 7,238,203 B2 | 7/2007 | Bagga et al. | |
| 7,258,699 B2 | 8/2007 | Errico et al. | |
| 7,300,441 B2 | 11/2007 | Haid et al. | |
| 7,320,689 B2 | 1/2008 | Keller | |
| 7,435,845 B2 | 10/2008 | Dahlmann et al. | |
| 7,527,629 B2 | 5/2009 | Link et al. | |
| 7,563,285 B2 | 7/2009 | Ralph et al. | |
| 7,604,664 B2 | 10/2009 | Ralph et al. | |
| 7,794,465 B2 | 9/2010 | Marik et al. | |
| 7,892,285 B2 * | 2/2011 | Viker | A61F 2/442 606/249 |
| 8,123,757 B2 * | 2/2012 | Zalenski | A61F 2/4611 606/99 |
| 8,465,546 B2 * | 6/2013 | Jodaitis | A61F 2/442 623/17.16 |

(56) References Cited

U.S. PATENT DOCUMENTS

| | | | |
|---|---|---|---|
| 8,506,631 B2 * | 8/2013 | de Villiers | A61F 2/4425 606/99 |
| 8,840,667 B1 | 9/2014 | Tumialan | |
| 2001/0005796 A1 | 6/2001 | Zdeblick et al. | |
| 2001/0010001 A1 | 7/2001 | Michelson | |
| 2001/0027343 A1 | 10/2001 | Keller | |
| 2002/0004683 A1 | 1/2002 | Michelson | |
| 2002/0045904 A1 | 4/2002 | Fuss et al. | |
| 2002/0058944 A1 | 5/2002 | Michelson | |
| 2002/0082597 A1 | 6/2002 | Fraser | |
| 2002/0082701 A1 | 6/2002 | Zdeblick et al. | |
| 2002/0107571 A1 | 8/2002 | Foley | |
| 2002/0107572 A1 | 8/2002 | Foley et al. | |
| 2002/0116009 A1 | 8/2002 | Fraser et al. | |
| 2002/0123750 A1 | 9/2002 | Eisermann et al. | |
| 2002/0128715 A1 | 9/2002 | Bryan et al. | |
| 2002/0143399 A1 | 10/2002 | Sutcliffe | |
| 2002/0169508 A1 | 11/2002 | Songer et al. | |
| 2002/0193880 A1 | 12/2002 | Fraser | |
| 2003/0028197 A1 | 2/2003 | Hanson et al. | |
| 2003/0040796 A1 | 2/2003 | Ferree | |
| 2003/0055503 A1 | 3/2003 | O'Neil | |
| 2003/0069586 A1 | 4/2003 | Errico et al. | |
| 2003/0069642 A1 | 4/2003 | Ralph et al. | |
| 2003/0074070 A1 | 4/2003 | Errico et al. | |
| 2003/0078668 A1 | 4/2003 | Michelson | |
| 2003/0100949 A1 | 5/2003 | Michelson | |
| 2003/0120344 A1 | 6/2003 | Michelson | |
| 2003/0167091 A1 | 9/2003 | Scharf | |
| 2003/0167092 A1 | 9/2003 | Foley | |
| 2003/0181982 A1 | 9/2003 | Kuslich | |
| 2003/0187453 A1 | 10/2003 | Schlapfer et al. | |
| 2003/0187454 A1 | 10/2003 | Gill et al. | |
| 2003/0199981 A1 | 10/2003 | Ferree | |
| 2003/0199983 A1 | 10/2003 | Michelson | |
| 2003/0204260 A1 | 10/2003 | Ferree | |
| 2003/0208274 A1 | 11/2003 | Davis | |
| 2003/0225416 A1 | 12/2003 | Bonvallet et al. | |
| 2003/0229358 A1 | 12/2003 | Errico et al. | |
| 2003/0229397 A1 | 12/2003 | Davis | |
| 2003/0233097 A1 | 12/2003 | Ferree | |
| 2003/0233145 A1 | 12/2003 | Landry et al. | |
| 2003/0233148 A1 | 12/2003 | Ferree | |
| 2003/0236524 A1 | 12/2003 | Squires et al. | |
| 2004/0002712 A1 | 1/2004 | Grinberg et al. | |
| 2004/0002758 A1 | 1/2004 | Landry et al. | |
| 2004/0002759 A1 | 1/2004 | Ferree | |
| 2004/0002761 A1 | 1/2004 | Rogers et al. | |
| 2004/0002762 A1 | 1/2004 | Hawkins | |
| 2004/0010254 A1 | 1/2004 | Cook et al. | |
| 2004/0010316 A1 | 1/2004 | William et al. | |
| 2004/0024459 A1 | 2/2004 | Ferree | |
| 2004/0024461 A1 | 2/2004 | Ferree | |
| 2004/0030387 A1 | 2/2004 | Landry et al. | |
| 2004/0030389 A1 | 2/2004 | Ferree | |
| 2004/0030390 A1 | 2/2004 | Ferree | |
| 2004/0030391 A1 | 2/2004 | Ferree | |
| 2004/0034420 A1 | 2/2004 | Errico et al. | |
| 2004/0034421 A1 | 2/2004 | Errico et al. | |
| 2004/0073312 A1 | 4/2004 | Eisermann et al. | |
| 2004/0106927 A1 | 6/2004 | Ruffner et al. | |
| 2004/0117022 A1 | 6/2004 | Marnay et al. | |
| 2004/0138522 A1 | 7/2004 | Haarstad et al. | |
| 2004/0143270 A1 | 7/2004 | Zucherman et al. | |
| 2004/0143332 A1 | 7/2004 | Krueger et al. | |
| 2004/0148028 A1 | 7/2004 | Ferree et al. | |
| 2004/0167536 A1 | 8/2004 | Errico et al. | |
| 2004/0167537 A1 | 8/2004 | Errico et al. | |
| 2004/0176772 A1 | 9/2004 | Zubok et al. | |
| 2004/0176773 A1 | 9/2004 | Zubok et al. | |
| 2004/0176774 A1 | 9/2004 | Zubok et al. | |
| 2004/0176777 A1 | 9/2004 | Zubok et al. | |
| 2004/0176778 A1 | 9/2004 | Zubok et al. | |
| 2004/0176843 A1 | 9/2004 | Zubok et al. | |
| 2004/0176851 A1 | 9/2004 | Zubok et al. | |
| 2004/0176852 A1 | 9/2004 | Zubok et al. | |
| 2004/0193272 A1 | 9/2004 | Zubok et al. | |
| 2004/0215198 A1 | 10/2004 | Marnay et al. | |
| 2004/0215203 A1 | 10/2004 | Michelson | |
| 2004/0220567 A1 | 11/2004 | Eisermann et al. | |
| 2004/0220582 A1 | 11/2004 | Keller | |
| 2004/0220590 A1 | 11/2004 | Zubok et al. | |
| 2004/0225295 A1 | 11/2004 | Zubok et al. | |
| 2004/0243240 A1 | 12/2004 | Beaurain et al. | |
| 2004/0249388 A1 | 12/2004 | Michelson | |
| 2005/0010213 A1 | 1/2005 | Stad et al. | |
| 2005/0015094 A1 | 1/2005 | Keller | |
| 2005/0015095 A1 | 1/2005 | Keller | |
| 2005/0021042 A1 | 1/2005 | Marnay et al. | |
| 2005/0033428 A1 | 2/2005 | Keller | |
| 2005/0043800 A1 | 2/2005 | Paul et al. | |
| 2005/0055029 A1 | 3/2005 | Marik et al. | |
| 2005/0055031 A1 | 3/2005 | Lim | |
| 2005/0055098 A1 | 3/2005 | Zdeblick et al. | |
| 2005/0065611 A1 | 3/2005 | Huppert et al. | |
| 2005/0071013 A1 | 3/2005 | Zubok et al. | |
| 2005/0113842 A1 | 5/2005 | Bertagnoli et al. | |
| 2005/0119665 A1 | 6/2005 | Keller | |
| 2005/0143749 A1 * | 6/2005 | Zalenski | A61F 2/4611 606/99 |
| 2005/0159819 A1 | 7/2005 | McCormack et al. | |
| 2005/0187627 A1 | 8/2005 | Ralph et al. | |
| 2005/0203533 A1 | 9/2005 | Ferguson et al. | |
| 2005/0228500 A1 | 10/2005 | Kim et al. | |
| 2005/0240270 A1 | 10/2005 | Zubok et al. | |
| 2005/0240271 A1 | 10/2005 | Zubok et al. | |
| 2005/0240272 A1 | 10/2005 | Zubok et al. | |
| 2005/0256577 A1 | 11/2005 | Baumgartner et al. | |
| 2005/0267581 A1 | 12/2005 | Marnay et al. | |
| 2006/0004377 A1 | 1/2006 | Keller | |
| 2006/0064100 A1 | 3/2006 | Bertagnoli et al. | |
| 2006/0085077 A1 | 4/2006 | Cook et al. | |
| 2006/0100634 A1 | 5/2006 | Ferguson | |
| 2006/0116768 A1 | 6/2006 | Krueger et al. | |
| 2006/0149278 A1 | 7/2006 | Abdou | |
| 2006/0167461 A1 | 7/2006 | Hawkins et al. | |
| 2006/0195114 A1 | 8/2006 | Bertagnoli | |
| 2006/0200166 A1 | 9/2006 | Hanson et al. | |
| 2006/0217731 A1 | 9/2006 | Gil et al. | |
| 2006/0235422 A1 | 10/2006 | Keller | |
| 2006/0247645 A1 | 11/2006 | Wilcox et al. | |
| 2006/0247649 A1 | 11/2006 | Rezach et al. | |
| 2007/0073403 A1 | 3/2007 | Lombardo et al. | |
| 2007/0073405 A1 | 3/2007 | Verhulst et al. | |
| 2007/0118224 A1 | 5/2007 | Shah et al. | |
| 2007/0123904 A1 | 5/2007 | Stad et al. | |
| 2007/0123985 A1 | 5/2007 | Errico et al. | |
| 2007/0123989 A1 | 5/2007 | Gfeller | |
| 2007/0191856 A1 | 8/2007 | Gil et al. | |
| 2007/0225813 A1 | 9/2007 | Haines | |
| 2007/0282448 A1 | 12/2007 | Abdou | |
| 2008/0077155 A1 | 3/2008 | Diederich et al. | |
| 2008/0082169 A1 | 4/2008 | Gittings et al. | |
| 2008/0200984 A1 * | 8/2008 | Jodaitis | A61F 2/4425 623/17.16 |
| 2008/0269756 A1 | 10/2008 | Tomko et al. | |
| 2009/0018663 A1 | 1/2009 | Cook et al. | |
| 2009/0076615 A1 | 3/2009 | Duggal et al. | |
| 2010/0100138 A1 | 4/2010 | Reynolds et al. | |
| 2010/0125277 A1 | 5/2010 | Dace et al. | |
| 2010/0152781 A1 | 6/2010 | Nehls | |
| 2010/0292693 A1 | 11/2010 | Nehls | |
| 2015/0202051 A1 | 7/2015 | Tanaka et al. | |

FOREIGN PATENT DOCUMENTS

| | | |
|---|---|---|
| EP | 1222903 A1 | 7/2002 |
| EP | 1488747 | 12/2004 |
| JP | 2008541879 A | 11/2008 |
| WO | 9113598 A1 | 9/1991 |
| WO | 0162191 A2 | 8/2001 |
| WO | 0236024 | 5/2002 |
| WO | 04/041131 A2 | 5/2004 |
| WO | 04041131 | 5/2004 |

(56) References Cited

FOREIGN PATENT DOCUMENTS

| WO | 2006039266 A2 | 4/2006 |
|---|---|---|
| WO | 2006130460 A2 | 12/2006 |
| WO | 2007000654 A2 | 1/2007 |

OTHER PUBLICATIONS

Extended European Search Report for Application No. 09702773 dated Nov. 23, 2012.

* cited by examiner

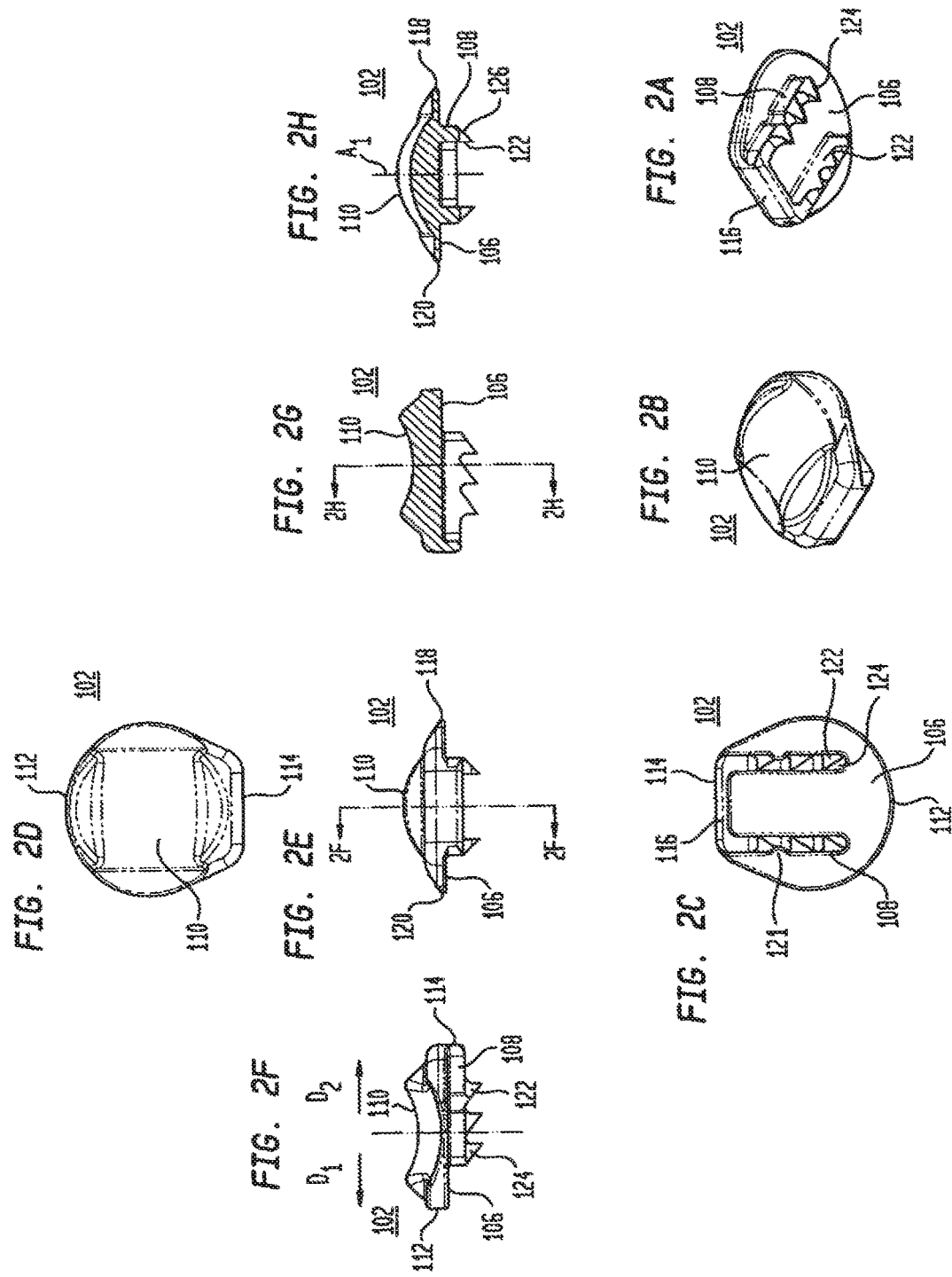

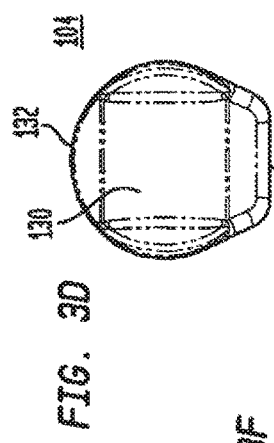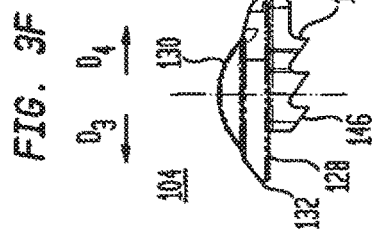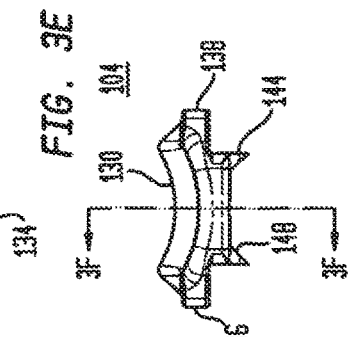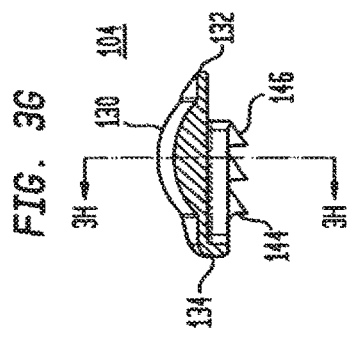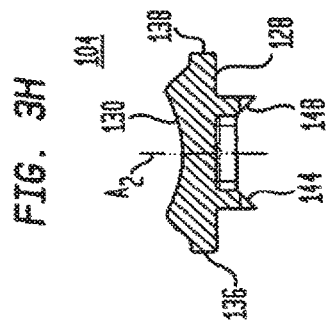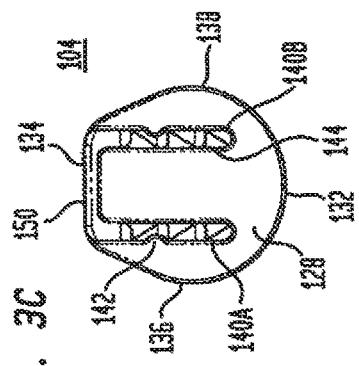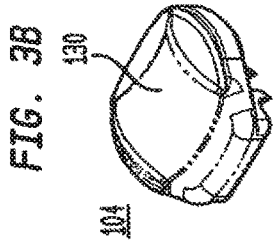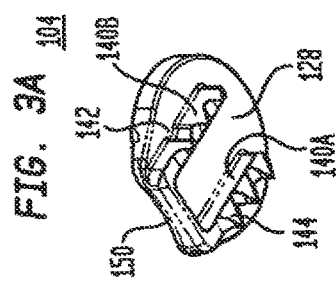

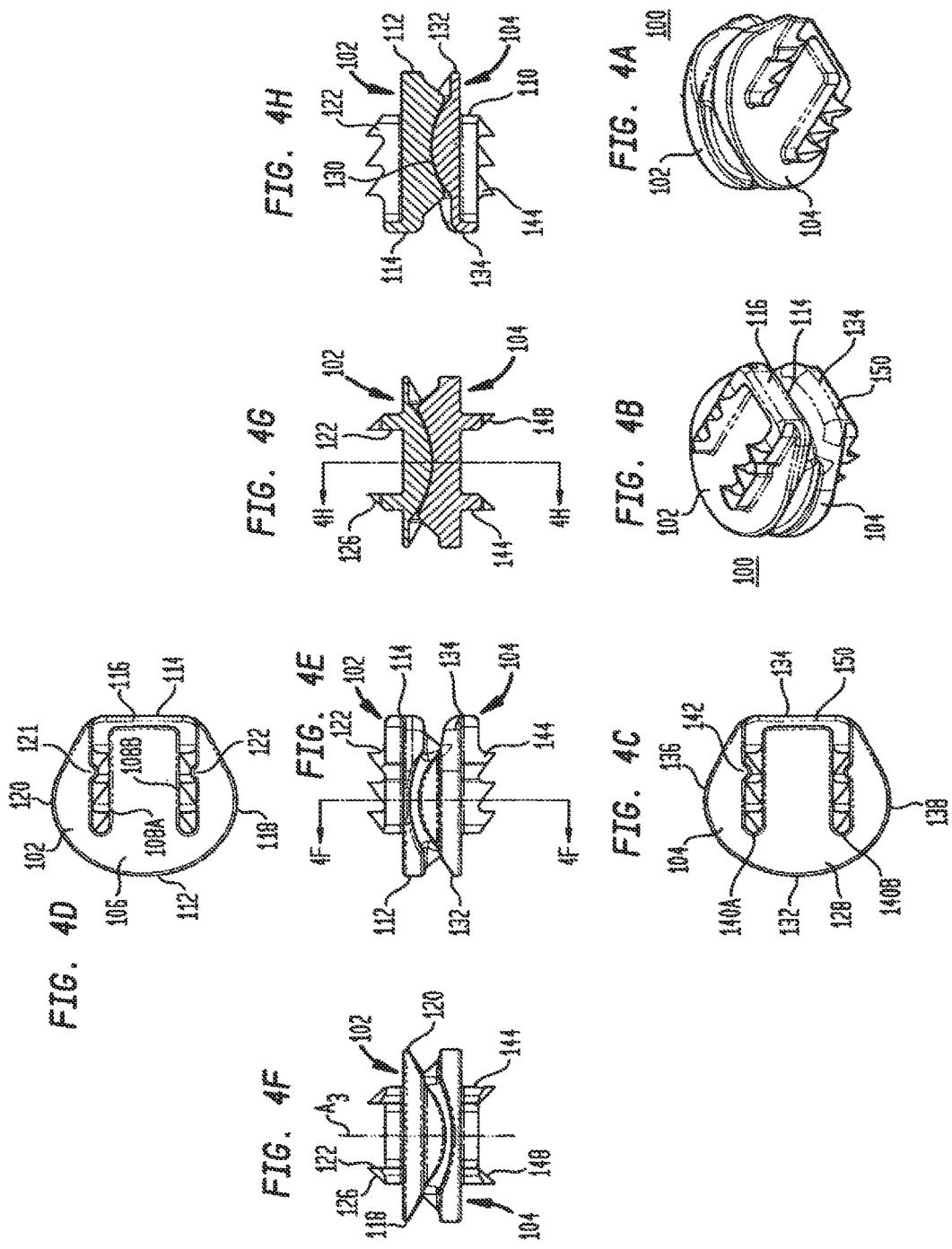

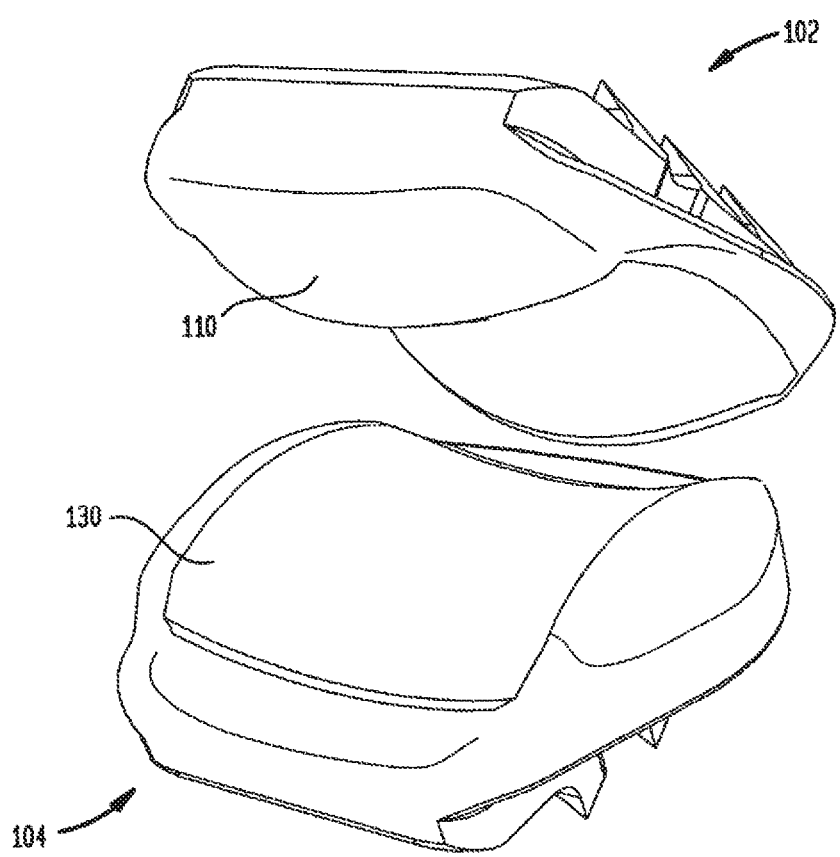

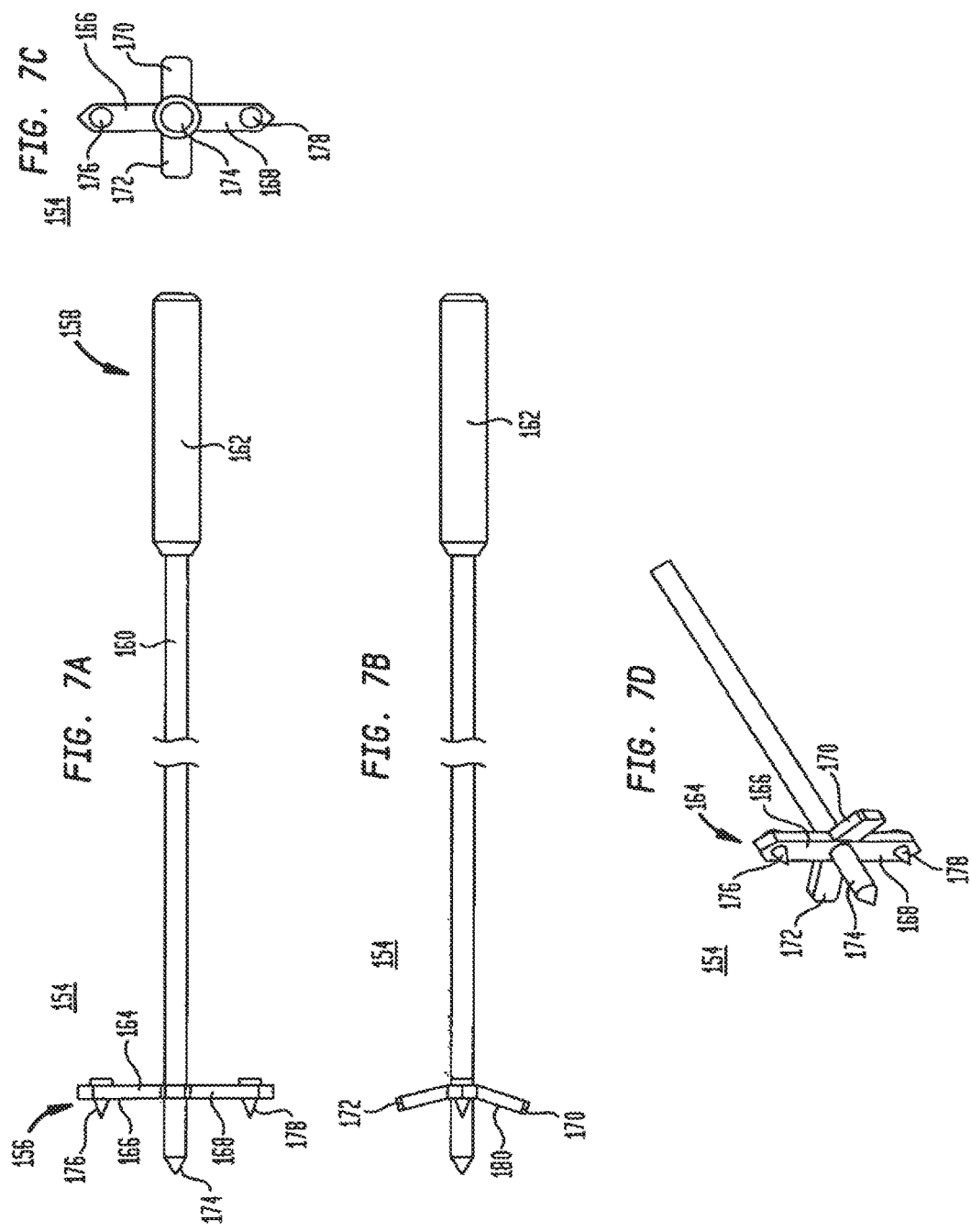

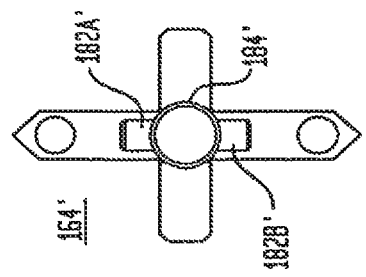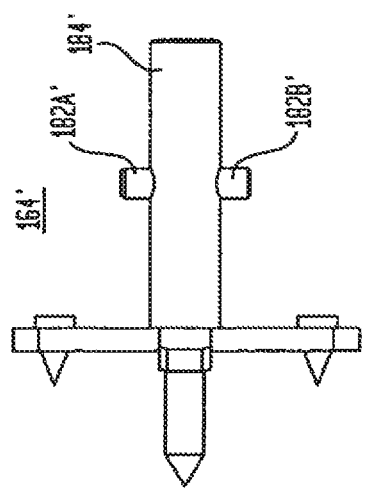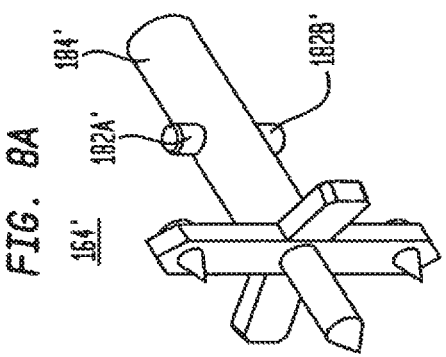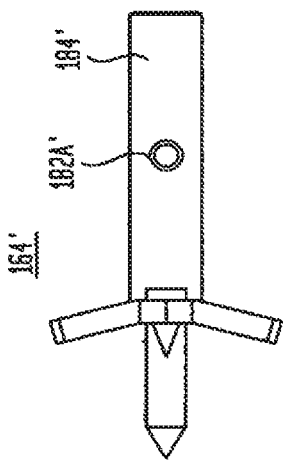

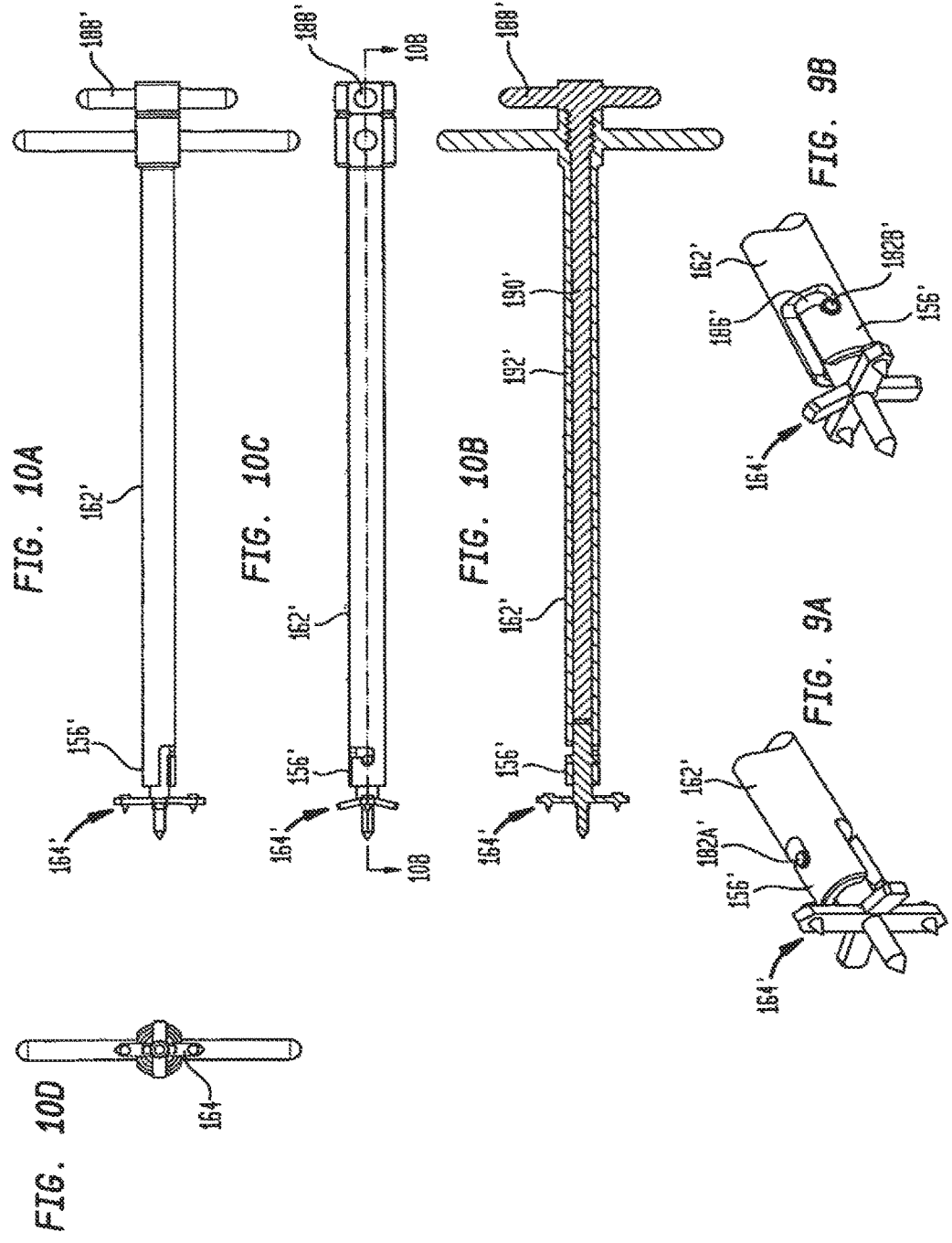

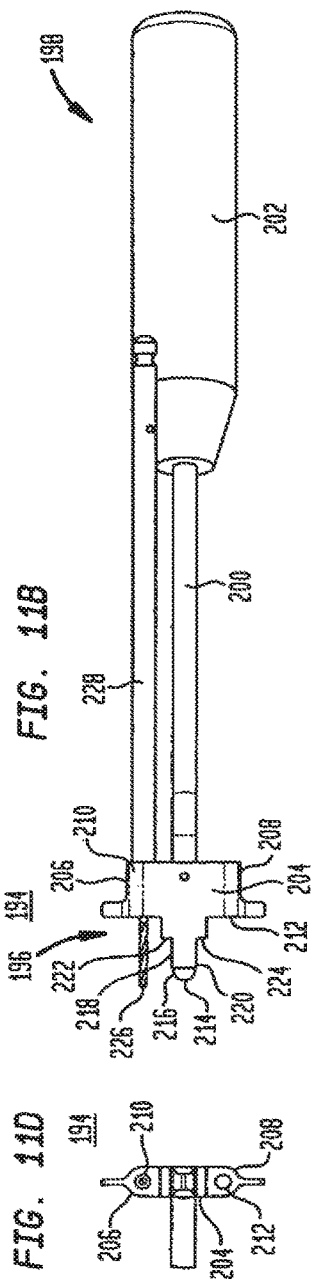
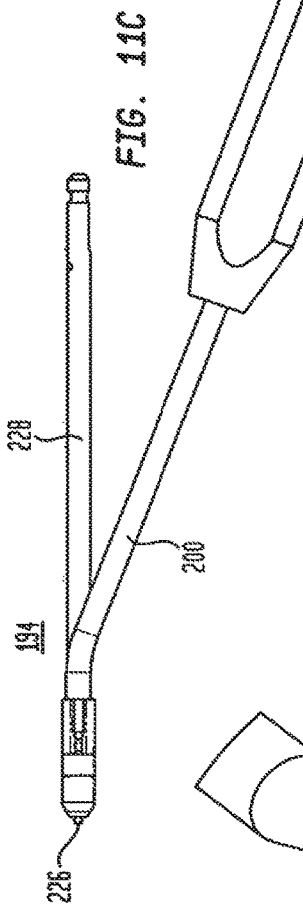
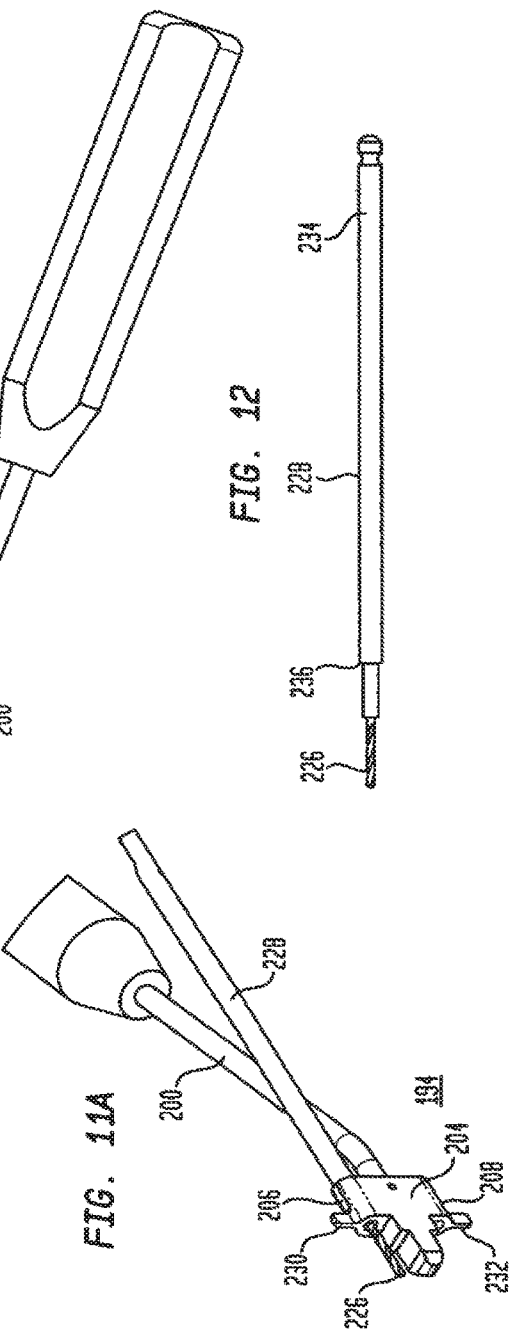

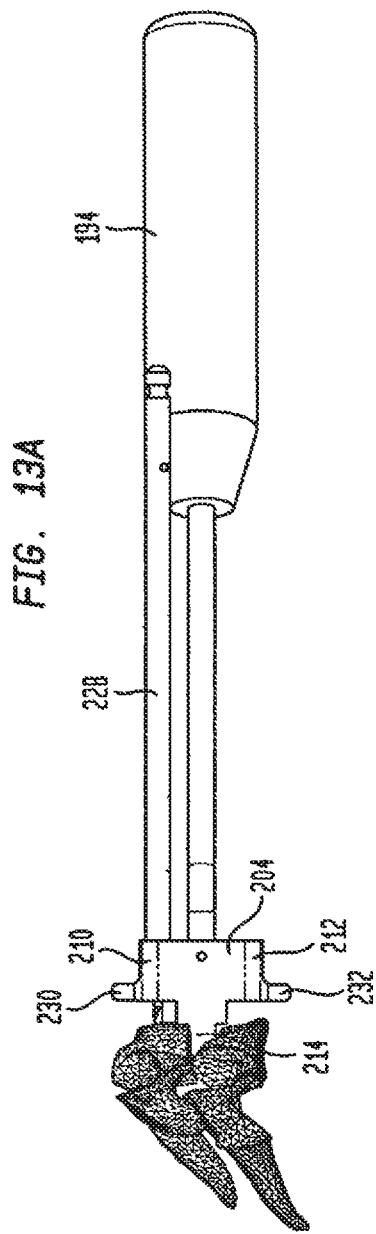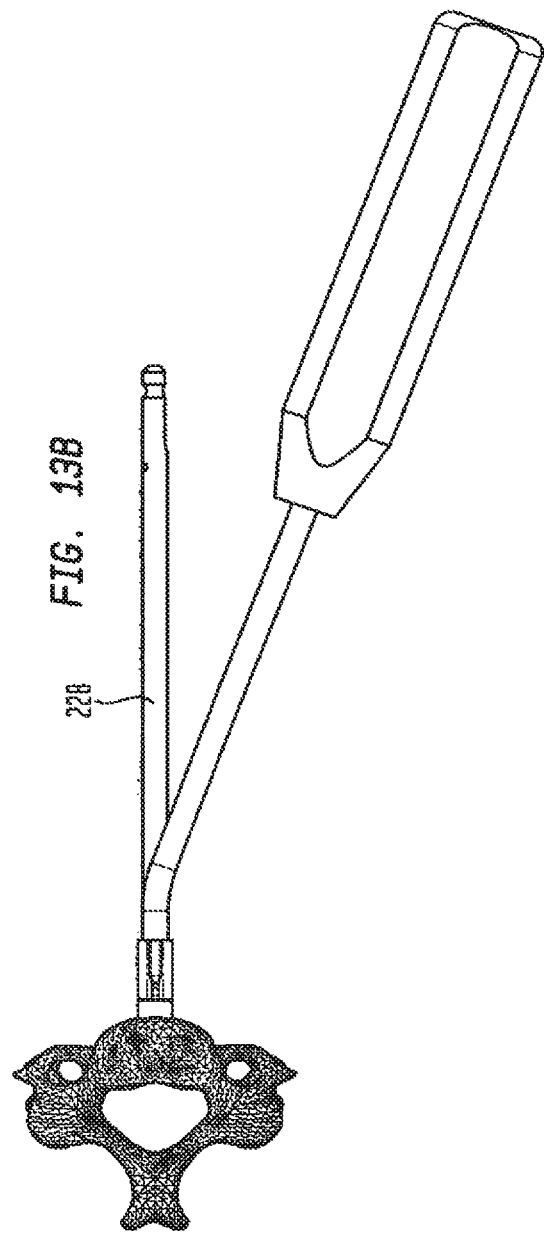

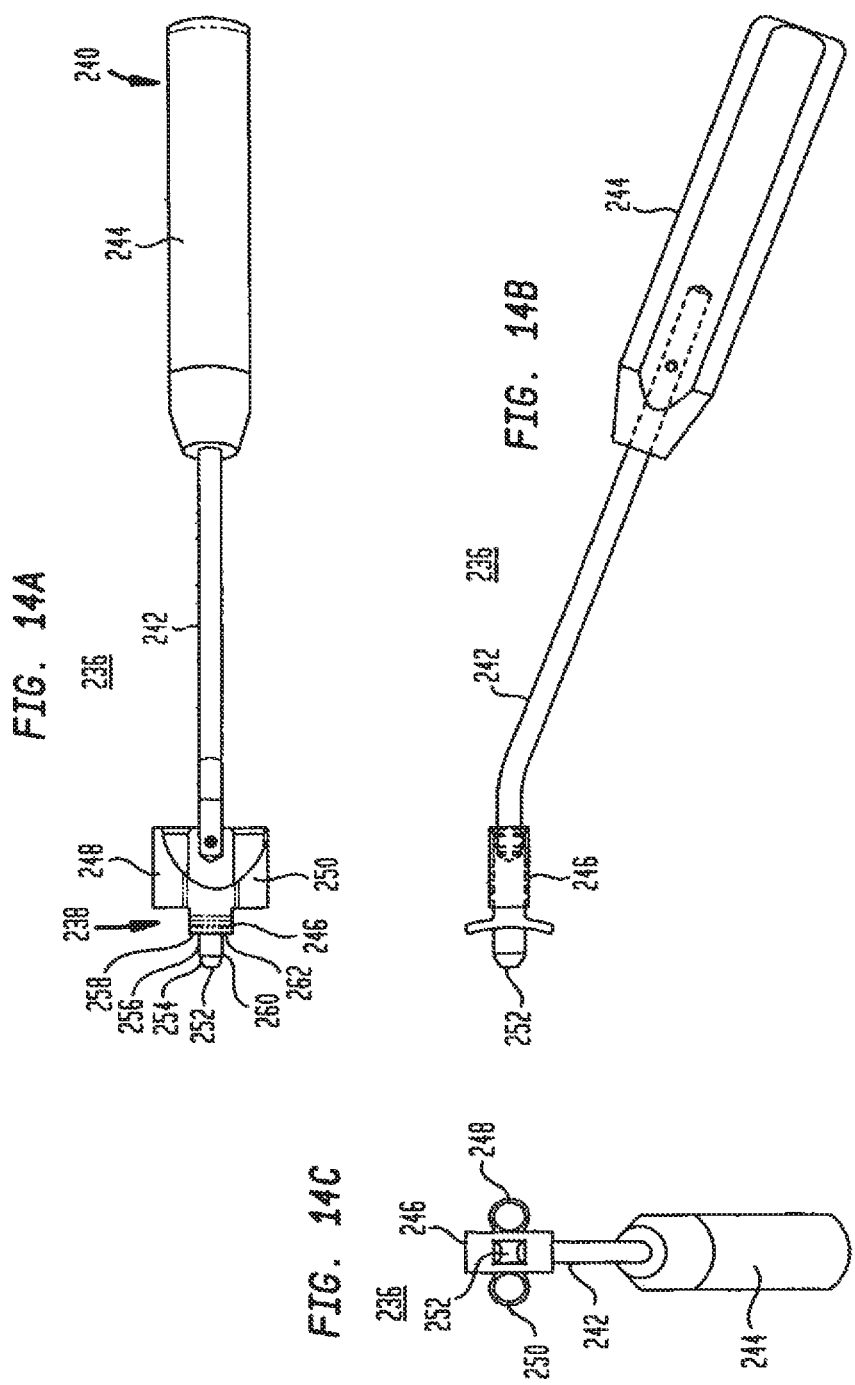

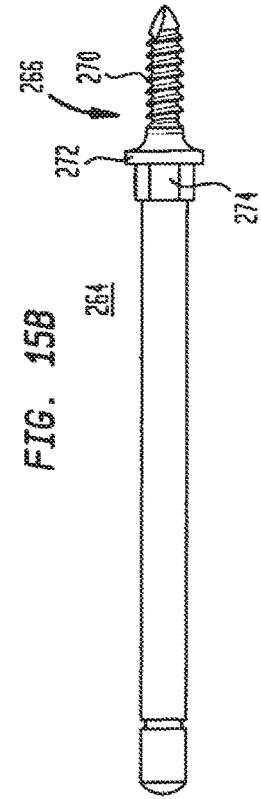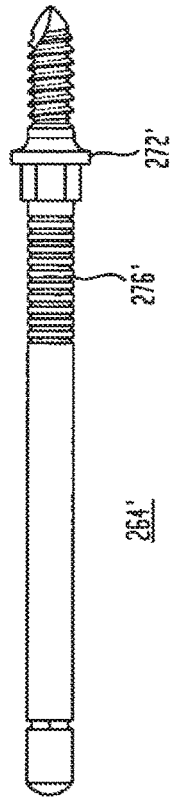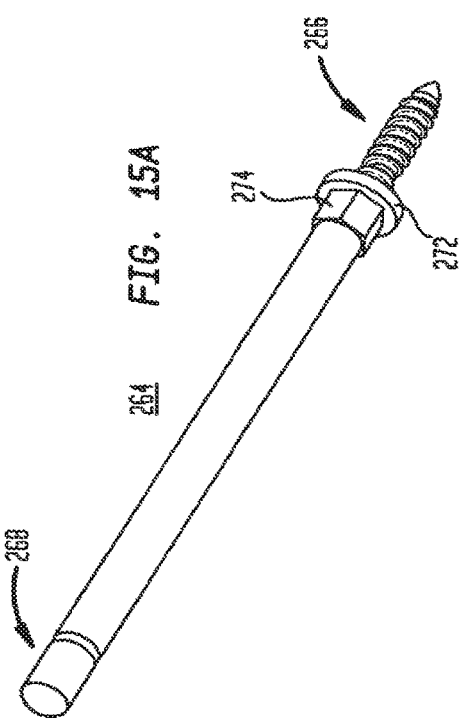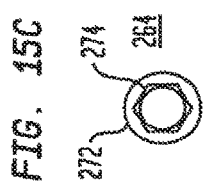

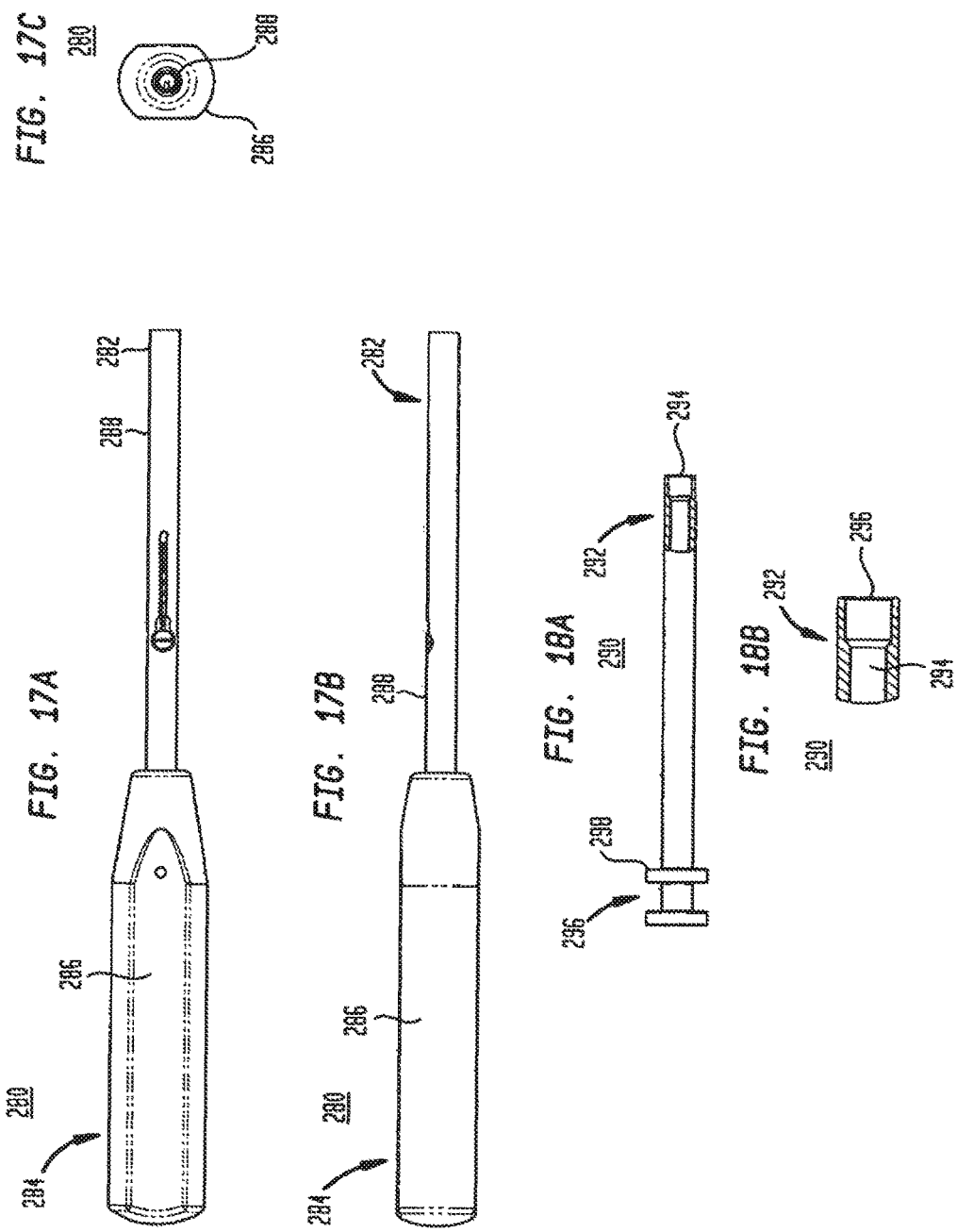

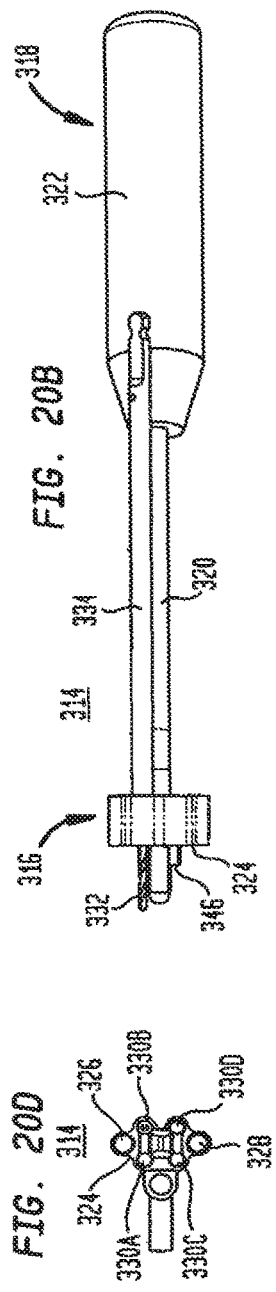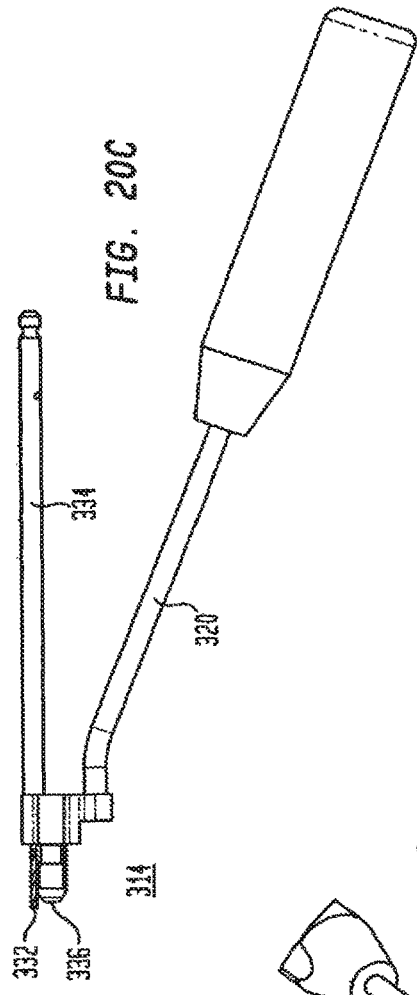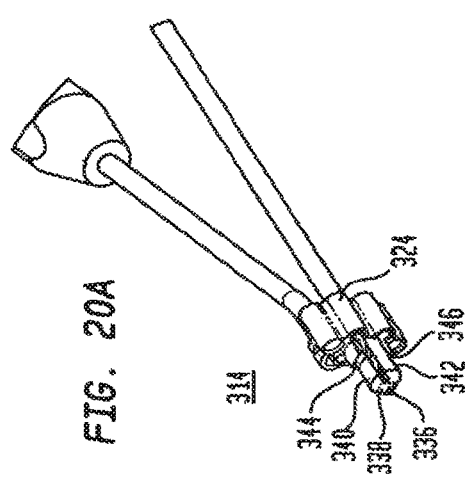

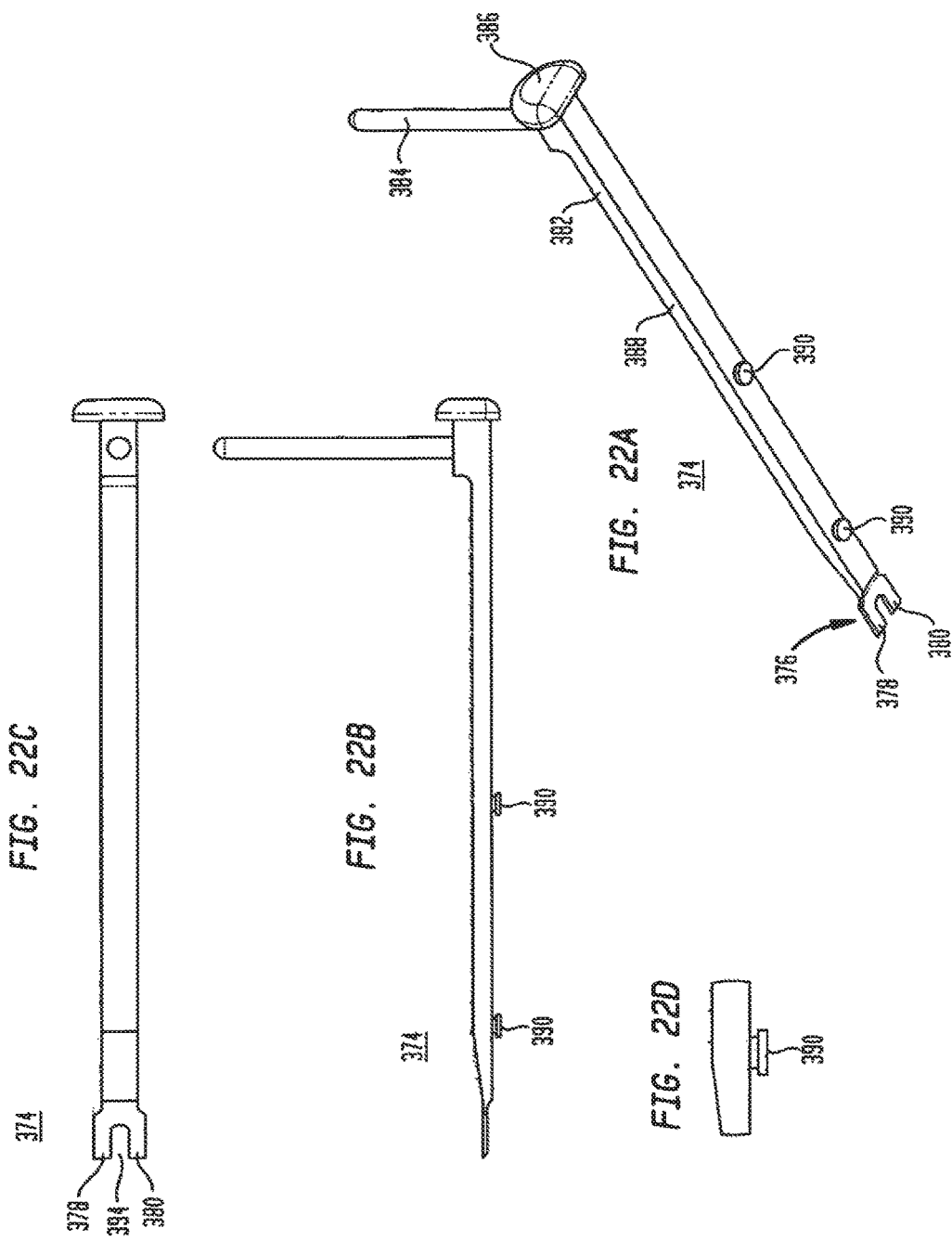

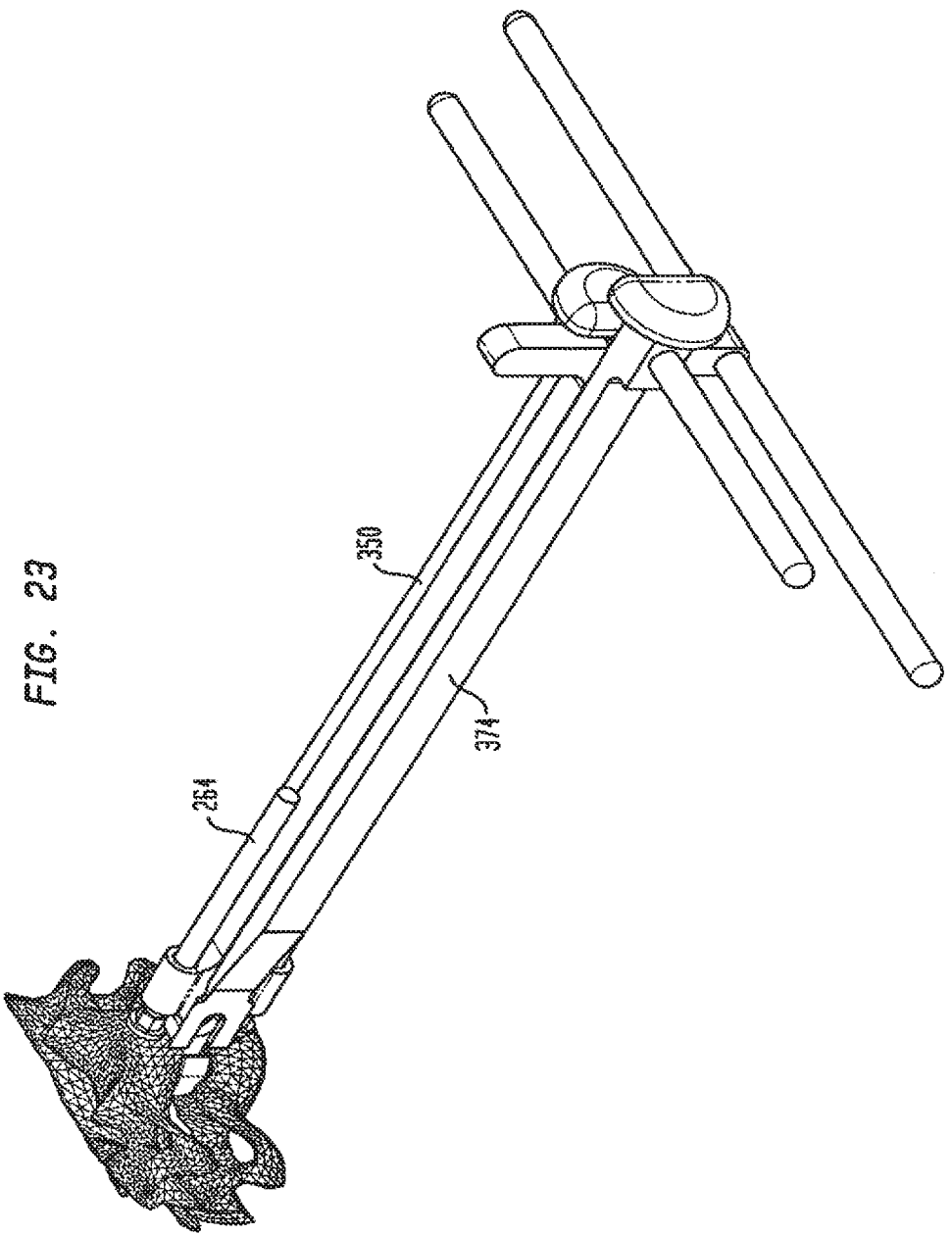

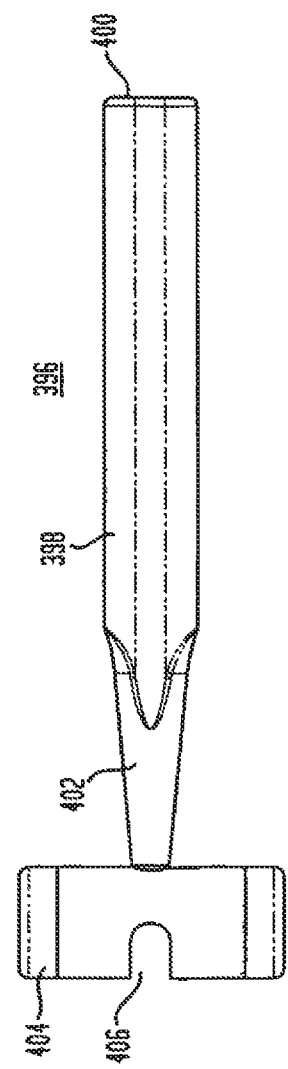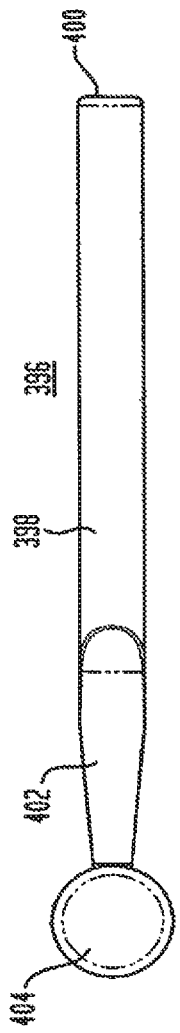

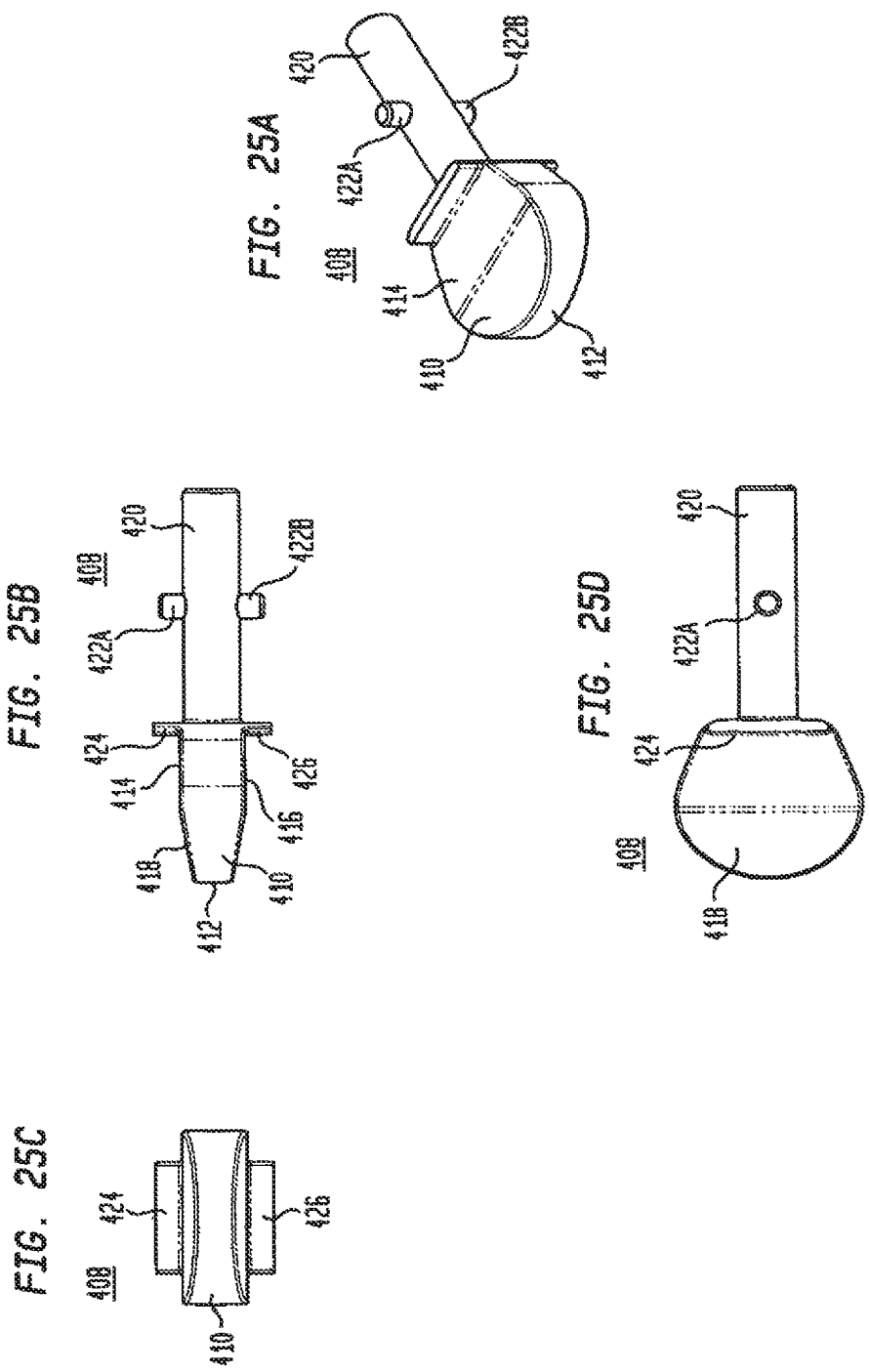

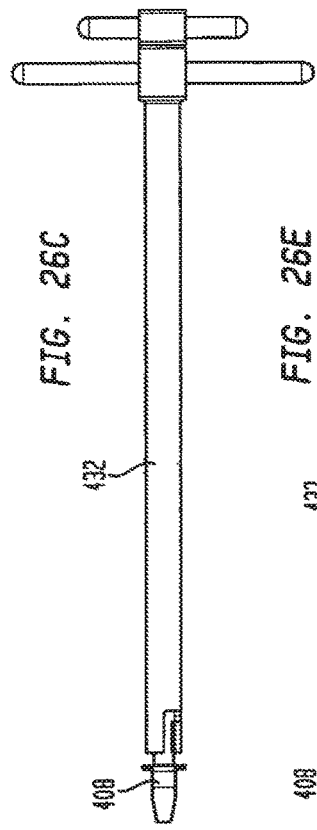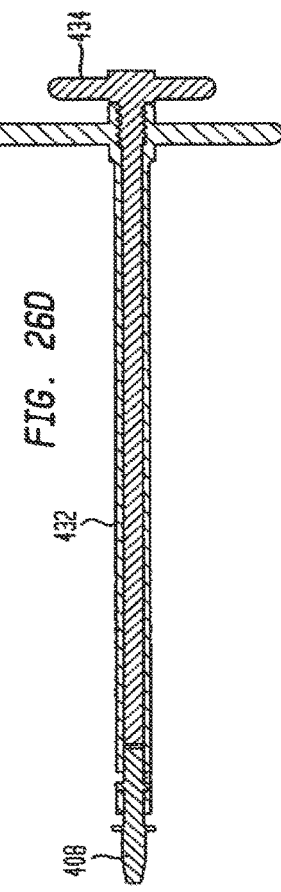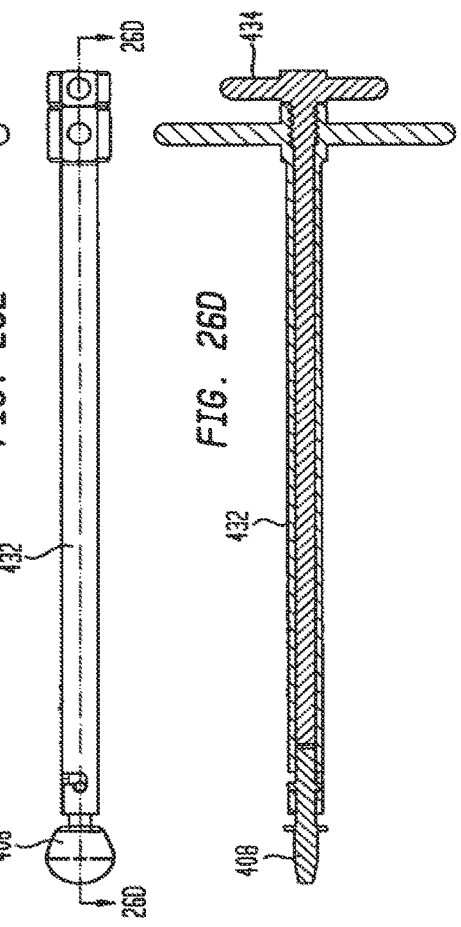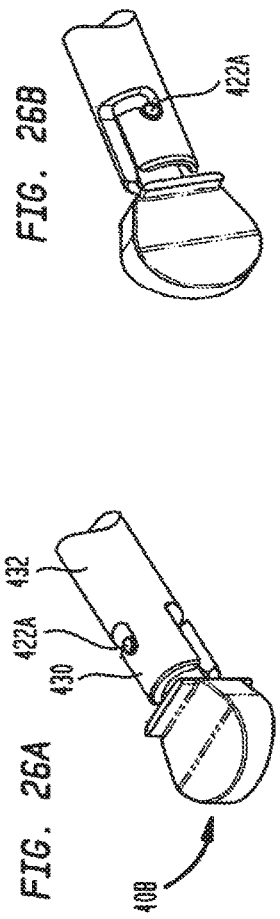

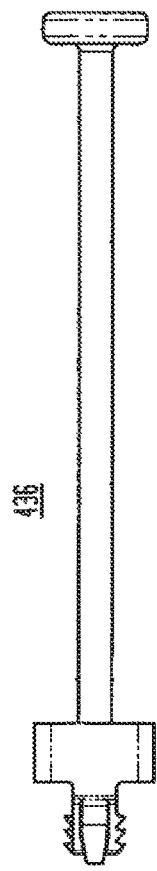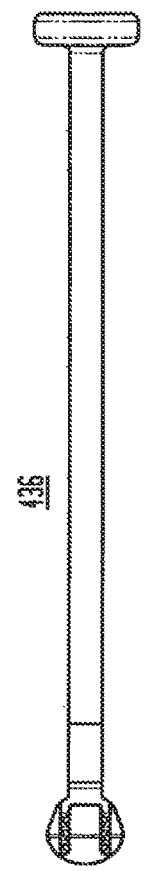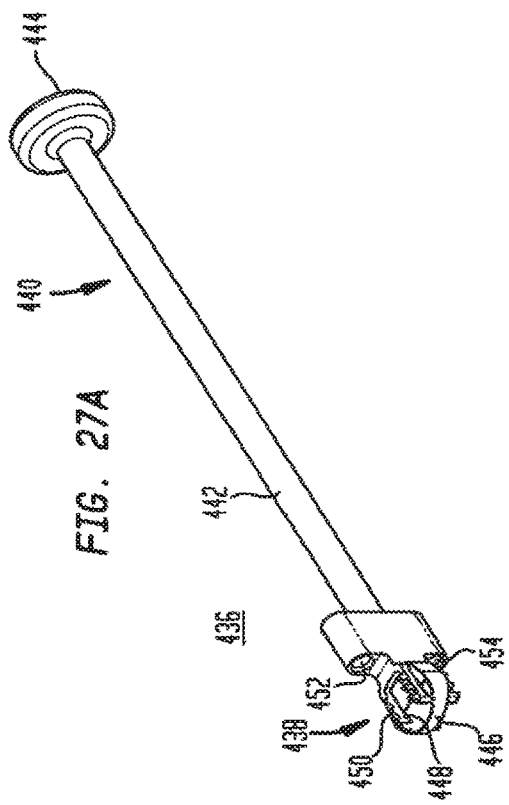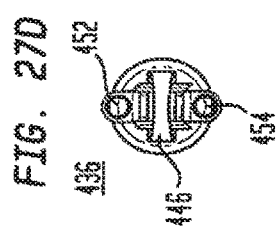

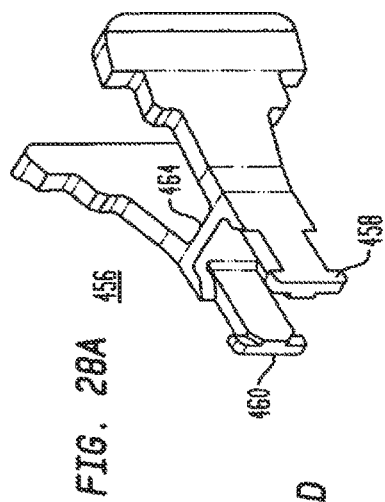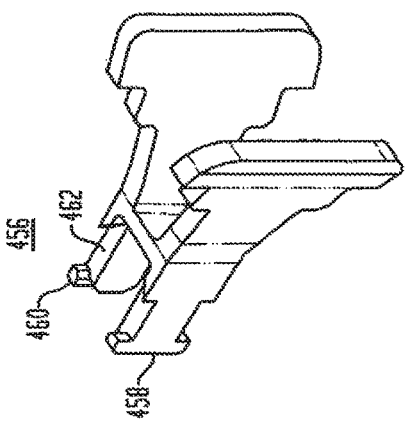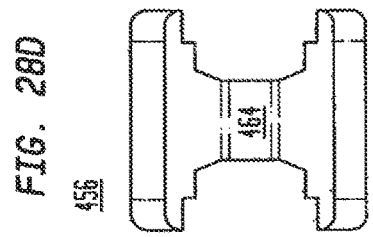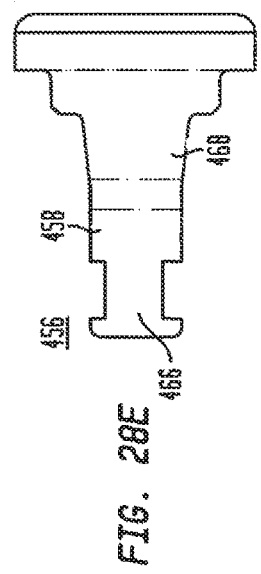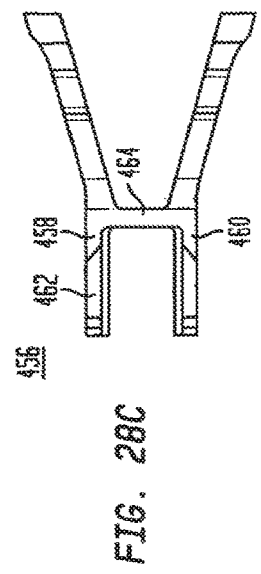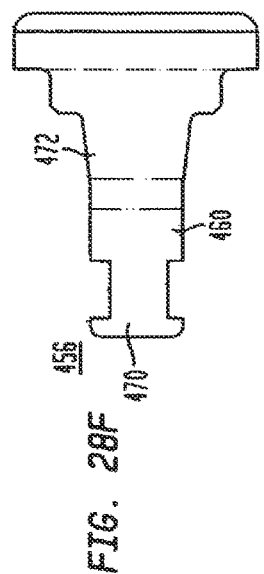

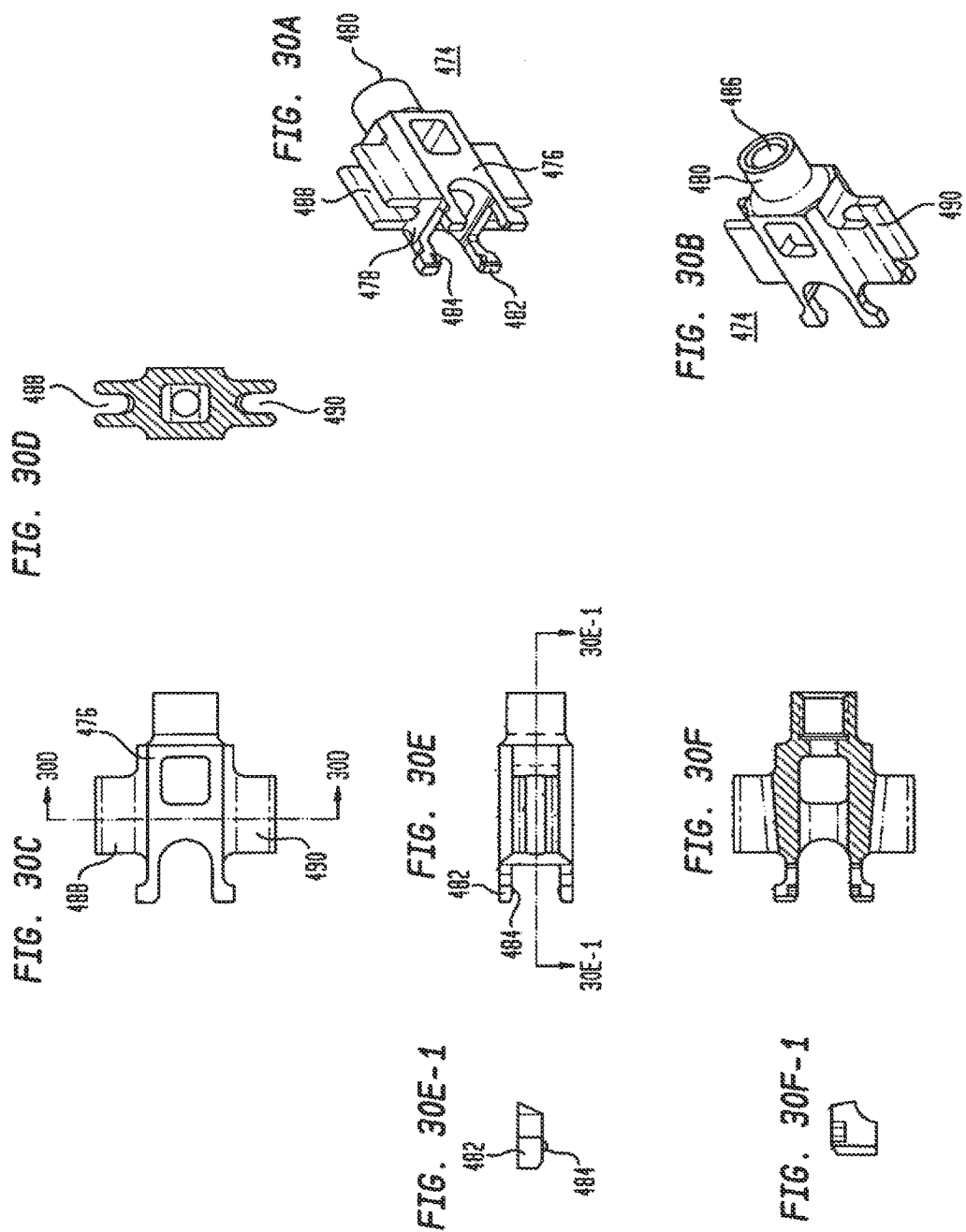

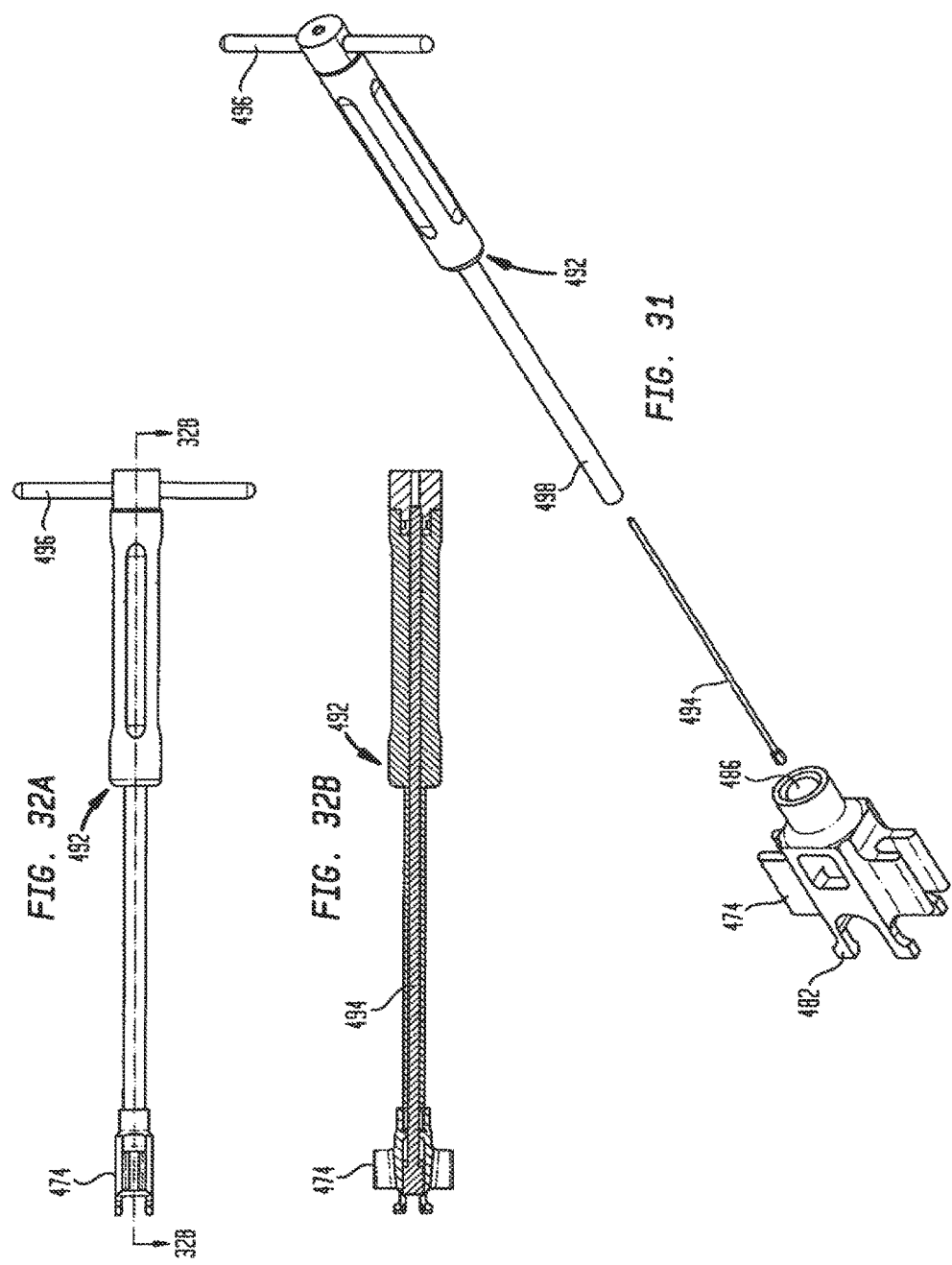

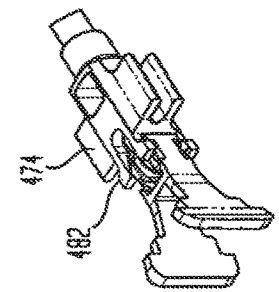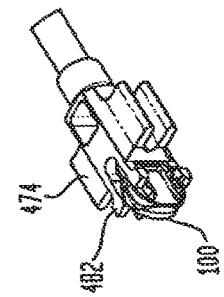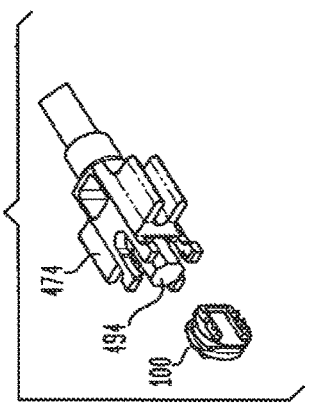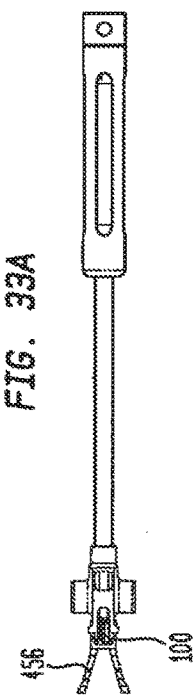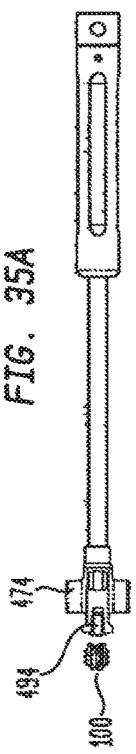

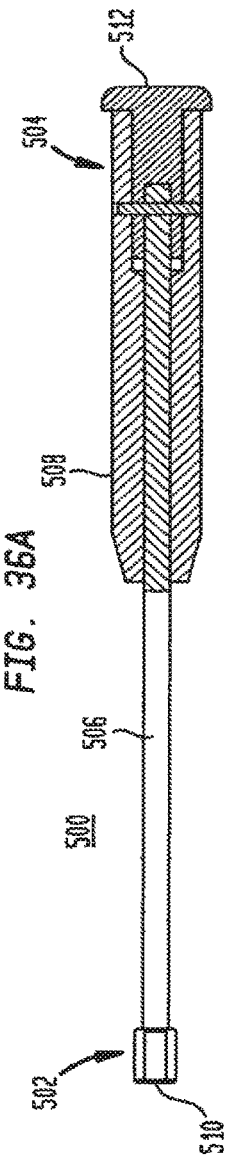
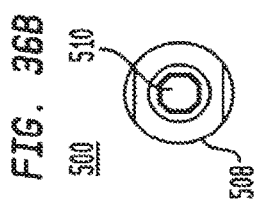
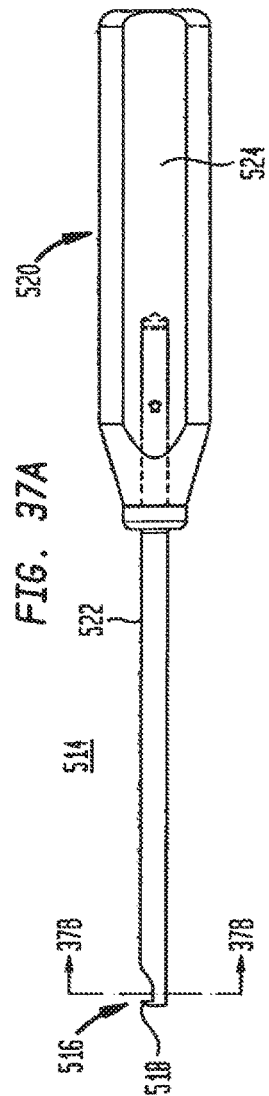
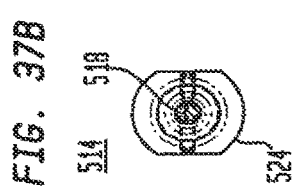
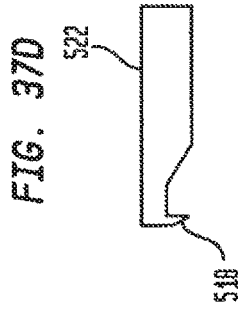
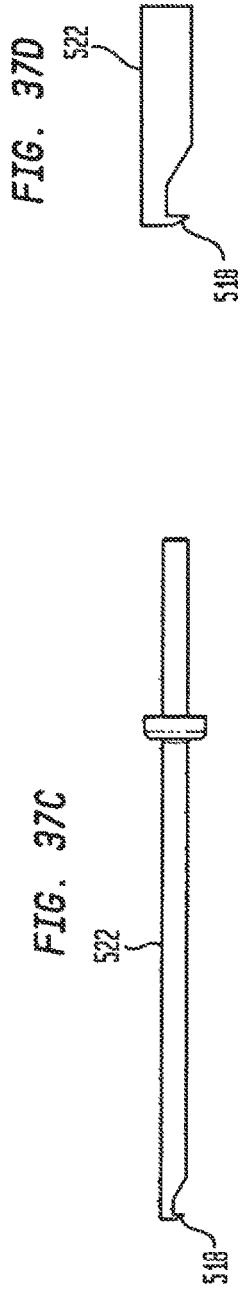

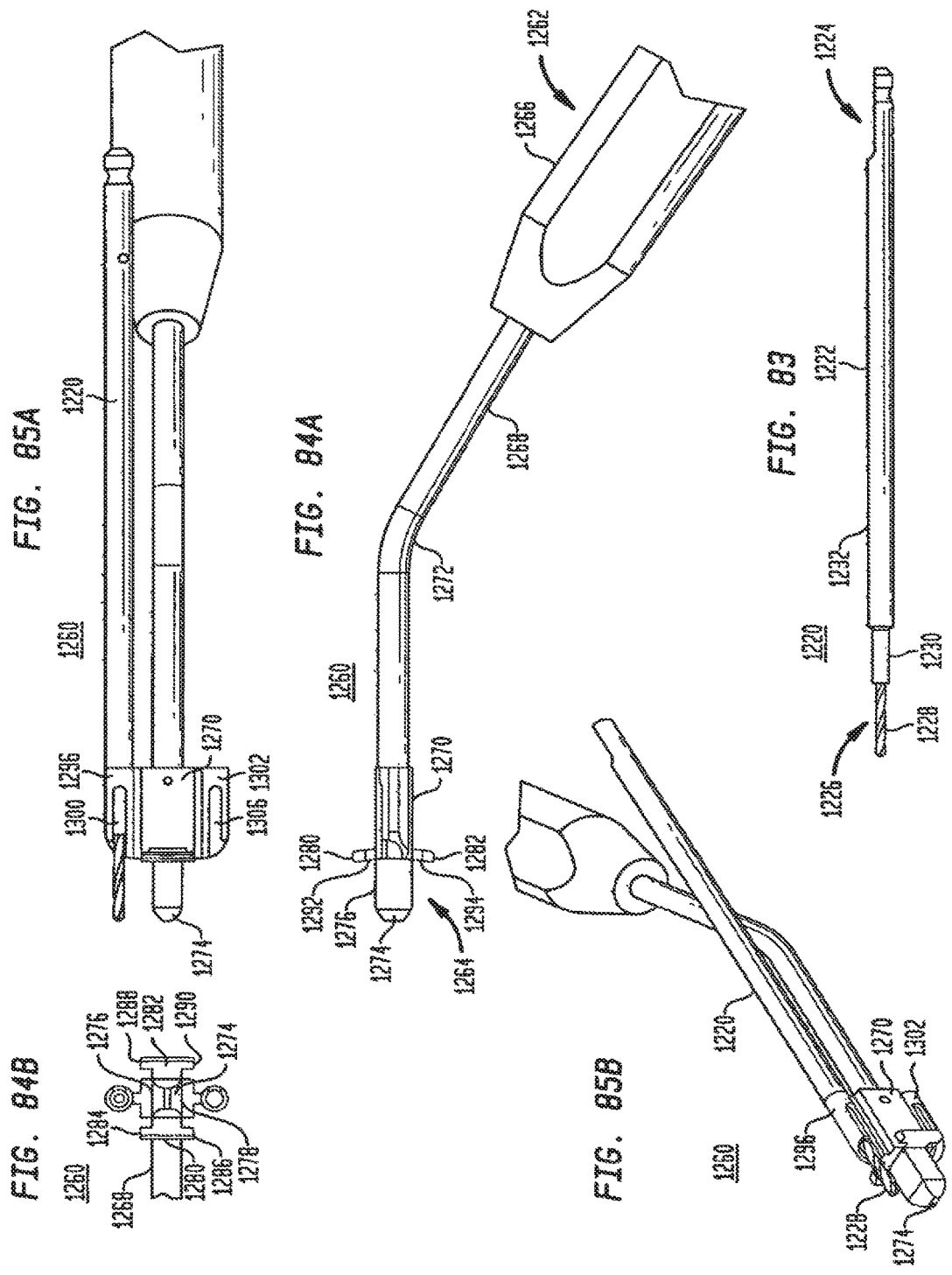

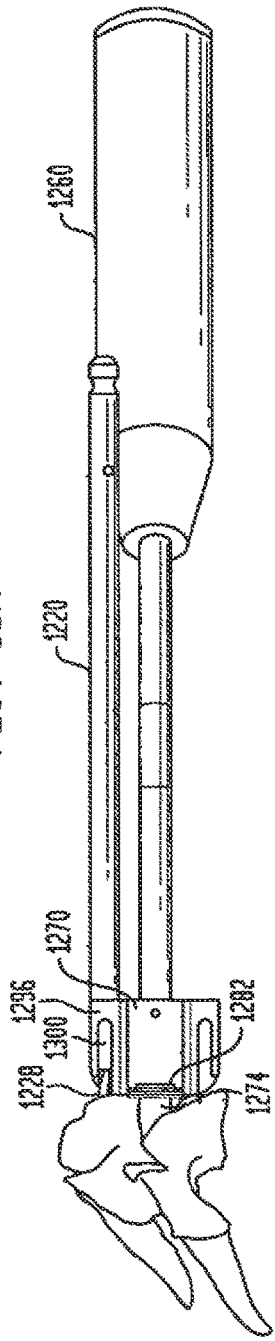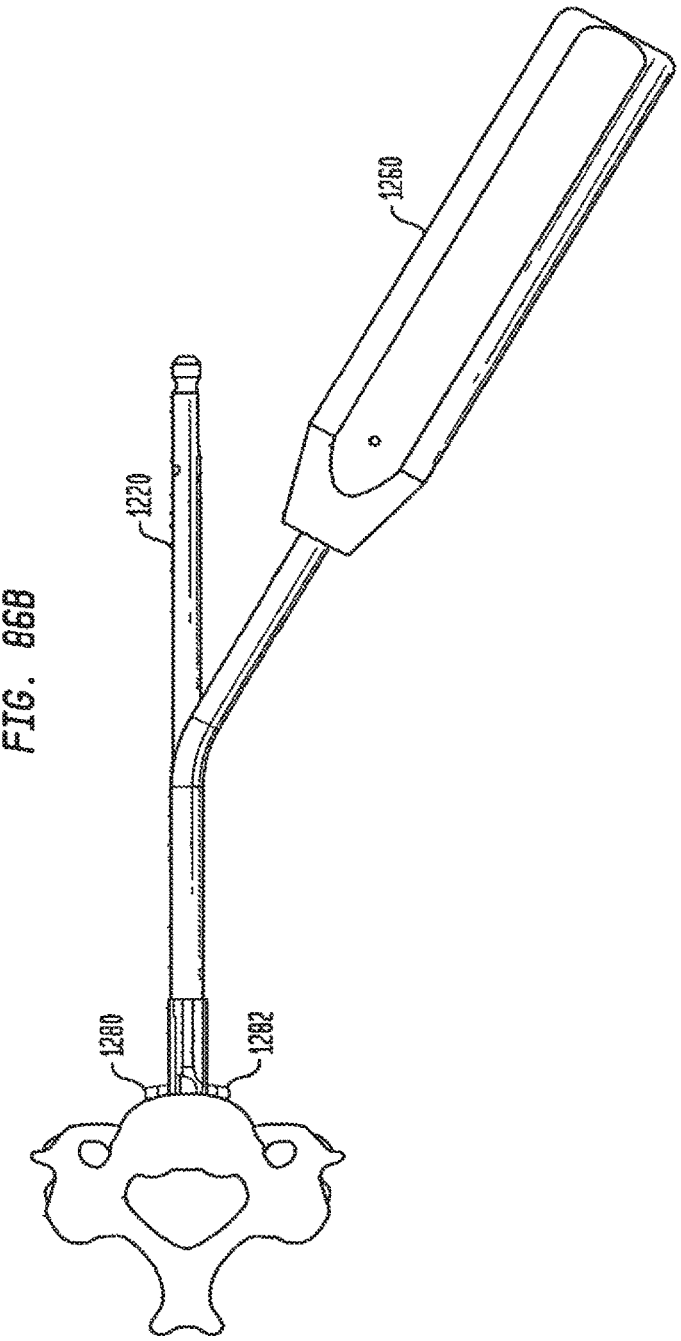

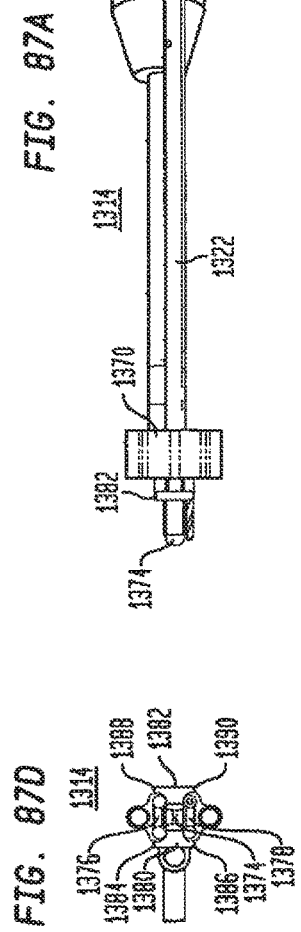
FIG. 87A
FIG. 87B
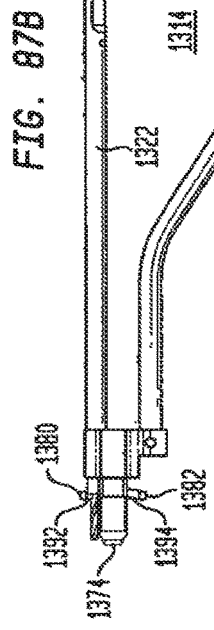
FIG. 87D
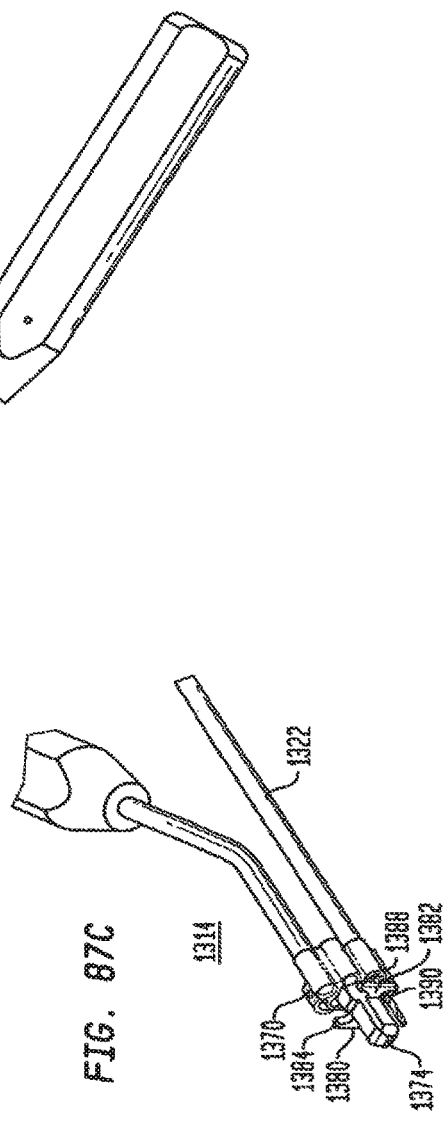
FIG. 87C

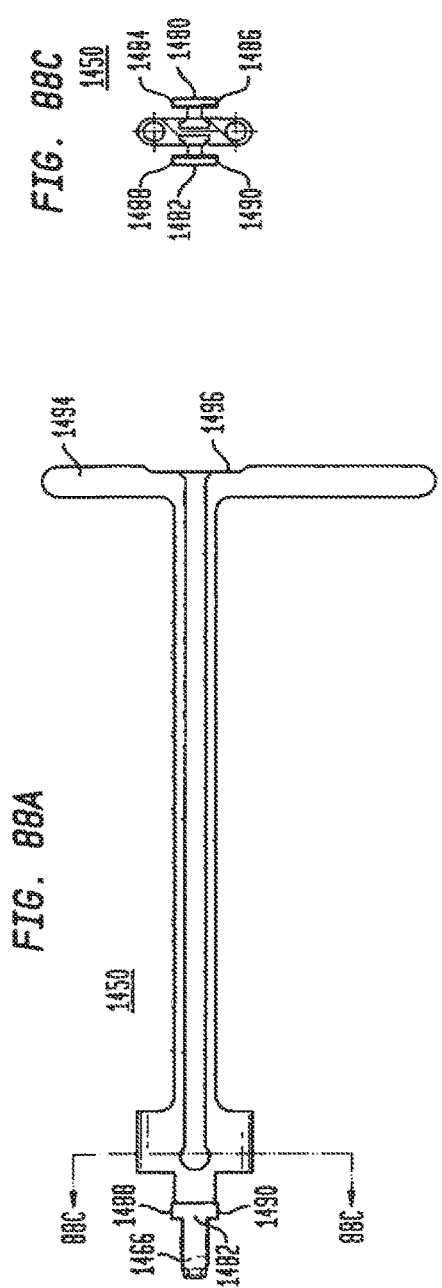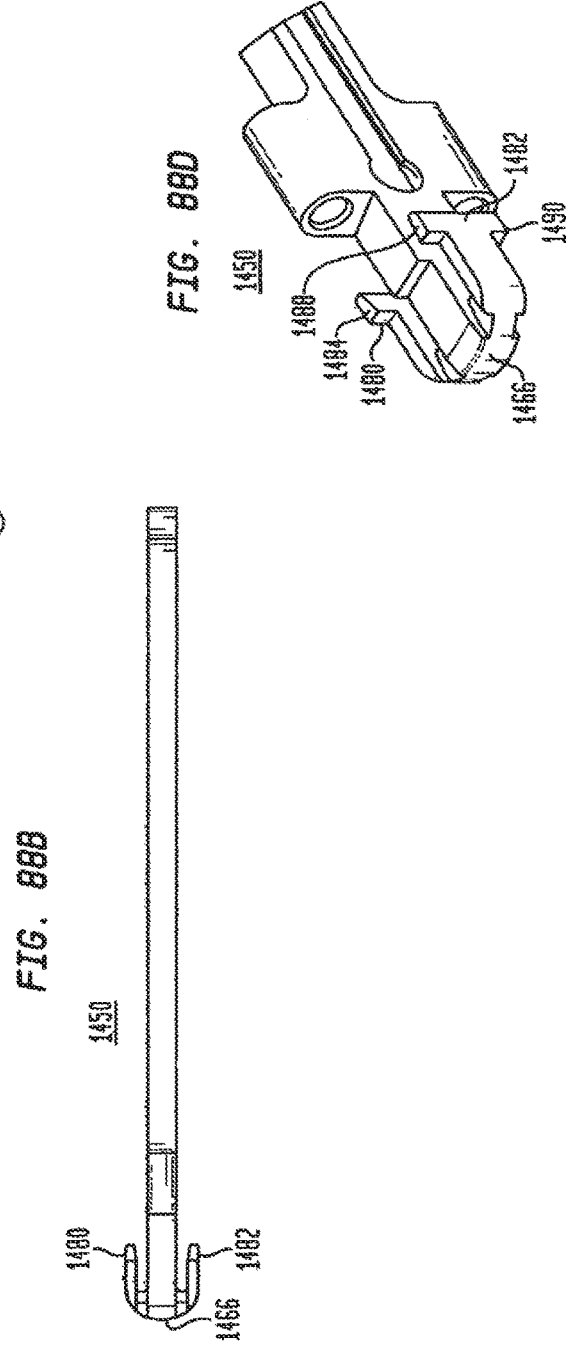

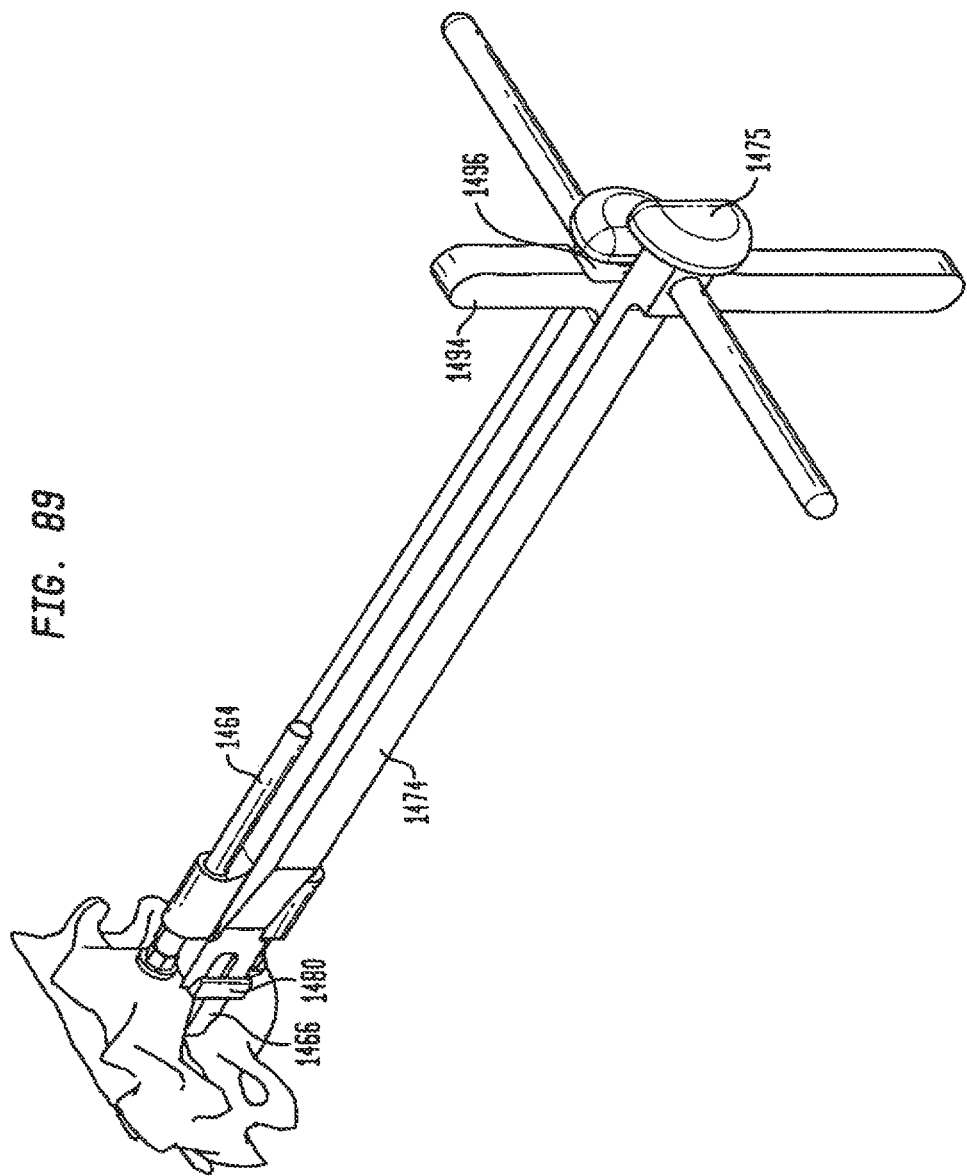

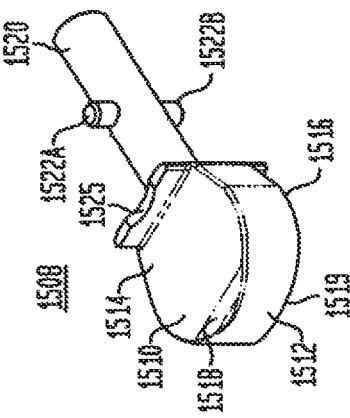
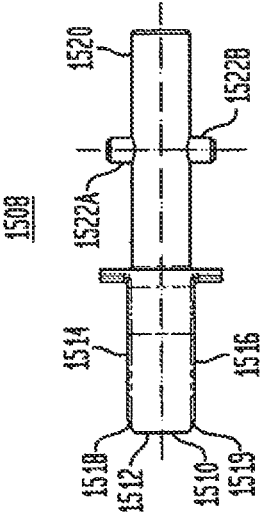
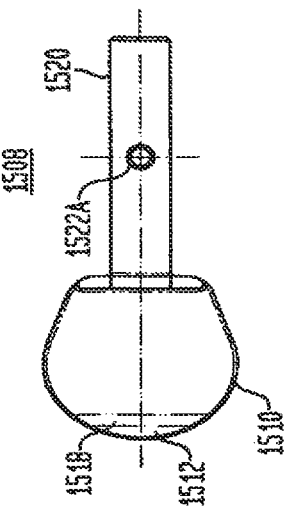
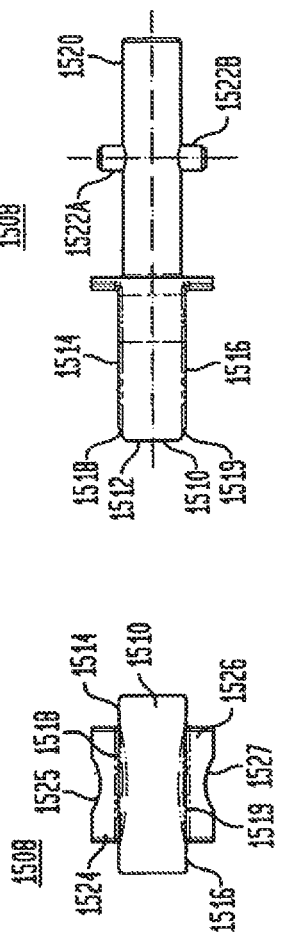

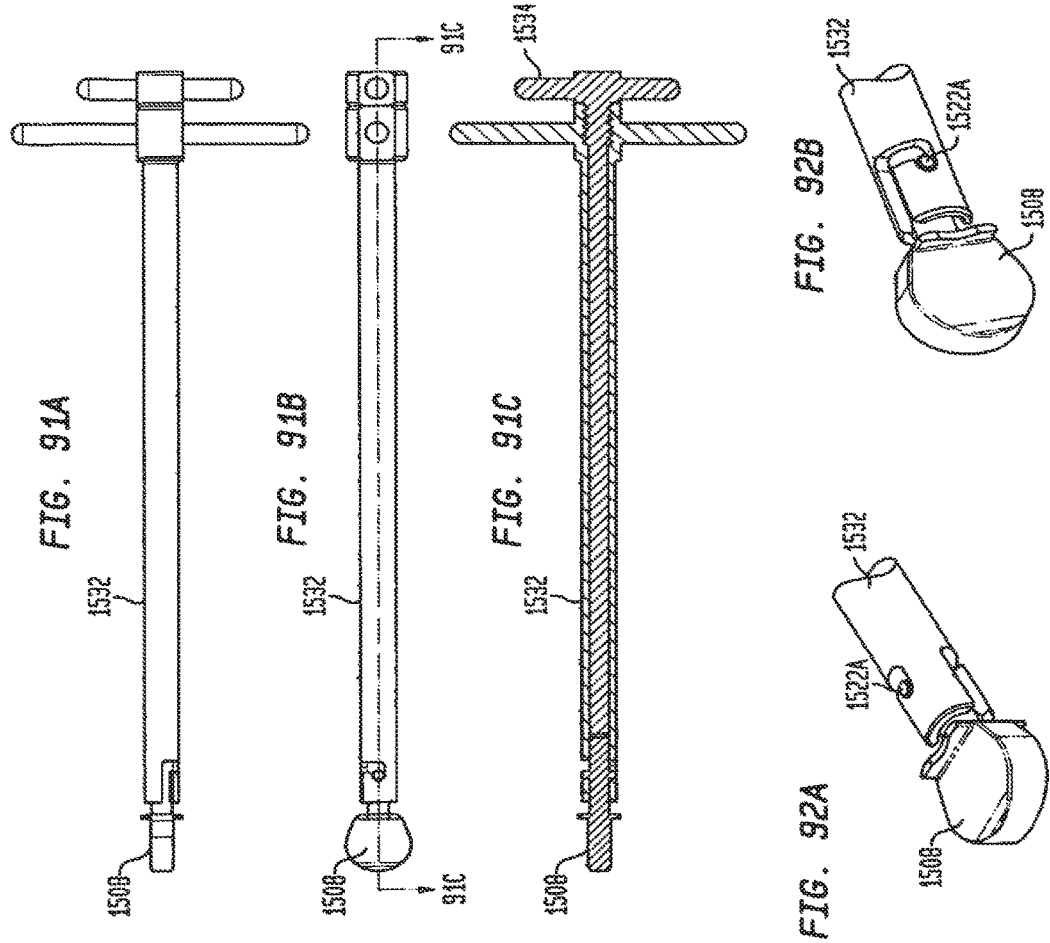

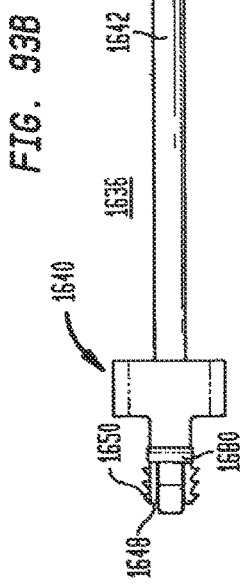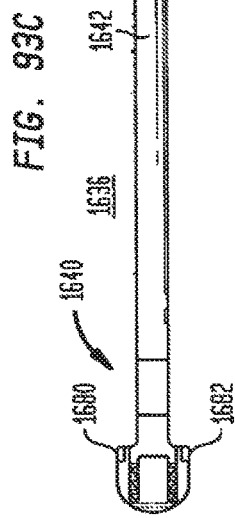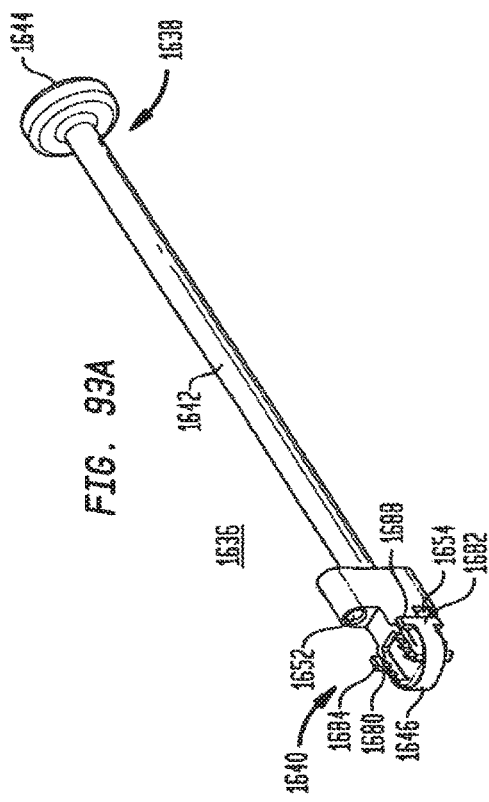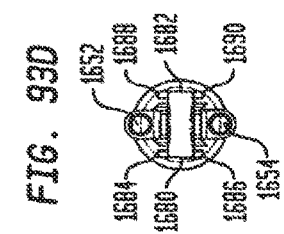

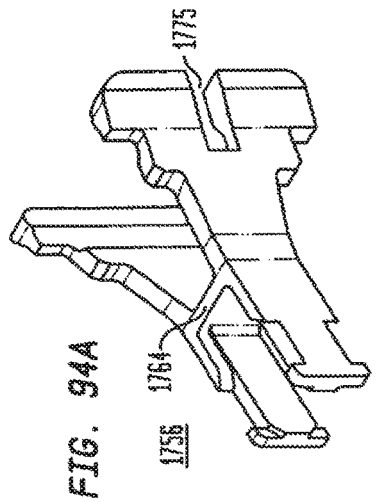
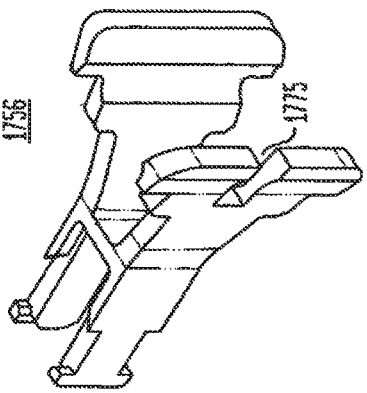
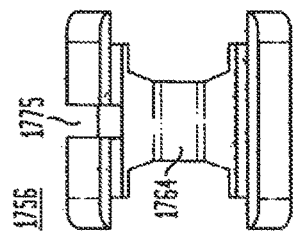
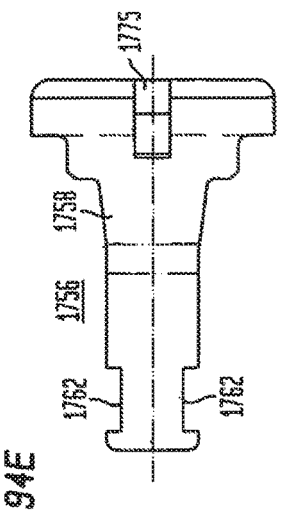
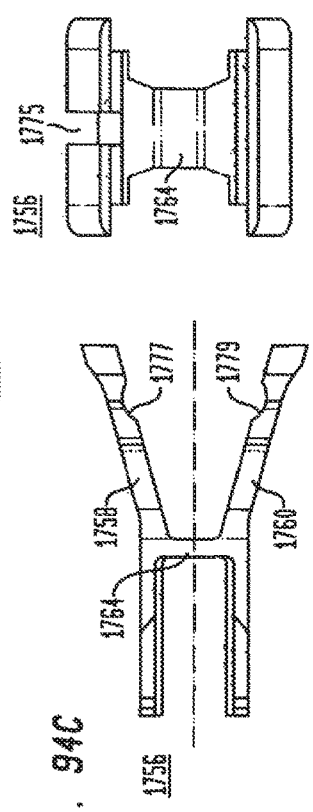
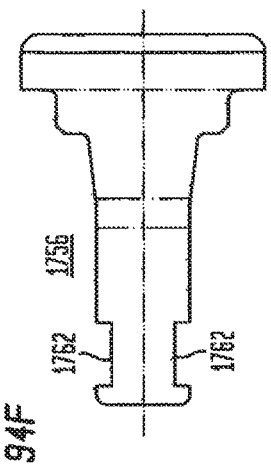

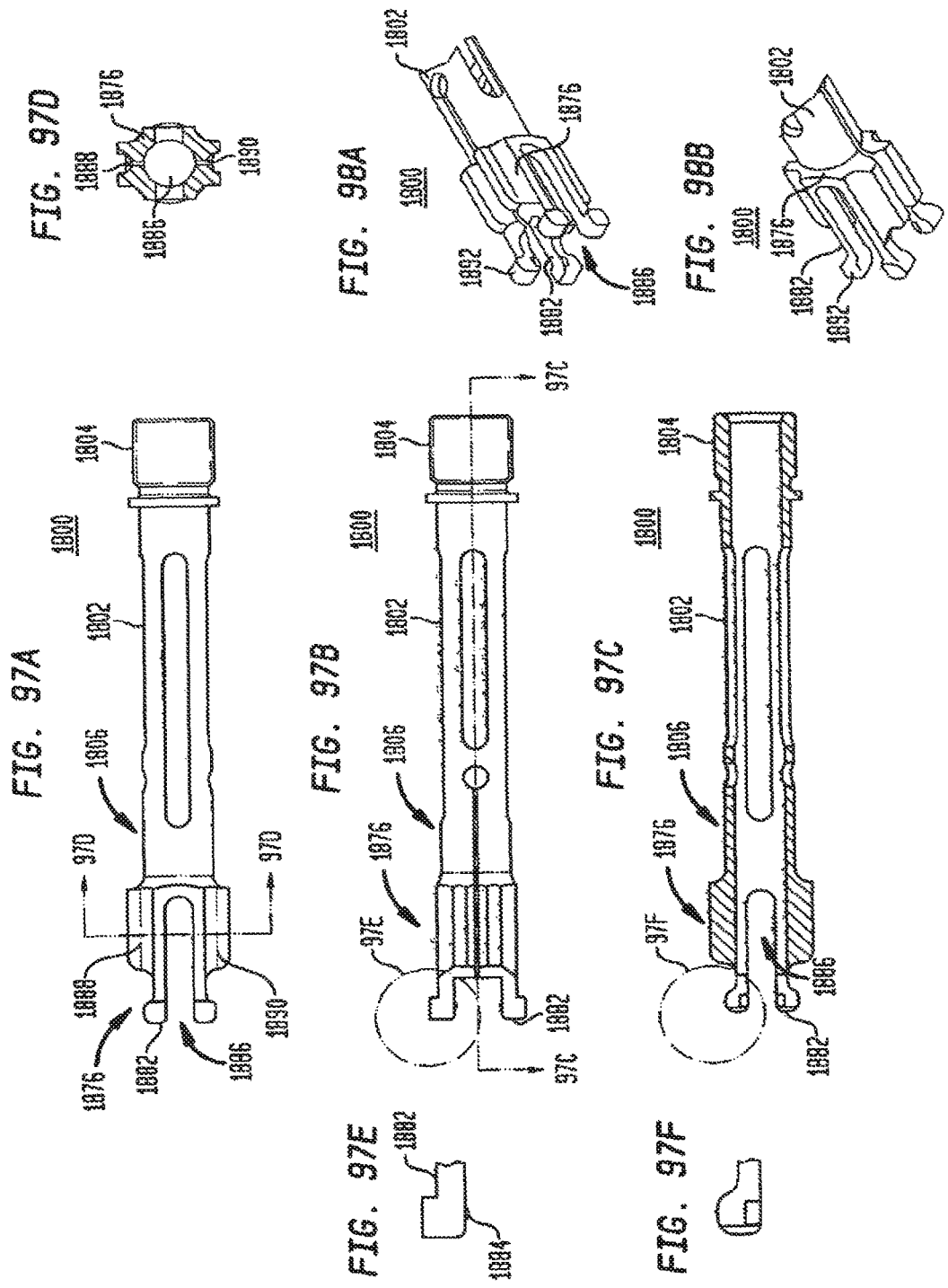

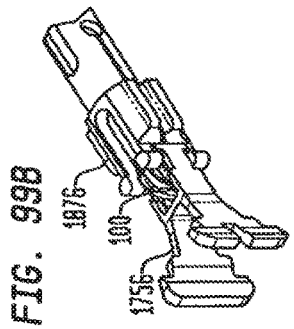
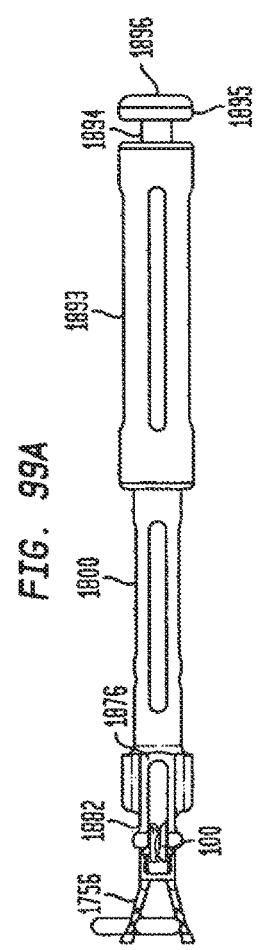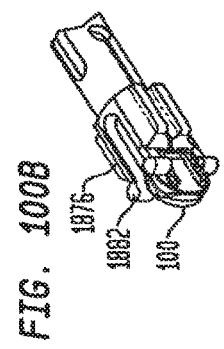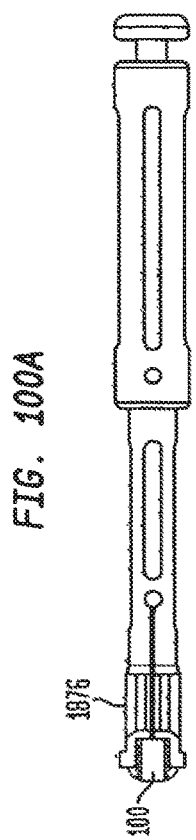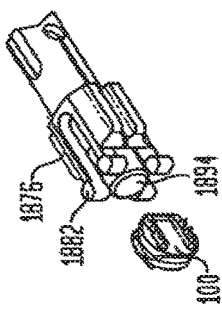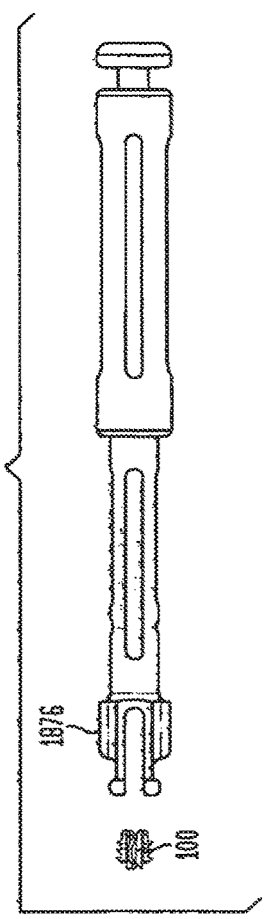

INSTRUMENTS AND METHODS FOR INSERTING ARTIFICIAL INTERVERTEBRAL IMPLANTS

CROSS-REFERENCE TO RELATED APPLICATIONS

This application is a continuation of U.S. application Ser. No. 14/051,086, filed Oct. 10, 2013, which is a divisional of U.S. application Ser. No. 12/321,373, filed Jan. 16, 2009, now issued as U.S. Pat. No. 8,579,911, which claims the benefit of the filing date of U.S. Provisional Patent Application No. 61/011,554, filed Jan. 18, 2008, the disclosures of which are hereby incorporated herein by reference.

The present application is related to U.S. patent application Ser. No. 11/439,808, entitled "Intervertebral Disc and Insertion Methods Therefor," filed May 24, 2006, which claims the benefit of the filing dates of U.S. Provisional Patent Application No. 60/790,415, filed Apr. 7, 2006, 60/721,053, filed Sep. 27, 2005, 60/701,306, filed Jul. 21, 2005 and 60/685,295, filed May 27, 2005, the disclosures of which are hereby incorporated by reference herein.

The present application also relates to U.S. Pat. No. 6,908,484, entitled "Cervical Disc Replacement" and filed on Mar. 6, 2003; U.S. Pat. No. 6,994,728, entitled "Cervical Disc Replacement Method" and filed on Feb. 11, 2004; United States Patent Application Publication No. 2004/0176851, entitled "Cervical Disc Replacement" and filed on Feb. 11, 2004; U.S. Pat. No. 6,994,729, entitled "Cervical Disc Replacement" and filed on Feb. 11, 2004; U.S. Pat. No. 6,997,955, entitled "Cervical Disc Replacement" and filed on Feb. 11, 2004; U.S. Pat. No. 6,972,037, entitled "Cervical Disc Replacement" and filed on Feb. 11, 2004; U.S. Pat. No. 6,972,038, entitled "Cervical Disc Replacement" and filed on Feb. 11, 2004; U.S. Pat. No. 6,997,954, entitled "Cervical Disc Replacement Method" and filed on Feb. 11, 2004; United States Patent Application Publication No. 2005/0240272, entitled "Cervical Disc Replacement" and filed on May 9, 2005; United States Patent Application Publication No. 2005/0240271, entitled "Cervical Disc Replacement" and filed on May 9, 2005; United States Patent Application Publication No. 2005/0240270, entitled "Cervical Disc Replacement" and filed on May 9, 2005; U.S. Pat. No. 6,896,676, entitled "Instrumentation And Methods For Use In Implanting A Cervical Disc Replacement Device" and filed on Oct. 17, 2003; United States Patent Application Publication No. 2004/0176773, entitled "Instrumentation And Methods For Use In Implanting A Cervical Disc Replacement Device" and filed on Feb. 18, 2004; United States Patent Application Publication No. 2004/0176843, entitled "Instrumentation And Methods For Use In Implanting A Cervical Disc Replacement Device" and filed on Feb. 18, 2004; United States Patent Application Publication No. 2004/0176778, entitled "Instrumentation And Methods For Use In Implanting A Cervical Disc Replacement Device" and filed on Feb. 18, 2004; United States Patent Application Publication No. 2004/0176777, entitled "Instrumentation And Methods For Use In Implanting A Cervical Disc Replacement Device" and filed on Feb. 18, 2004; United States Patent Application Publication No. 2004/0176852, entitled "Instrumentation And Methods For Use In Implanting A Cervical Disc Replacement Device" and filed on Feb. 18, 2004; United States Patent Application Publication No. 2004/0176774, entitled "Instrumentation And Methods For Use In Implanting A Cervical Disc Replacement Device" and filed on Feb. 18, 2004; United States Patent Application Publication No. 2004/0176772, entitled "Instrumentation And Methods For Use In Implanting A Cervical Disc Replacement Device" and filed on Feb. 18, 2004; United States Patent Application Publication No. 2004/0220590, entitled "Instrumentation And Methods For Use In Implanting A Cervical Disc Replacement Device" and filed on Feb. 18, 2004; United States Patent Application Publication No. 2005/0071013, entitled "Instrumentation And Methods For Use In Implanting A Cervical Disc Replacement Device" and filed on Nov. 19, 2004; and United States Patent Application Publication No. 2004/0193272, entitled "Instrumentation And Methods For Use In Implanting A Cervical Disc Replacement Device" and filed on Feb. 19, 2004, the disclosures of which are hereby incorporated by reference herein.

The present application also relates to U.S. Pat. No. 6,607,559, entitled "Trial Intervertebral Distraction Spacers" and filed on Jul. 16, 2001; U.S. patent application Ser. No. 10/436,039, entitled "Trial Intervertebral Spacers" and filed May 12, 2003; U.S. patent Ser. No. 10/128,619, entitled "Intervertebral Spacer Having A Flexible Wire Mesh Vertebral Body Contact Element" and filed Apr. 23, 2002; U.S. patent application Ser. No. 11/073,987, entitled Intervertebral Spacer Having A Flexible Wire Mesh Vertebral Body Contact Element; U.S. patent application Ser. No. 10/140,153, entitled "Artificial Intervertebral Disc Having A Flexible Wire Mesh Vertebral Body Contact Element" and filed May 7, 2002; U.S. patent application Ser. No. 10/151,280, entitled "Tension Bearing Artificial Disc Providing A Centroid Of Motion Centrally Located Within An Intervertebral Space" and filed May 20, 2002; U.S. patent application Ser. No. 10/175,417, entitled "Artificial Intervertebral Disc Utilizing A Ball Joint Coupling" and filed Jun. 19, 2002; U.S. patent application Ser. No. 10/256,160, entitled "Artificial Intervertebral Disc" and filed Sep. 26, 2002; U.S. patent application Ser. No. 10/294,983, entitled "Artificial Intervertebral Disc Having A Captured Ball And Socket Joint With A Solid Ball And Retaining Cap" and filed Nov. 14, 2002; U.S. patent application Ser. No. 10/294,982, entitled "Artificial Intervertebral Disc" and filed Nov. 14, 2002; U.S. patent application Ser. No. 10/294,981, entitled "Artificial Intervertebral Disc Having A Captured Ball And Socket Joint With A Solid Ball And Compression Locking Post" and filed Nov. 14, 2002; U.S. patent application Ser. No. 10/642,523, entitled "Axially Compressible Artificial Intervertebral Disc Having Limited Rotation Using A Captured Ball and Socket" and filed Aug. 15, 2003; U.S. patent application Ser. No. 10/642,522, entitled Artificial Intervertebral Disc Having A Circumferentially Buried Wire Mesh Endplate Attachment Device and filed Aug. 15, 2003; U.S. patent application Ser. No. 11/073,987, entitled "Intervertebral Spacer Device Having A Circumferentially Buried Wire Mesh Endplate Attachment Device" and filed Aug. 15, 2003; U.S. patent application Ser. No. 10/642,526, entitled "Circumferentially Buried Wired Mesh Endplate Attachment Device For Use With An Orthopedic Device" and filed Aug. 15, 2003; U.S. patent application Ser. No. 10/294,984, entitled "Artificial Intervertebral Disc Having Limited Rotation Using A Captured Ball And Socket Joint With A Retaining Cap And A Solid Ball Having A Protrusion" and filed Nov. 14, 2002; U.S. patent application Ser. No. 10/294,985, entitled "Artificial Intervertebral Disc Having Limited Rotation Using A Captured Ball and Socket Joint With A Compression" and filed Ser. No. 10/294,985; U.S. patent application Ser. No. 10/294,980, entitled "Artificial Intervertebral Disc Having Limited Rotation Using A Captured Ball And Socket Joint With A Solid Ball, A Retaining Cap, And An Interference Pin" and filed Nov. 14, 2002; U.S. patent application Ser.

No. 10/294,986, entitled "Artificial Intervertebral Disc Having Limited Rotation Using A Captured Ball and Socket Joint With A Solid Ball, A Compression Locking Post, And An Interference Pin" and filed Nov. 14, 2002; U.S. patent application Ser. No. 10/282,356, entitled "Artificial Intervertebral Disc" and filed Sep. 26, 2002; U.S. patent application Ser. No. 10/784,646, entitled Artificial Intervertebral Disc Trial Having A Controllably Separable Distal End" and filed Feb. 23, 2004; U.S. patent application Ser. No. 10/309,585, entitled "Static Trials And Related Instruments and Methods For Use In Implanting An Artificial Intervertebral Disc" and filed Dec. 4, 2002; U.S. patent application Ser. No. 10/784,637, entitled "Instrumentation For Properly Seating An Artificial Disc In An Intervertebral Space" and filed Feb. 23, 2004; U.S. patent application Ser. No. 10/783,153, entitled "Parallel Distractor And Related Methods For Use In Implanting An Artificial Intervertebral Disc" and filed Feb. 20, 2004, the disclosures of which are hereby incorporated by reference herein.

BACKGROUND OF THE INVENTION

The present invention is directed to a spinal joint replacement implant and more particularly to a cervical intervertebral disc implant having saddle shaped articulating surfaces and to methods of inserting the cervical intervertebral disc implant.

As is well known to those skilled in the art, the structure of the intervertebral disc disposed between the cervical bones in the human spine comprises a peripheral fibrous shroud (the annulus) which circumscribes a spheroid of flexibly deformable material (the nucleus). The nucleus comprises a hydrophilic, elastomeric cartilaginous substance that cushions and supports the separation between the bones while also permitting articulation of the two vertebral bones relative to one another to the extent such articulation is allowed by the other soft tissue and bony structures surrounding the disc. The additional bony structures that define pathways of motion in various modes include the posterior joints (the facets) and the lateral intervertebral joints (the unco-vertebral joints). Soft tissue components, such as ligaments and tendons, constrain the overall segmental motion as well.

Traumatic, genetic, and long term wearing phenomena contribute to the degeneration of the nucleus in the human spine. This degeneration of this critical disc material, from the hydrated, elastomeric material that supports the separation and flexibility of the vertebral bones, to a flattened and inflexible state, has profound effects on the mobility (instability and limited ranges of appropriate motion) of the segment, and can cause significant pain to the individual suffering from the condition. Although the specific causes of pain in patients suffering from degenerative disc disease of the cervical spine have not been definitively established, it has been recognized that pain may be the result of neurological implications (nerve fibers being compressed) and/or the subsequent degeneration of the surrounding tissues (the arthritic degeneration of the facet joints) as a result of their being overloaded.

Traditionally, the treatment of choice for physicians caring for patients who suffer from significant degeneration of the cervical intervertebral disc is to remove some, or all, of the damaged disc. In instances in which a sufficient portion of the intervertebral disc material is removed, or in which much of the necessary spacing between the vertebrae has been lost (significant subsidence), restoration of the intervertebral separation is required.

Unfortunately, until the advent of spine arthroplasty devices, the only methods known to surgeons to maintain the necessary disc height necessitated the immobilization of the segment. Immobilization is generally achieved by attaching metal plates to the anterior or posterior elements of the cervical spine, and the insertion of some osteoconductive material (autograft, allograft, or other porous material) between the adjacent vertebrae of the segment. This immobilization and insertion of osteoconductive material has been utilized in pursuit of a fusion of the bones, which is a procedure carried out on tens of thousands of pain suffering patients per year.

This sacrifice of mobility at the immobilized, or fused, segment, however, is not without consequences. It was traditionally held that the patient's surrounding joint segments would accommodate any additional articulation demanded of them during normal motion by virtue of the fused segment's immobility. While this is true over the short-term (provided only one, or at most two, segments have been fused), the effects of this increased range of articulation demanded of these adjacent segments has recently become a concern. Specifically, an increase in the frequency of returning patients who suffer from degeneration at adjacent levels has been reported.

Whether this increase in adjacent level deterioration is truly associated with rigid fusion, or if it is simply a matter of the individual patient's predisposition to degeneration is unknown. Either way, however, it is clear that a progressive fusion of a long sequence of vertebrae is undesirable from the perspective of the patient's quality of life as well as from the perspective of pushing a patient to undergo multiple operative procedures.

While spine arthroplasty has been developing in theory over the past several decades, and has even seen a number of early attempts in the lumbar spine show promising results, it is only recently that arthroplasty of the spine has become a truly realizable promise. The field of spine arthroplasty has several classes of devices. The most popular among these are: (a) the nucleus replacements, which are characterized by a flexible container filled with an elastomeric material that can mimic the healthy nucleus; and (b) the total disc replacements, which are designed with rigid baseplates that house a mechanical articulating structure that attempts to mimic and promote the healthy segmental motion.

Among these solutions, the total disc replacements have begun to be regarded as the most probable long-term treatments for patients having moderate to severe lumbar disc degeneration. In the cervical spine, it is likely that these mechanical solutions will also become the treatment of choice. At present, there are two devices being tested clinically in humans for the indication of cervical disc degeneration. The first of these is the Bryan disc, disclosed in part in U.S. Pat. No. 6,001,130. The Bryan disc is comprised of a resilient nucleus body disposed in between concaval-covex upper and lower elements that retain the nucleus between adjacent vertebral bodies in the spine. The concaval-convex elements are L-shaped supports that have anterior wings that accept bones screws for securing to the adjacent vertebral bodies.

The second of these devices being clinically tested is the Bristol disc, disclosed substantially in U.S. Pat. No. 6,113,637. The Bristol disc is comprised of two L-shaped elements, with corresponding ones of the legs of each element being interposed between the vertebrae and in opposition to one another. The other of the two legs are disposed outside of the intervertebral space and include screw holes through which the elements may be secured to the corresponding vertebra; the superior element being secured to the upper vertebral body and the inferior element being attached to the lower vertebral body. The opposing portions of each of the elements comprise the articulating surfaces that include an elliptical channel formed in the lower element and a convex hemispherical structure disposed in the channel.

As is evident from the above descriptions, the centers of rotation for both of these devices, which are being clinically tested in human subjects, is disposed at some point in the disc space. More particularly with respect to the Bryan disc, the center of rotation is maintained at a central portion of the nucleus, and hence in the center of the disc space. The Bristol disc, as a function of its elongated channel (its elongated axis being oriented along the anterior to posterior direction), has a moving center of rotation which is at all times maintained within the disc space at the rotational center of the hemispherical ball (near the top of the upper element).

Thus, there remains a need for improved intervertebral discs, as well as new and improved methods for safely and efficiently implanting intervertebral discs.

BRIEF SUMMARY OF THE INVENTION

Disclosed herein are intervertebral discs or implants, surgical instruments and procedures in accordance with certain preferred embodiments of the present invention. It is contemplated, however, that the implants, instruments and procedures may be slightly modified, and/or used in whole or in part and with or without other instruments or procedures, and still fall within the scope of the present invention. Although the present invention may discuss a series of steps in a procedure, the steps can be accomplished in a different order, or be used individually, or in subgroupings of any order, or in conjunction with other methods, without deviating from the scope of the invention.

In certain preferred embodiments of the present invention, a method of inserting an intervertebral disc into a disc space includes accessing a spinal segment having a first vertebral body, a second vertebral body and a disc space between the first and second vertebral bodies, securing a first pin to the first vertebral body and a second pin to the second vertebral body, and using the first and second pins for distracting the disc space. The method preferably includes providing an inserter holding the intervertebral disc, engaging the inserter with the first and second pins, and advancing at least a portion of the inserter toward the disc space for inserting the intervertebral disc into the disc space, wherein the first and second pins align and guide the inserter toward the disc space.

In certain preferred embodiments, the inserter desirably includes an inserter head having an upper channel and a lower channel. During the advancing step, the first pin is preferably in contact with the upper channel and the second pin is preferably in contact with the lower channel. The channels may taper inwardly toward one another for urging the first and second pins away from one another as the inserter advances toward the disc space (preferably to more fully open the disc space as the inserter advances toward the disc space). In certain preferred embodiments, the inserter head has a distal end adapted to contact vertebral bone and a proximal end, and the upper and lower channels taper inwardly toward one another between the proximal and distal ends of the inserter head. As a result, the channels are closer together near the distal end of the inserter than near the proximal end of the inserter. In preferred embodiments, the inserter head includes distally extending arms for securing an intervertebral disc implant. Each of the distally extending arms may include an inwardly extending projection engageable with the intervertebral disc implant.

In other preferred embodiments of the present invention, a method of inserting an intervertebral disc implant into a disc space includes accessing a spinal segment having a first vertebral body, a second vertebral body and a disc space between the first and second vertebral bodies, securing a first pin to the first vertebral body and a second pin to the second vertebral body, and using the first and second pins for distracting the disc space. The method may include engaging a chisel guide having a distal head with the first and second pins, and advancing the chisel guide toward the disc space for inserting the distal head of the chisel guide into the disc space, whereby the first and second pins align and guide the chisel guide as the chisel guide advances toward the disc space. The method may also include coupling a chisel having one or more cutting blades with the chisel guide and advancing the one or more cutting blades toward the first and second vertebral bodies for forming channels in one or more endplates of the first and second vertebral bodies. The distal head of the chisel guide preferably has a top surface with at least one groove formed therein for guiding the one or more chisel blades toward the disc space. The bottom surface of the head may also have at least one groove for guiding the chisel.

The method may also include providing an inserter holding an intervertebral disc implant, and after forming channels in the one or more endplates of the first and second vertebral bodies, disengaging the chisel guide from the first and second pins and engaging the inserter with the first and second pins. The inserter is preferably advanced toward the disc space for inserting the intervertebral disc implant into the disc space, whereby the first and second pins align and guide the inserter as the inserter advances toward the disc space.

In other preferred embodiments of the present invention, a kit includes a plurality of two-part intervertebral disc implants having different sizes, and a plurality of implant dispensers, each implant dispenser holding together the two parts of one of the two-part intervertebral disc implants so that it can be manipulated as a single implantable unit. Each implant dispenser preferably has indicia corresponding to the size of the intervertebral disc implant held by the implant dispenser. The indicia on the implant dispenser may include a color code or text indicating the size of the intervertebral disc implant held by the implant dispenser.

In particular preferred embodiments, each intervertebral disc implant has a top element including a bone engaging surface and an articulating surface and a bottom element including a bone engaging surface and an articulating surface. The implant dispenser desirably holds the articulating surfaces of the top and bottom elements in contact with one another.

The implant dispensers may be flexible. In preferred embodiments, an implant dispenser includes a first arm engaging a top element of the intervertebral disc implant, a second arm engaging a bottom element of the intervertebral disc implant, and a connecting element for interconnecting the first and second arms. The connecting element is preferably flexible for enabling the first and second arms to move away from one another for releasing the intervertebral disc.

The kit may also include a plurality of inserters, the inserters being adapted to couple with the intervertebral disc implants while the intervertebral disc implants are held in the implant dispensers, so that the intervertebral disc implants can be transferred from the implant dispensers to the inserters. Each inserter preferably has indicia corresponding to the size of a corresponding one of the intervertebral disc implants. The indicia on the inserter may include a color code or text. The intervertebral disc implants are preferably transferable from the implant dispensers to the inserters while being maintained as a single implantable unit. In certain preferred embodiments, an implant inserter will couple directly to the intervertebral disc implant while the disc implant is held by an implant dispenser.

In other preferred embodiments of the present invention, a template for marking score lines on a spinal segment includes a shaft having a proximal end and a distal end, and a template marker provided at the distal end of the shaft. The template marker preferably includes a cruciform-shaped structure having a first vertical arm and a second vertical arm that extends away from the first arm, the first and second vertical arms being aligned with one another along a first axis. The cruciform-shaped structure also preferably includes a first lateral arm and a second lateral arm extending away from the first lateral arm, the first and second lateral arms being aligned with one another along a second axis, whereby distal surfaces of the first and second lateral arms form a concave curved surface that conforms to an anterior surface of a disc between superior and inferior vertebral bodies.

The template may include a central pin or a plurality of pins provided at the distal ends of the lateral arms for being inserted into the natural disc for stabilizing the template adjacent the disc space, and the vertical arms and the lateral arms spread outwardly from the distal end of the shaft. The first vertical arm desirably includes a first distally extending tack for engaging an anterior surface of the first vertebral body and the second vertical arm desirably includes a second distally extending tack for engaging an anterior surface of the second vertebral body.

In an alternative embodiment, instead of or in addition to a template, the present invention may include a midline marker. The midline marker is preferably used for determining a midline of a disc space between two vertebrae. The midline marker preferably has a cruciform shape with a first vertical extension, a second vertical extension, a first lateral extension, and a second lateral extension. The midline marker also preferably has a leading face and a trailing face. The leading face may have a concave curved surface that extends between the first and second lateral arms. The first lateral arm preferably has a first barbed spike projecting therefrom, and the second lateral arm preferably has a second barbed spike projecting therefrom. The midline marker also may include a button projecting from the rear surface thereof, which is connected to the midline marker via connector segment. This button may facilitate connection of the midline marker to a handle.

In certain preferred embodiments of the present invention, each of the top and bottom elements of the implant has an anterior wall that preferably connects the anterior ends of the protrusions on the element. The anterior wall preferably serves as a vertebral body stop to prevent over-insertion of the implant and/or posterior migration of the implant. The anterior wall preferably serves as an engageable feature for engagement with instruments, including but not limited to tamps, extraction or repositioning instruments. The anterior wall in some embodiments may have a curved posterior face to sit flush against a curved anterior endplate face. At least the posterior surface of the wall may be coated with an osteoconductive material to facilitate long-term fixation to the endplate surface.

In certain preferred embodiments of the present invention, the intervertebral disc implants includes a top element and a bottom element. Each implant part may have protrusions with outwardly laterally facing surfaces. One or more of the outwardly laterally facing surfaces may have a vertically extending channel, or groove, or depression, or like feature for engagement with instruments, including but not limited to insertion, extraction or repositioning instruments. Preferably, the surface of this feature can be coated with an osteoconductive material to facilitate long-term fixation to the endplate bone.

In certain preferred embodiments, the intervertebral disc implant, or the instruments, may alternatively or additionally incorporate any or all of the features discussed previously, disclosed herein, or discussed in U.S. patents and/or patent applications incorporated by reference herein. Preferably, the configuration of the bearing surfaces of the intervertebral disc implant in this preferred embodiment may be substantially similar to those of the other bearing surface configurations discussed previously, disclosed herein, or incorporated by reference herein.

Prior to insertion of the intervertebral disc implant disclosed herein, a surgeon preferably performs a cervical anterior exposure and initial natural disc removal (e.g., discectomy). After simple exposure and initial natural disc removal, the surgeon may introduce a guide, such as a reference pin drill guide that enables the surgeon to anchor a pair of alignment or reference pins (e.g., Caspar pins) into the adjacent vertebral bones, preferably along the midline of the bones, and at predetermined vertical distances from the endplate edges.

The present application discloses the use of reference or alignment pins for properly aligning tooling and/or implants with bone. The reference or alignment pins shown herein are merely representative examples of certain preferred embodiments of the present invention. It is contemplated that other reference or alignment tools and techniques may be used for properly aligning tools and/or implants with bone, and that these other reference or alignment tools and techniques are within the scope of the present invention.

With the reference pins in place, the surgeon may apply distraction to the disc space by using a distraction tool, such as a standard Caspar distractor, and then complete the discectomy and distraction. Once the disc space is cleared and restored to a desired height, the surgeon may choose to remove the distraction tools and advance a guide, such as a burr or drill guide along the reference pins and into the disc space. The burr or drill guide preferably engages the reference pins as the burr/drill guide is advanced toward the disc space. Thus, the reference pins serve to provide proper alignment of the burr/drill guide relative to the disc space. In certain preferred embodiments, the burr/drill guide includes a distal head that fits within the disc space. The burr/drill guide preferably permits the surgeon to introduce a burr or drill bit through each of four holes in the guide and burr or drill pilot grooves or holes at predetermined locations in the endplates. As will be described in more detail below, the pilot grooves are used to form protrusion channels for the protrusions of the intervertebral disc.

In certain preferred embodiments of the present invention, in order to cut protrusion channels in the endplates, a chisel guide may be utilized. The chisel guide preferably includes a distal head that is insertable into the disc space. The distal head preferably has grooves formed in top and bottom surfaces of the distal head for guiding a chisel for cutting protrusion channels. The chisel guide preferably has alignment openings for sliding over the reference pins. The reference pins preferably align and direct the chisel guide into the disc space. Chisels may then be advanced along the sides of the chisel guide for cutting the protrusion channels. In certain preferred embodiments of the present invention, a first pair of chisels (e.g., roughening chisels) is advanced along the sides of chisel guide to cut channels. Preferably, the first pair of chisels cuts channels that are approximately 1 mm wide. A second pair of larger chisels (e.g., finishing chisels) can be used to widen the protrusion channels, preferably to about 2 mm. In other preferred embodiments of the present invention, a first pair of chisels is approximately 1 mm wide and 1.5 mm high, and a second pair of chisels (e.g., the finishing chisels) are 1.5 mm wide and 2.5 mm high.

Once the protrusion channels have been cut, the implant may be mounted to an insertion tool (e.g., to the distal tip of an insertion tool) and inserted into the disc space. The insertion tool preferably includes upper and lower guide slots or openings that permit the insertion tool to slide along the reference pins. The guide slots are preferably ramped so that the disc space is distracted (to preferably approximately 2 mm wider than the height of the implant) to ensure easy insertion of the implant. In other preferred embodiments, the reference pins may also be engaged by a distraction tool to distract the disc space during insertion, e.g., if such distraction is necessary. This additional distraction may ensure that the device is implanted easily without requiring excessive impacting.

Once the intervertebral disc implant has been inserted into the disc space, a tamping instrument may be used to adjust the final position of the disc components relative to one another and/or relative to the vertebral bones. Should the surgeon want to remove the device intra-operatively, or in the case of a revision, a proximal feature of the device (e.g., an anterior wall) may be engaged by an instrument (e.g., an extraction instrument) to pull the device free from the disc space.

In other preferred procedures, after simple exposure and initial disc removal, the surgeon may introduce a guide, such as a reference pin grill guide, that permits the surgeon to drill guide holes in superior and inferior vertebral bodies (preferably parallel to one another) for the placement of the pair of reference pins. A second guide, such as a sleeve or reference pin driver guide may be used to ensure that the reference pins are placed in the pre-drilled holes so that the pins are parallel, and are driven into the adjacent vertebral bones preferably along the midline of the bones, and at predetermined distances from the endplates.

With the reference pins in place, the surgeon may apply distraction to the disc space, e.g., by means of a distraction tool, and then complete the discectomy and distraction. The surgeon should preferably remove any anterior or posterior osteophytes that may interfere with the ultimate placement of the implant.

It should be noted that features and methods and functionalities of the present invention, including but not limited to features and methods and functionalities for engaging one tool (or parts thereof) with one or more other tools (or parts thereof) or with the implants (or parts thereof), and vice-versa; for addressing, avoiding, manipulating, or engaging the patient's anatomy; for aligning one or more tools with anatomic or non-anatomic reference points; and for aligning the tools and implants with one another and/or a treatment space; are not and should not be limited to those embodied in and achieved by the structures and methods of the specific embodiments described and shown, but rather the structures and methods of the specific embodiments described and shown are merely examples of structures and methods that can achieve certain features and methods and functionalities of the present invention.

One aspect of the present invention includes an assembly for determining the midline of a disc space between two vertebrae. In accordance with one embodiment of this aspect, the assembly includes a handle having an outer shaft and a plunger disposed within the outer shaft, the plunger including an opening formed in one end. The assembly also preferably includes a midline marker having a cruciform-shaped structure and including a first lateral extension having a first barbed spike extending in a first direction, a second lateral extension that extends away from said first lateral extension so that the first and second lateral extension being aligned with one another along a first axis, the second lateral extension including a second barbed spike extending in the first direction, a first vertical extension, a second vertical extension extending away from said first vertical extension, the first and second vertical extensions being aligned with one another along a second axis, and a button extending in second direction opposite the first direction, the button disposed within the opening formed in the plunger.

In accordance with other embodiments of this aspect, the first and second lateral extensions may form a concave curved surface that conforms to an anterior surface of the disc between the superior and inferior vertebral bodies. The first vertical extension may include a first concave recess and the second vertical extension includes a second concave recess, the first and second concave recesses providing an alignment feature for marking the two vertebrae. The plunger may be moveable with respect to the outer shaft. The plunger may be moveable between a first position in which the midline marker is capable of being removed from the handle and a second position in which the midline marker is fixed to the handle. The plunger may be biased to the second position, including, but not limited to, by the inclusion of a spring. The midline marker may be axially fixed with respect to the handle. The outer shaft may include at least one slot and the plunger includes at least one pin disposed within the at least one slot. The outer shaft may include an alignment feature. The first vertical extension may include a first concave recess and the second vertical extension may include a second concave recess, the first and second concave recesses being aligned with the alignment feature and providing an alignment feature for marking the two vertebrae.

Another aspect of the present invention includes a method of marking first and second adjacent vertebral bodies separated by an intervertebral disc. In accordance with one embodiment of this aspect, the method includes the steps of providing a midline marker including a first lateral extension having a first barbed spike direction, a second lateral extension having a second barbed spike, a first vertical extension including a first recess, and a second vertical extension including a second recess, inserting the first and second barbed spikes in the intervertebral disc so that the first recess is aligned with the first vertebral body and the second recess is aligned with the second vertebral body, using the first recess to mark the first vertebral body and the second recess to mark the second vertebral body.

In accordance with other embodiments of this aspect, the first and second lateral extensions may be aligned with one another along a first axis and the first and second vertical extensions may be aligned with one another along a second axis. The inserting step may include placing a concave curved surface formed by the first and second lateral extensions adjacent the intervertebral disc. The method may further include the step of attaching the midline marker to a handle having an outer shaft and plunger disposed within the outer shaft. The step of attaching may include placing a button formed on the midline marker in an opening formed in the plunger. The step of attaching may include moving the plunger to a first position with respect to the outer shaft, the first position allowing for the button to be placed in the opening. The step of attaching may include moving the plunger to a second position with respect to the outer shaft, the second position allowing for the midline marker to be fixed with respect to the handle. The step of attaching may include aligning the first and second recesses with an alignment feature of the handle. The step of inserting may include aligning the alignment feature with respect to the first and second vertebral bodies.

Another aspect of the present invention includes a reference pin drill and insertion guide for use in preparing adjacent first and second vertebral bodies separated by a disc space. In one embodiment of this aspect, the reference pin drill and insertion guide includes a handle, a shaft connected to the handle, and a head connected to the shaft. The head may include a tapered nose capable of being inserted into the disc space, the tapered nose including a top surface and a bottom surface, a first vertebral body stop disposed to a first side of the tapered nose and extending above the top surface and below the bottom surface, a second vertebral body stop disposed to a second side of the tapered nose and extending above the top surface and below the bottom surface, a first protective sheath including a first opening, and a second protective sheath including a second opening. When the tapered nose is inserted into the disc space, the first and second protective sheaths preferably enable reference pin holes to be formed in the first and second vertebral bodies and reference pins to be place in the first and second vertebral bodies.

In other embodiments of this aspect, the shaft may include an elbow so that the handle is located out of alignment with the head, where the elbow may form an angle of one hundred fifty degrees. The first and second vertebral body stops may extend at least two millimeters above the top surface and at least two millimeters below the bottom surface. The first and second vertebral body stops may form at least one concave surface that conforms with the first and second vertebral bodies. The tapered nose may include first and second surfaces formed parallel to each other and third and fourth surfaces formed non-parallel to each other. A stepped drill may be inserted into the first or second protective sheath. The first protective sheath may include a first slot and the second protective sheath may include a second slot.

Yet another aspect of the present invention is an implant dispenser for holding the top and bottom elements of an intervertebral disc implant. In accordance with one embodiment of this aspect, the dispenser includes a superior arm for engaging the top element of the intervertebral disc implant, an inferior arm for engaging the bottom element of the intervertebral disc implant, a central support connecting the superior and inferior arms, the central support allowing for the superior and inferior arms to flex relative to one another, and a clip inserted between the superior and inferior arms to prevent the superior and inferior arms from moving towards one another.

In other embodiments of this aspect, the superior and inferior arms may include lateral notches for receiving teeth of the top and bottom element of the intervertebral disc implant. The superior arm may include a slot and a first notch and the inferior arm may include a second notch. The clip may include a main body having an upper end and a lower end, the upper end disposed within the first notch and the lower end disposed within the second notch. The clip may include a projection extending from the main body, the projection disposed within the slot of the superior arm.

Yet another aspect of the present invention is an insertion tool for inserting an intervertebral disc implant. In one embodiment of this aspect the insertion tool an inserter body having a first slot and an inserter head integrally connected with the inserter body. The inserter head includes a second slot, a first arm including a first inwardly facing surface having a first projection extending therefrom and a first vertebral body stop, the first projection adapted to engage a first depression of the intervertebral disc implant, a second arm including a second inwardly facing surface having a second projection extending therefrom and a second vertebral body stop, the second projection adapted to engage a second depression of the intervertebral disc implant, an upper alignment groove, and a lower alignment groove. The first and second slots form a first continuous slot.

In other embodiments of this aspect, the insertion tool may further include a third arm and a fourth arm. The third arm may include a third projection adapted to engage a third depression of the intervertebral disc implant, and the fourth arm may include a fourth projection adapted to engage a fourth depression of the intervertebral disc implant. The inserter body may include a third slot and the inserter head includes a fourth slot, the third and fourth slots forming a second continuous slot. The first and second arms may be capable of moving with respect to each other and the third and fourth arms may be capable of moving with respect to each other. The first continuous slot may be in communication with a first aperture and the second continuous slot may be in communication with a second aperture. The first and second alignment grooves may be tapered with respect to each other. The insertion tool may further include an insertion tool handle, where the insertion tool handle includes a plunger rod extending therethrough and a knob having a contact surface for moving the plunger rod within the insertion tool handle.

These and other preferred embodiments of the present invention will be described in more detail below.

BRIEF DESCRIPTION OF THE DRAWINGS

FIGS. 2A-2H show a top element of the intervertebral disc implant shown in FIG. 1.

FIGS. 3A-3H show a bottom element of the intervertebral disc implant shown in FIG. 1.

FIGS. 4A-4H show other views of the intervertebral disc implant shown in FIG. 1.

FIG. 5 shows a perspective view of the top and bottom elements of the intervertebral disc implant shown in FIG. 1.

FIGS. 7A-7D show a template, in accordance with certain preferred embodiments of the present invention.

FIGS. 8A-8D show a template marker, in accordance with other preferred embodiments of the present invention.

FIGS. 9A-9B show the template marker of FIG. 8A being attached to a template handle, in accordance with certain preferred embodiments of the present invention.

FIGS. 10A-10D show the template marker and the template handle shown in FIGS. 9A-9B.

FIGS. 11A-11D show a reference pin drill guide, in accordance with certain preferred embodiments of the present invention.

FIG. 12 shows a drill bit used with the reference pin drill guide shown in FIGS. 11A-11D.

FIGS. 13A-13B show the reference pin drill guide of FIGS. 11A-11D inserted into an intervertebral disc space, in accordance with certain preferred embodiments of the present invention.

FIGS. 14A-14C show a reference pin insertion guide, in accordance with certain preferred embodiments of the present invention.

FIGS. 15A-15C show a reference pin, in accordance with certain preferred embodiments of the present invention.

FIG. 16 shows a reference pin, in accordance with another preferred embodiment of the present invention.

FIGS. 17A-17C show a reference pin driver, in accordance with certain preferred embodiments of the present invention.

FIGS. 18A-18B show a sleeve used with the reference pin insertion guide of FIGS. 14A-14C, in accordance with certain preferred embodiments of the present invention.

FIGS. 20A-20D show a drill guide, in accordance with certain preferred embodiments of the present invention.

FIGS. 22A-22D show a chisel used in cooperation with the chisel guide of FIGS. 21A-21D.

FIG. 23 shows the chisel of FIGS. 22A-22D, coupled with the chisel guide of FIGS. 21A-21D.

FIGS. 24A-24B show a mallet, in accordance with certain preferred embodiments of the present invention.

FIGS. 25A-25D show a sizer, in accordance with certain preferred embodiments of the present invention.

FIGS. 26A-26E show the sizer of FIGS. 25A-25D, coupled with a sizer handle, in accordance with certain preferred embodiments of the present invention.

FIGS. 27A-27D show a trial, in accordance with certain preferred embodiments of the present invention.

FIGS. 28A-28F show an implant dispenser, in accordance with certain preferred embodiments of the present invention.

FIGS. 30A-30E-1 show an inserter head for inserting an intervertebral disc into a disc space, in accordance with certain preferred embodiments of the present invention.

FIG. 31 shows the inserter head of FIG. 30A and an exploded view of an inserter handle, in accordance with certain preferred embodiments of the present invention.

FIGS. 32A-32B show the inserter head and inserter handle of FIG. 31 assembled together.

FIGS. 33A-33B show an intervertebral disc implant being transferred from an implant dispenser to an inserter head, in accordance with certain preferred embodiments of the present invention.

FIGS. 34A-34B show an intervertebral disc implant, coupled with an inserter head, in accordance with certain preferred embodiments of the present invention.

FIGS. 35A-35B show an intervertebral disc implant being disengaged from a distal end of an inserter head, in accordance with certain preferred embodiments of the present invention.

FIGS. 36A-36B show a tamp, in accordance with certain preferred embodiments of the present invention.

FIGS. 37A-37D show an extractor, in accordance with certain preferred embodiments of the present invention.

FIG. 83 shows a step drill, in accordance with another preferred embodiment of the present invention.

FIGS. 84A-84B show a reference pin drill guide, in accordance with another preferred embodiment of the present invention.

FIGS. 85A-85B show the step drill of FIG. 83 coupled with the reference pin drill guide of FIGS. 84A-84B.

FIGS. 86A-86B show a method of forming a reference pin opening in a vertebrae using the reference pin drill guide shown in FIGS. 84A-85B.

FIGS. 87A-87D show a fin drill guide, in accordance with certain preferred embodiments of the present invention.

FIGS. 88A-88D show a chisel guide, in accordance with certain preferred embodiments of the present invention.

FIG. 89 shows two chisels coupled with the chisel guide of FIGS. 88A-88D, in accordance with certain preferred embodiments of the present invention.

FIGS. 90A-90D show a sizer for preparing a disc space between opposing vertebrae, in accordance with certain preferred embodiments of the present invention.

FIGS. 91A-91C show the sizer of FIGS. 90A-90D secured to a distal end of an insertion handle.

FIGS. 92A-92B show a perspective views of the sizer of FIGS. 90A-90D secured to the distal end of the insertion handle shown in FIGS. 91A-91C.

FIGS. 93A-93D show a serrated broach used for preparing a disc space, in accordance with certain preferred embodiments of the present invention.

FIGS. 94A-94F show an implant dispenser, in accordance with other preferred embodiments of the present invention.

FIGS. 97A-97C show an inserter body including an inserter head, in accordance with certain preferred embodiments of the present invention.

FIG. 97D shows the inserter head shown in FIG. 97A taken along lines 97D-97D thereof.

FIG. 97E shows a fragmentary view of the distal end of the inserter head shown in FIG. 97B.

FIG. 97F shows a fragmentary view of the distal end of the inserter head shown in FIG. 97C.

FIGS. 98A-98B show perspective views of the inserter head shown in FIGS. 97A-97C.

FIGS. 99A-99B show the implant dispenser and intervertebral disc shown in FIGS. 96A-96E being secured to the inserter head of FIGS. 98A-98B.

FIGS. 100A-100B show the intervertebral disc after it has been secured to the distal end of the inserter head.

FIGS. 101A-101B show the intervertebral disc after being decoupled from the distal end of the inserter head by an advancing plunger, in accordance with certain preferred embodiments of the present invention.

DETAILED DESCRIPTION

Figure 1:
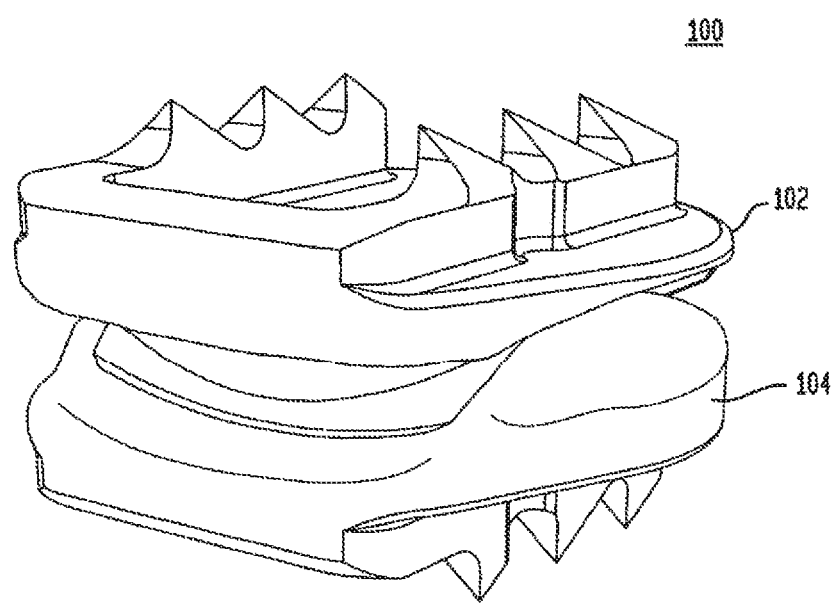
FIG. 1 shows a perspective view of an intervertebral disc implant, in accordance with certain preferred embodiments of the present invention.

Referring to FIG. 1, in certain preferred embodiments of the present invention, an intervertebral disc implant 100 includes a top element 102 and a bottom element 104. As will be described in more detail below, the top and bottom elements 102, 104 have opposing articulating surfaces that engage one another. The intervertebral disc implant is adapted to be inserted into a disc space between adjacent vertebrae.

Referring to FIGS. 2A-2H, the top element 102 includes a first bone engaging surface 106 having protrusions 108A, 108B and a second articulating surface 110. Referring to FIGS. 2C and 2D, the top element has a posterior end 112 and an anterior end 114. As shown in FIGS. 2A and 2C, the two protrusions 108 are interconnected by an anterior wall 116 that extends along the anterior end 114 of the top element. The anterior wall preferably serves as a vertebral body stop to prevent over insertion of the intervertebral disc implant and/or posterior migration of the implant. The anterior wall of the top element 102 preferably provides an engagement surface to be engaged by instruments, including but not limited to tamps and extraction or repositioning instruments. In certain preferred embodiments, the anterior wall may have a curved posterior face adapted to sit flush against a curved anterior face of a vertebral body. In certain preferred embodiments, one or more surfaces of the anterior wall may be coated with an osteoconductive material to facilitate long-term fixation to an endplate surface.

Referring to FIGS. 2E and 2H, the articulating surface 110 preferably defines a convex curve extending between the sides 118, 120 of the top element 102. Referring to FIGS. 2F and 2G, the articulating surface 110 also defines a concave curve or surface extending between the posterior and anterior ends 112, 114 of the top element 102. In certain preferred embodiments, the articulating surface 110 defines a toroidal saddle-shaped surface.

Referring to FIG. 2C, each protrusion 108 preferably has an engagement feature, or depression 121 formed in an outer surface thereof. In certain preferred embodiments, the depressions 121 are vertically extending. In other preferred embodiments, the protrusions may have one or more holes extending at least partially or completely therethrough. The holes may receive or be suitable for receiving a bone-growth inducing material. As will be described in more detail below, the depressions 121 facilitate engagement of the top element with instruments, and specifically preferably facilitate securing and handling of the top element 102 during an intervertebral disc insertion operation. The depressions 121 on the two protrusions 108 are preferably in alignment with one another. In other words, the depressions 121 are preferably at the same distance between the posterior end 112 and the anterior end 114 of the top element 102.

As shown in FIGS. 2A, 2C, and 2F, each protrusion 108 preferably includes teeth 122 having sloping surfaces 124 (e.g., having a low point nearer to the posterior end 112 of the top element 102 and a high point nearer to the anterior end 114 of the top element 102) that facilitate insertion of the posterior end 112 of the top element 102. Referring to FIG. 2F, the sloping surfaces 124 of the teeth 122 facilitate insertion of the implant in a direction indicated by arrow $D_1$. The vertical surfaces 126 of the teeth 122 hinder or prevent dislodgement of the implant in the direction indicated by arrow $D_2$.

Referring to FIG. 2H, the teeth 122 on protrusions 108 preferably also include laterally sloping surfaces 126 that slope downwardly from apexes close to axis $A_1$ to the lateral sides 118, 120 of the top element 102. Thus, the sloping surfaces 126 slope away from axis $A_1$.

Referring to FIGS. 3A-3H, the intervertebral disc implant preferably includes a bottom element 104 having a first bone engaging surface 128 and a second articulating surface 130 that engages the articulating surface 110 of the top element 102 (FIG. 2A). The bottom element 104 includes a posterior end 132, an anterior end 134, and lateral sides 136, 138. Referring to FIGS. 3A and 3C, the first bone engaging surface 128 includes first and second protrusions 140A, 140B. Each protrusion preferably has an engagement feature or depression 142 formed in an outer surface thereof. In certain preferred embodiments, the depressions 142 are vertically extending. In other preferred embodiments, the protrusions may have one or more holes extending at least partially or completely therethrough. The holes may receive or be suitable for receiving a bone-growth inducing material. As will be described in more detail below, the depressions 142 facilitate engagement of the bottom element with instruments, and specifically preferably facilitate securing and handling of the bottom element 104 during an intervertebral disc insertion operation. The depressions 142 on the two protrusions 140A, 140B are preferably in alignment with one another. In other words, the depressions 142 are preferably at the same distance between the posterior end 132 and the anterior end 134 of the bottom element 104. Referring to FIGS. 3F and 3G, each protrusion 140A, 140B preferably also includes teeth 144 having sloping surfaces 146 having a low point nearer to the posterior end 132 of the bottom element 104 and a high point nearer to the anterior end 134 of the bottom element 104. Similar to the sloping surfaces of the teeth of the top element 102 described above, the sloping surfaces 146 on the teeth 144 facilitate insertion of the bottom element 104 in the direction indicated by arrow $D_3$. The vertical surfaces 147 of the teeth 144 hinder or prevent dislodgement of the implant in the direction indicated by arrow $D_4$ (FIG. 3).

Referring to FIGS. 3E and 3H, the teeth 144 preferably also include laterally sloping surfaces 148 that slope downwardly toward axis $A_2$ (FIG. 3H). More specifically, the sloping lateral surfaces have apexes or high points closer to the lateral sides 136, 138 and low points that are closer to axis $A_2$.

Referring to FIGS. 3A and 3C, the bottom element 108 also includes an anterior wall 150 that extends between the protrusions 140A, 140B. The anterior wall preferably serves as a vertebral body stop to prevent over insertion of the intervertebral disc and/or posterior migration of the implant. The anterior wall preferably provides an engagement surface that can be engaged by instruments, including but not limited to tamps and extraction or repositioning instruments. In certain preferred embodiments, the anterior wall may have a curved posterior face adapted to sit flush against a curved anterior face of a vertebral body. In certain preferred embodiments, one or more surfaces of the anterior wall may be coated with an osteoconductive material to facilitate long-term fixation to an endplate surface.

Referring to FIGS. 3F and 3G, the articulating surface 130 preferably defines a convex curve or surface extending between the posterior 132 and anterior ends 134 of the bottom element 104. Referring to FIGS. 3E and 3H, the articulating surface 130 preferably defines a concave curve or surface extending between the lateral sides 136, 138 of the bottom element 104. As will be described in more detail herein, the articulating surface 130 preferably defines a toroidal saddle-shaped surface that engages the articulating surface of the top element 102 (FIG. 2G).

FIGS. 4A and 4B show the top element 102 of FIG. 2A being coupled with the bottom element 104 of FIG. 3A. Referring to FIG. 4B, each of the top and bottom elements 102, 104 desirably has a respective anterior wall 116, 150 that extends between protrusions. The anterior walls 116, 150 preferably extend along the anterior ends 114, 134 of the respective top and bottom elements.

FIG. 4D shows top element 102 including posterior end 112, anterior end 114, and lateral sides 118, 120. The top element 102 includes first bone engaging surface 106 and protrusions 108A, 108B having depressions 121 formed in outer surfaces thereof. The top element 102 includes anterior wall 116 extending between protrusions 108A, 108B.

Referring to FIG. 4C, bottom element 104 has a posterior end 132, anterior end 134, and lateral sides 136, 138. The bottom element 104 includes bone engaging surface 128 and protrusions 140A, 140B. The protrusions include depressions 142 formed in outer surfaces thereof. The bottom element 104 also includes anterior wall 150 extending between protrusions 140A, 140B.

Referring to FIGS. 4E and 4H, the opposing articulating surfaces 110, 130 of the top element 102 and the bottom element 104 are adapted to engage one another. The teeth 122 on the top element 102 slope downwardly toward the posterior end 112 thereof. Similarly, the teeth 144 on the bottom element 104 slope downwardly toward the posterior end 132 thereof.

Referring to FIGS. 4F and 4G, the teeth 122 on the top element 102 have lateral sloping surfaces 126 that slope downwardly toward the sides 118, 120. In contrast, the teeth 144 on the bottom element 104 include lateral sloping surfaces 148 that slope inwardly toward axis $A_3$ (FIG. 4F). As a result, the lateral sloping surfaces 126 of the teeth 122 on the top element 102 slope in a different direction than the lateral sloping surfaces 148 of the teeth 144 on the bottom element 104. Thus, the apex of the teeth 122 on the top element 102 is closer to axis $A_3$ than the apex of the teeth 144 on the bottom element 104. It has been observed that stacking two implants in successive disc spaces may result in cracking of vertebral bone between the implants because the apexes on the teeth of the two implants are in alignment. The present invention seeks to avoid this cracking problem by offsetting the apexes of the teeth on the top element 102 from the apexes of the teeth on the bottom element 104. Although the present invention is not limited by any particular theory of operation, it is believed that providing teeth having off-set apexes enables two or more intervertebral disc implants to be inserted into two or more successive disc spaces, while minimizing the likelihood of cracking the vertebral bodies between the disc spaces.

Referring to FIG. 5, prior to insertion into an intervertebral space, the articulating surface 110 of the top element 102 opposes the articulating surface 130 of the bottom element 104. In preferred embodiments, the articulating surface 110 of the top element 102 defines a toroidal saddle-shaped surface including a concave surface extending between proximal and anterior ends thereof and a convex surface extending between the sides of the top element 102. The articulating surface 130 of the bottom element 104 also includes a toroidal saddle-shaped surface having a convex surface extending between the posterior and anterior ends and a concave surface extending between the sides of the bottom element 104.

The articulating surfaces may be similar to the articulating surfaces disclosed in commonly assigned U.S. Pat. No. 6,997,955. In certain preferred embodiments of the present invention, the longitudinally inwardly directed articulation surface of the top element 102 forms a constant radii saddle-shaped articulation surface. More particularly, the saddle surface is defined by a concave arc that is swept perpendicular to and along a convex arc. The articulation surface has a cross-section in one plane that forms a concave arc, and a cross-section in another plane (perpendicular to that plane) that forms a convex arc. The concave arc has a respective constant radius of curvature about an axis perpendicular to the one plane. The convex arc has a respective constant radius of curvature about an axis perpendicular to the other plane.

In a preferred embodiment, the concave arc has a constant radius of curvature A about an axis perpendicular to the anterior-posterior plane, and the convex arc has a constant radius of curvature B about an axis perpendicular to the lateral plane. Preferably, radius A is less than radius B.

The longitudinally inwardly directed articulation surface of the bottom element 104 also preferably forms a constant radii saddle-shaped articulation surface. More particularly, the saddle surface is defined by a convex arc that is swept perpendicular to and along a concave arc. The articulation surface has a cross-section in one plane that forms a convex arc, and a cross-section in another plane (perpendicular to that plane) that forms a concave arc. The convex arc has a respective constant radius of curvature about an axis perpendicular to the one plane. The concave arc has a respective constant radius of curvature about an axis perpendicular to the other plane.

In a preferred embodiment, the convex arc has a constant radius of curvature C about an axis perpendicular to the anterior-posterior plane, and the concave arc has a constant radius of curvature D about an axis perpendicular to the lateral plane. Preferably, radius C is less than radius D.

The constant radii saddle shaped articulation surfaces are configured and sized to be nestable against one another and articulatable against one another, to enable adjacent vertebral bones (against which the top and bottom elements are respectively disposed in the intervertebral space) to articulate in flexion, extension, and lateral bending. More particularly, the intervertebral disc of the present invention is assembled by disposing the top and bottom elements so that the vertebral body contact surfaces are directed away from one another, and the articulation surfaces are nested against one another such that the concave arcs accommodate the convex arcs.

Accordingly, movement of the adjacent vertebral bones relative to one another is permitted by the movement of the top and bottom elements relative to one another. In flexion and extension, the concave arcs of the top element 102 ride on the convex arcs of the bottom element 104 about a center of rotation below the articulation surfaces. In lateral bending, the concave arcs of the bottom element 104 ride on the convex arcs of the top element 102 about a center of rotation above the articulation surfaces. During these articulations, the elements are maintained at constant relative distraction positions, i.e., the elements do not move in directions that are directed away from one another (for example, do not move in opposing axial directions from one another (e.g., along a longitudinal axis of the spine)). Accordingly, in certain preferred embodiments, the present invention provides a pair of articulation surfaces that have a center of rotation above the surfaces in one mode of motion (e.g., lateral bending), and below the surfaces in another (e.g., flexion/extension), consistent in these regards with a natural cervical intervertebral joint. Preferably, the articulation surfaces are sized and configured so that the respective ranges of angles through which flexion/extension and lateral bending can be experienced are equal to or greater than the respective normal physiologic ranges for such movements in the cervical spine.

It is preferable that, in addition to the flexion, extension, and lateral bending motions described above, the adjacent vertebral bones be permitted by the intervertebral disc implant to axially rotate relative to one another (e.g., about the longitudinal axis of the spinal column) through a small range of angles without moving in opposite (or otherwise directed away from one another) directions (e.g., along the longitudinal axis) within that range, and then to engage in such opposite (or otherwise directed away from one another) movement once that range is exceeded. Preferably, the articulation surfaces are accordingly configured and sized to permit such movements. Because of the differing radii of the opposing articulation surfaces, the top and bottom elements are able to axially rotate relative to one another about the longitudinal axis of the spinal column through a range of angles without causing the vertebral body contact surfaces to move away from one another along the longitudinal axis. Once the axial rotation exceeds that range, the articulation surfaces interfere with one another as the concave arcs move toward positions in which they would be parallel to one another, and the distance between the vertebral body contact surfaces increases with continued axial rotation as the concave arcs ride up against their oppositely directed slopes. Thus, the articulation surfaces are configurable according to the present invention to permit normal physiologic axial rotational motion of the adjacent vertebral bones about the longitudinal axis through a range of angles without abnormal immediate axially opposite (or otherwise directed away from one another) movement, and to permit such axially opposite (or otherwise directed away from one another) movement when under normal physiologic conditions it should occur, that is, outside that range of angles.

The articulation surfaces preferably maintain contact over a range of normal physiologic articulating movement between the adjacent vertebral bones. That is, through flexion, extension, lateral bending, and axial rotation, the articulation surfaces are in contact with one another. Preferably, the surface area dimensions of the articulation surfaces are selected in view of the selected radii of curvature to prevent the edges of the saddle surfaces (particularly the edges of the concave arcs) from hitting any surrounding anatomic structures, or other portions of the opposing upper or lower element, before the limit of the normal physiologic range of an attempted articulation is reached.

Figure 6A:
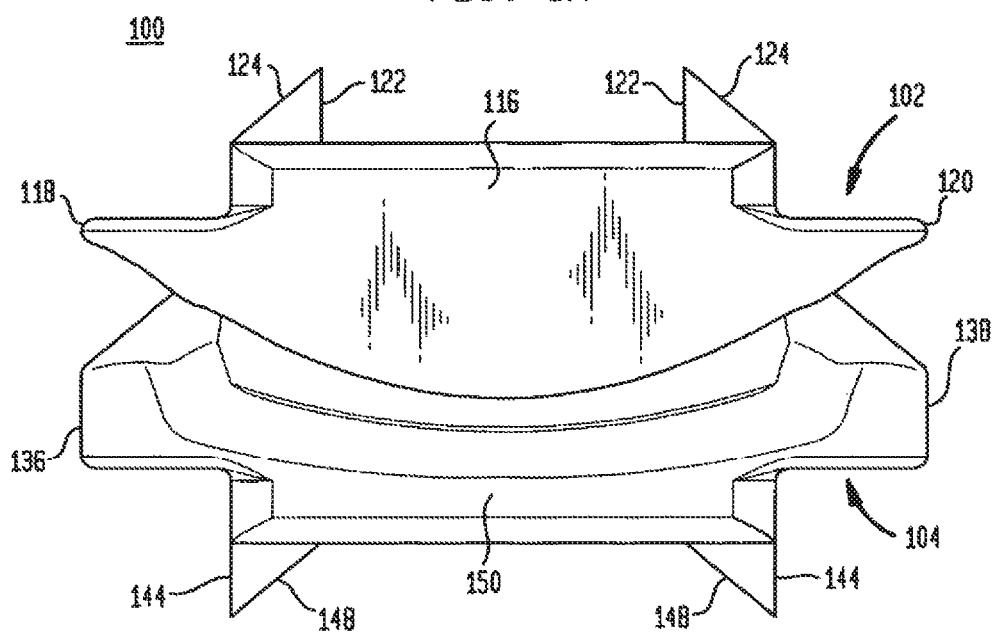
FIG. 6A shows an anterior end view of the intervertebral disc implant shown in FIG. 1.
Figure 6B:
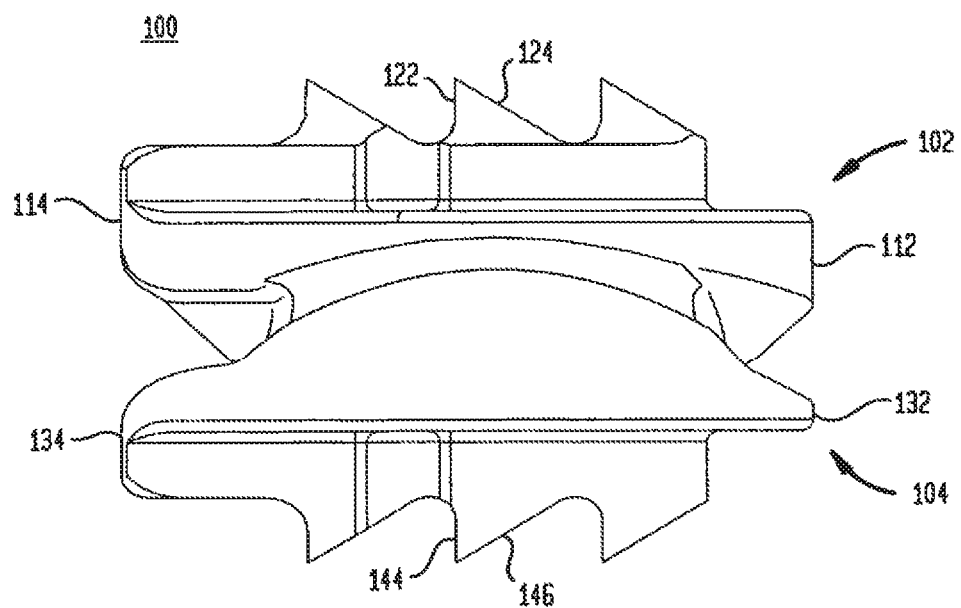
FIG. 6B shows a side elevational view of the intervertebral disc implant shown in FIG. 1.

FIGS. 6A and 6B show, according to a preferred embodiment of the present invention, an intervertebral disc implant 100 including top element 102 and bottom element 104. The articulating surface of the top element 102 preferably engages the articulating surface of the bottom element 104. The articulating surface of the top element 102 preferably defines a convex surface extending between lateral sides 118, 120 thereof. The articulating surface of the bottom element 104 defines a concave surface extending between the lateral sides 136, 138 thereof. Each of the top and bottom elements 102, 104 include respective anterior walls 116, 150 that prevent over insertion and/or posterior migration of the intervertebral disc implant 100. The teeth 122 on the protrusions of the top element 102 include laterally sloping surfaces 124 that slope downwardly toward the sides 118, 120. In contrast, the teeth 144 on the protrusions of the bottom element 104 include laterally sloping surfaces 148 that preferably slope downwardly toward a central region of the bottom element 104. The opposite sloping configuration of the teeth on the respective top and bottom elements 102, 104 preferably permits stacking of two intervertebral disc implants in two successive disc spaces, while minimizing the likelihood of cracking the vertebral bone between the adjacent disc spaces. In other preferred embodiments, the opposite sloping configuration of the teeth enable three or more intervertebral discs to be stacked atop one another over three or more successive disc spaces. In still other preferred embodiments, the teeth of the top and bottom elements may slope laterally in the same direction.

Referring to FIG. 6B, the articulating surface of the top element 102 defines a concave surface extending between posterior 112 and anterior 114 ends thereof. The articulating surface of the bottom element 104 defines a convex surface extending between the posterior 132 and anterior 134 ends of the bottom element 104. The teeth 122 on the protrusions of the top element 102 include sloping surfaces 124 that slope downwardly toward the posterior end 112 of the top element 102. The teeth 144 on the protrusions of the bottom element 104 have sloping surfaces 146 that slope downwardly toward the posterior end 132 of the bottom element 104. As a result, the sloping surfaces 124, 146 of the respective teeth 122, 144 slope in the same direction, i.e., toward the posterior ends of the top and bottom elements 102, 104. The respective sloping surfaces 124, 146 facilitate insertion of the implant 100 into a disc space. The respective vertical surfaces 122, 144 hinder or prevent expulsion or migration of the implant from the disc space after it has been inserted.

Referring to FIGS. 7A-7D in certain preferred embodiments of the present invention, a template 154 has a distal end 156 and a proximal end 158. The template 154 includes a shaft 160 extending between the distal and proximal ends and a handle 162 secured to a proximal end of the shaft. The template includes a template marker 164. As shown in FIG. 7D, the template marker 164 has a cruciform-like structure with a first vertically extending arm 166, a second vertically extending arm 168, a first lateral arm 170 and a second lateral arm 172. The upper and lower ends of the respective first and second vertically extending arms 166, 168 preferably have apexes that may be used for aligning scoring of the anterior faces of the adjacent vertebral bodies. The score marks may later be used for aligning other tools and/or the intervertebral disc. The template marker 164 includes a central pin 174, a first tack 176 on the first vertical arm 166 and a second tack 178 on the second vertical arm 168. The central pin 174 is adapted to engage a natural disc and the tacks 176, 178 are adapted to engage bone, such as vertebral bone. The central pin 174 may also be replaced or supplanted by a plurality of pins positioned on the lateral arms 170, 172. Referring to FIG. 7D, the lateral arms 170, 172 preferably define a distal surface 180 that is curved for matching the curve of the anterior surface of a natural intervertebral disc.

FIGS. 8A-8D show a template marker for a template, in accordance with another preferred embodiment of the present invention. The template marker 164' is substantially similar to the template marker shown in FIG. 7D. However, the template marker 164' shown in FIGS. 8A-8D includes first and second engagement features or projections 182A' and 182B' projecting from top and bottom surfaces of adapter shaft 184'.

Referring to FIGS. 9A and 9B, the template marker 164' may be attached to a distal end 156' of a template handle 162'. The adapter shaft 184' of the template marker 164' is inserted into an opening at the distal end 156' of the template handle 162'. The projections 182A', 182B' on the adapter shaft 184' are inserted into opposing grooves 186' formed in the template handle 162'.

FIGS. 10A-10B show the template marker 164' secured to the distal end 156' of the template handle 162'. Referring to FIGS. 10A-10C, after the projections 182A' and 182B' on the template marker 164' have been received within the grooves at the distal end of the template handle 162', a rotatable handle 188' is rotated for advancing shaft 190' relative to outer shaft 192' so as to lock the template marker 164' to the distal end 156' of the template handle 162'. In certain preferred embodiments, the template handle 162' is rotated to seat the projections 182A', 182B' in the grooves 186' and the rotatable handle 188' is rotated to hold the projections 182A', 182B' forward in the grooves 186'.

FIGS. 11A-11B show a reference pin drill guide 194 having a distal end 196, a proximal end 198, a shaft 200 extending between the distal and proximal ends and a handle 202 at the proximal end of the shaft 200. The distal end 196 of the reference pin drill guide includes a main body 204 having an upper end 206 and a lower end 208. The main body includes a first opening 210 extending therethrough adjacent upper end 206 and a second opening 212 extending therethrough adjacent lower end 208. The main body includes a head 214 that projects from a distal side thereof. The head includes a tapered nose 216, a top surface 218, and a bottom surface 220. The head 214 also includes a first vertebral body stop 222 projecting upwardly from top surface 218 and a second vertebral body stop 224 projecting below second surface 220.

Referring to FIGS. 11A and 11C, the shaft 200 of the reference pin drill guide 194 is preferably angled or curved so that the working end of the tool may be observed by a surgeon. As shown in FIGS. 11A-11C, a distal end 226 of a drill bit 228 may be passed through openings 210, 212 for forming holes in the vertebral bone. As will be described in more detail below, the threaded ends of reference pins may be inserted into the holes. Referring to FIG. 11A, the main body 204 preferably includes an upper alignment flange 230 projecting from upper end 206 thereof and a lower alignment flange 232 projecting from lower end 208 of main body 204, for use in aligning the flanges with alignment marks previously scored on the vertebral bones.

The drill bit 228 includes a distal end 226 and a proximal end 234 adapted to be secured by a drill. The drill bit 228 includes a shoulder 236 that limits advancement of the drill bit through the openings 210, 212 of the main body 204.

Referring to FIGS. 13A and 13B, in order to make holes in the vertebral bone for alignment or reference pins, the head 214 of the reference pin drill guide 194 is inserted into the disc space between the vertebral bodies. The head is advanced until the vertebral body stops abut the anterior faces of the respective vertebral bodies. The distal end of the drill bit 228 is then inserted through the openings 210, 212 in the main body 204. The distal end of the drill bit 228 is advanced into bone to form the openings for the reference pins.

Referring to FIGS. 14A-14C, in certain preferred embodiments of the present invention, a reference pin insertion guide 236 has a distal end 238, a proximal end 240, a shaft 242 extending between the distal and proximal ends and a handle 244 secured to the distal end of the shaft 242. The reference pin insertion guide 236 includes alignment guide body 246 having an upper end including a first opening 248 and a lower end including a second opening 250. The distal end also includes a head 252 insertable into an intervertebral disc space. The head 252 has a tapered nose 254, a top surface 256 terminating at a first vertebral body stop 258 and a bottom surface 260 terminating at a second vertebral body stop 262. The first and second vertebral body stops 258, 262 preferably prevent over insertion of the tool into an intervertebral disc space.

FIGS. 15A-15C show an alignment or reference pin 264, in accordance with certain preferred embodiments of the present invention. Referring to FIGS. 15A and 15B, the reference pin 264 has a distal end 266 and a proximal end 268. Referring to FIG. 15B, the distal end 266 includes a threaded portion 270 that is threadable into vertebral bone. The distal end of reference pin 264 also preferably includes a flange 272 that limits insertion of the reference pin. A proximal side of the flange 272 includes a feature or hex nut 274 engageable by a driver.

FIG. 16 shows a rescue reference pin 264', in accordance with another preferred embodiment of the present invention. The rescue pin 264' is substantially similar to the reference pin 264 shown in FIG. 15B and includes a threaded shaft 276' located on a posterior side of flange 272'. The rescue pin 264' is preferably used if the reference pin 264 shown in FIG. 15B does not remain anchored to bone or pulls out of the bone. The rescue pin 264' preferably has larger diameter threading (than the reference pin 264) at the leading end thereof.

Referring to FIGS. 17A-17C, in certain preferred embodiments of the present invention, a reference pin driver 280 is utilized for driving reference pins into bone. The reference pin driver 280 includes a distal end 282 having an opening adapted to receive a reference pin 264 (or a rescue pin 264') and a proximal end 284 including a handle 286. The reference pin driver 280 also includes a shaft 288 that extends between the distal end 282 and the proximal end 284. The shaft 288 preferably has an opening including at least one hexagonal surface that matches the hexagonal nut 274 on the reference pin 264 (FIG. 15A).

FIGS. 18A and 18B show, for use in preferred embodiments of the invention, a sleeve 290 insertable into the openings in the reference pin drill guide 194. The sleeve 290 includes a distal end 292 having an opening 294 and a proximal end 296 including a stop flange 298. Referring to FIG. 18B, the distal end 292 of sleeve 290 includes opening 294 extending therethrough and larger opening 296 at the distal-most end. The enlarged opening 296 preferably has a circular counterbore that freely slides over the hex nut on the reference pin 264 described above. The smaller opening 294 preferably forms a sliding fit with an outer surface of the reference pin 264. The sleeve 290 preferably stabilizes the reference pin insertion guide 236 after the first reference pin has been inserted into bone and during insertion of the second reference pin.

Figure 19A:
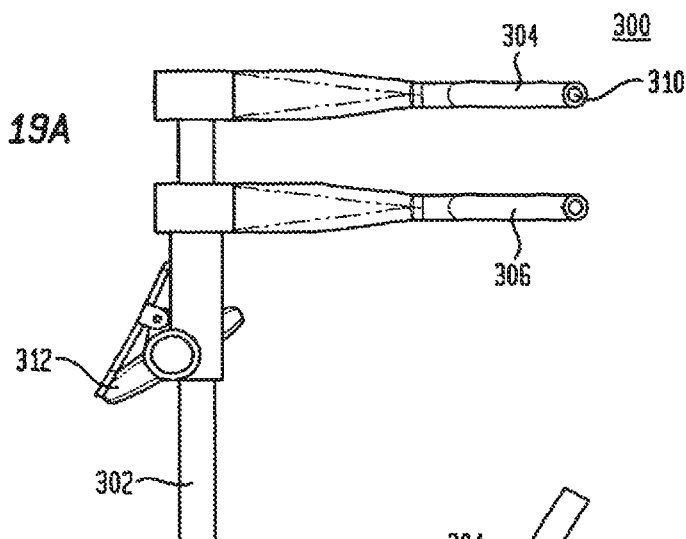
FIGS. 19A-19C show a distractor, in accordance with certain preferred embodiments of the present invention.
Figure 19B:
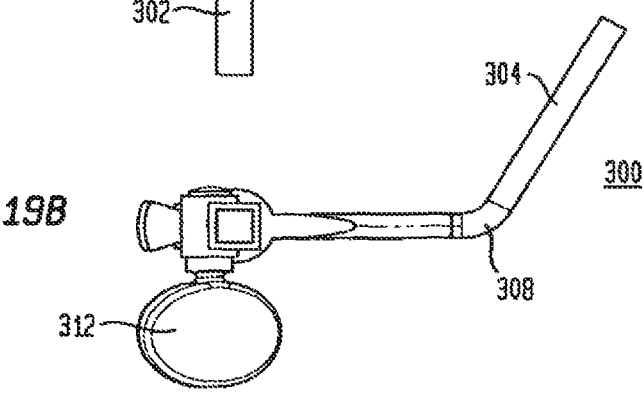
Figure 19C:
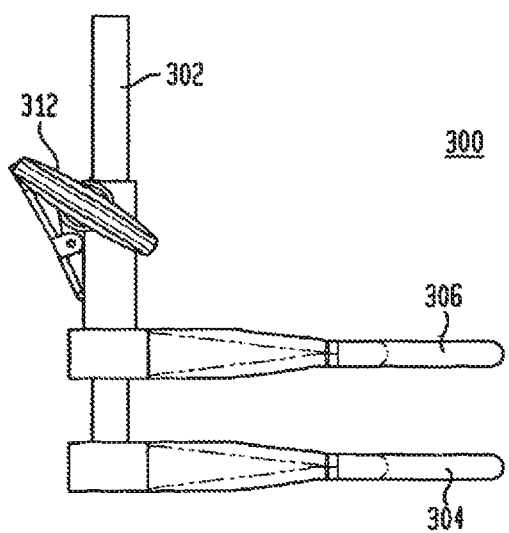

FIGS. 19A-19C shows a distraction instrument 300 including support element 302 and first and second distracting arms 304, 306 that travel over the support element 302. Each distracting arm 304, 306 has a curved section 308 and openings 310 at distal ends of the arms 304, 306. The distracting element 300 also includes adjustment element 312 that interacts with support body 302 and arms 304, 306 for adjusting the distance between the arms. As will be described in more detail herein, after reference pins 264 are inserted into vertebral bone, the distractor arms 304, 306 are slid over the reference pins. Once the distractor element 300 is coupled with the reference pins 264, the adjusting element 312 may be operated for separating the distractor arms 304, 305 so as to distract adjacent vertebrae and allow for removal of disc material.

Referring to FIGS. 20A-20D, in accordance with certain preferred embodiments of the present invention, a drill guide 314 has a distal end 316, a proximal end 318, a shaft 320 extending between the distal and proximal ends and a handle 322 adjacent the distal end 318. The drill guide includes a main body 324 attached to the distal end of the shaft 320. Referring to FIG. 20D, the main body 324 includes first and second openings 326, 328 for engaging the reference pins. The main body 324 also includes four drill guide openings 330A-330D for guiding a distal end 332 of a drill bit 334. The four drill guide openings 330A-330D are positioned to coincide with the protrusions of an intervertebral disc implant. Referring to FIGS. 20A and 20C, the main body 324 also includes a head 336 insertable into an intervertebral disc space. The head 336 includes a tapered nose 338, a top surface 340, a bottom surface 342, and first and second vertebral body stops 344, 346 extending above and below the top and bottom surfaces 340, 342. As will be described in more detail herein, the alignment openings 326, 328 are slid over the reference pins and the tool is advanced until the head 336 is positioned in the intervertebral disc space. The distal end 332 of the drill bit 334 is then passed in series through the drill alignment openings 330A-330D for at least partially forming protrusion openings for the protrusions of an intervertebral disc implant.

Figure 21B:
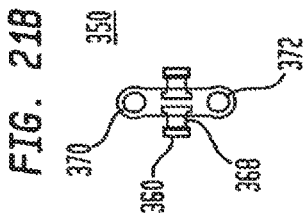
FIGS. 21A-21D show a chisel guide, in accordance with certain preferred embodiments of the present invention.
Figure 21D:
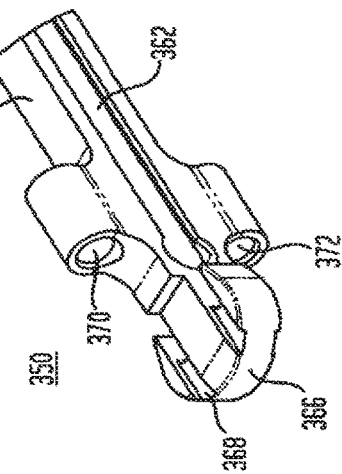
Figure 21A:
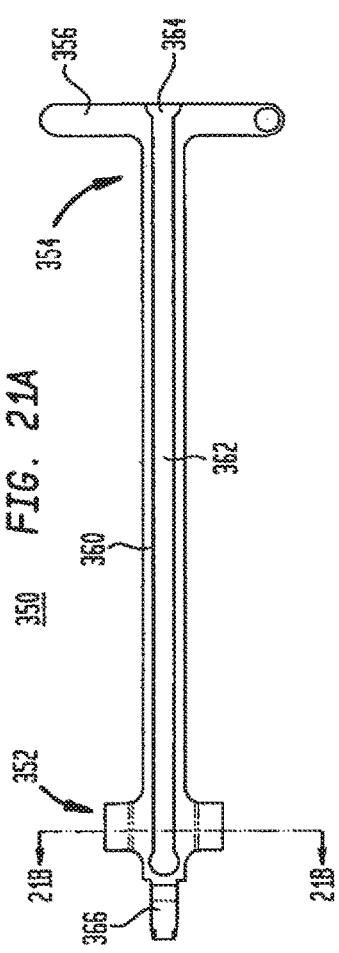
Figure 21C:
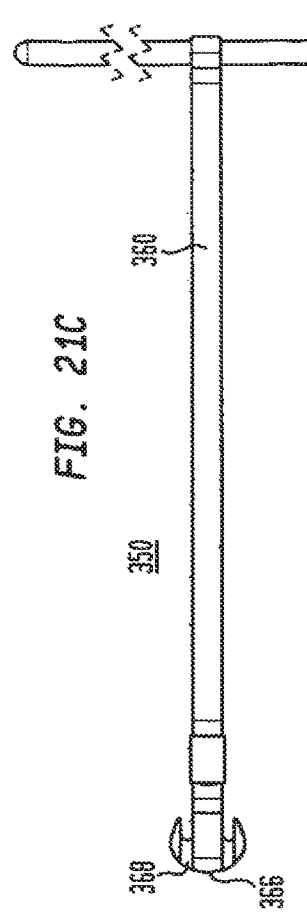

Referring to FIGS. 21A-21D, in accordance with certain preferred embodiments of the present invention, a chisel guide 350 includes a distal end 352, a proximal end 354 with a handle 356 and a shaft 360 extending from the proximal end toward the distal end. The shaft 360 includes on one side a left track 362 having an opening 364 at the proximal end 354 and extending toward the distal end 352, and, on an opposite site, a right track 362' having an opening 364' at the proximal end 354 and extending toward the distal end 352. The chisel guide 350 includes a head 366 at the distal end 352. Referring to FIGS. 21C and 21D, the head 366 includes alignment grooves 368 formed in top and bottom surfaces thereof. The alignment grooves are adjacent the left and right tracks of the shaft 360.

Referring to FIGS. 21B and 21D, the chisel guide also includes first and second reference pins openings 370, 372. In operation, the reference pin openings 370, 372 are slid over the reference pins described above, and the head 366 is inserted into an intervertebral disc space.

Referring to FIGS. 22A-22D, in certain preferred embodiments of the present invention, a chisel 374 has a distal end 376 with first and second cutting blades 378, 380, and a proximal end 382 having a handle 384 and a striking surface 386. The chisel 374 includes a shaft 388 extending between the distal and proximal ends of the tool. The shaft 388 includes projections extending therefrom for guiding the chisel in the tracks of the chisel guide shown in FIGS. 21A-21D. Referring to FIGS. 22B and 22D, the projections 390 guide the chisel along the track while maintaining alignment of the chisel. Referring to FIG. 22C, the distal end of the chisel includes an opening extending between cutting blades 378, 380. The opening 394 allows the cutting blades 378, 380 to slide over the grooves 368 formed in the top and bottom surfaces of the head 366 (FIG. 21D).

Referring to FIG. 23, the chisel guide 350 described in FIGS. 21A-21D is slid over the reference pins 264 secured to bone. The chisel 374 of FIGS. 22A-22D is then slideably advanced along one of the tracks of the chisel guide for forming protrusion openings in the bone. The same or a second chisel 374 is then slideably advanced along the other of the tracks to form additional protrusion openings in the bone.

FIGS. 24A-24B show a mallet 396 including a handle 398 having a lower end 400 and an upper end 402 with a striking element 404 secured to the upper end. The striking element 404 includes a U-shaped opening 406 formed therein so that the mallet may be used as a slap hammer.

FIGS. 25A-25D show a sizer 408, in accordance with certain preferred embodiments of the present invention. The sizer 408 includes a main body 410 having a distal end 412, a top surface 414, and a bottom surface 416. The body 410 includes sloping surfaces 418 extending between the distal end 412 and the top and bottom surfaces 414, 416 to ease insertion of the sizer between the vertebrae. The sizer 408 also includes an adapter shaft 420 and first and second projections 422A, 422B.

The sizer also includes vertebral body stops 424 and 426 for limiting insertion of the sizer. Referring to FIGS. 25A and 25B, the sizers are preferably provided in variable heights (e.g., 5-9 mm) and variable base plate widths (e.g., 14 and 16 mm). Sequentially larger sizers are used to determine the desired implant height that will best fit into the disc space without over-tensioning the annulus. In their preferred usage, the sizer that fits snugly into the disc space with mild to moderate resistance to pull-out should indicate the proper height of the disc to be implanted.

Referring to FIGS. 26A-26E, a sizer 408 may be attached to a distal end 430 of a handle 432 by sliding the projections 422A, 422B into grooves extending from the distal end 430 of the handle 432. After the sizer 408 is coupled with the handle 432, a rotatable element 434 may be rotated for locking the sizer 408 to the handle 432. In certain preferred embodiments, the handle 432 is rotated to seat the projections 422A, 422B in the grooves extending from the distal end 430 of the handle and the rotatable element 434 is rotated to hold the projections 422A, 422B forward in the closed ends of the grooves.

Referring to FIGS. 27A-27D, in certain preferred embodiments of the present invention, a trial 436 includes a distal end 438, a proximal end 440, a shaft 442 extending between the distal and proximal ends, and a striking surface 444 located at the proximal end 440 of the shaft 442. The trial also includes a trial implant 446 secured at distal end 438. The trial implant 446 includes protrusions 448 having teeth 450 that are positioned to coincide with the protrusions of a intervertebral implant. The size of the trial implant 446 is selected based upon the largest sizer that safely fit within the intervertebral disc space. The trial 436 also includes reference pin alignment openings 452, 454. The reference pin alignment openings 452, 454 are adapted to slide over the reference pins secured to vertebral bone.

Referring to FIGS. 28A-28F, in accordance with certain preferred embodiments of the present invention, an implant dispenser 456 is adapted to hold the top and bottom elements of an intervertebral disc implant as a single unit with the articulating surfaces held together. Referring to FIGS. 28A-28C, the implant dispenser 456 is preferably flexible and includes a superior arm 458 for engaging a top element of an intervertebral disc implant and an inferior arm 460 for engaging a bottom element of an intervertebral disc implant. The superior and inferior arms preferably have lateral notches 462 formed therein for receiving the teeth of the top and bottom elements, as will be described in more detail herein. The implant dispenser also preferably includes a central support 464 that enables the superior and inferior arms 458, 460 to move away from one another for releasing an intervertebral disc implant.

Referring to FIG. 28E, the superior arm 458 preferably has indicia such as a text or a symbol 466 indicating that the arm 458 overlies the top element of the implant. The indicia on the superior arm may also preferably include the size 468 of the implant. FIG. 28F shows the inferior arm 460 including indicia such as a text or a symbol 470 indicating that the arm 460 overlies the bottom element of the implant. The inferior element indicia may also include size information 472 as shown.

FIGS. 29A-29E show the intervertebral disc implant of FIG. 1 secured in the implant dispenser 456 of FIGS. 28A-28F. The intervertebral disc implant includes top element 102 engaged by superior arm 458 and central element 464. The bottom element 104 is engaged by inferior arm 460 and central element 464. The teeth of the implant extend through the notches 462 in the superior and inferior arms.

FIGS. 30A to 30E-1 show an inserter head for inserting an intervertebral disc implant. Referring to FIGS. 30A-30B, the inserter head 474 includes a main body 476 having a distal end 478 and a proximal end 480. The distal end 478 of the main body 476 includes four spaced arms 482 having inwardly facing surfaces with projections 484 that are adapted to fit within the depressions formed within the protrusions of the top and bottom elements of the intervertebral disc implant. The main body includes a central opening 486 extending from the proximal end 480 to the distal end 478 thereof. Referring to FIGS. 30C and 30D, the main body 476 also includes an upper alignment groove 488 and a lower alignment groove 490. The alignment grooves 488, 490 are adapted to engage the reference pins for guiding advancement of the inserter head. In certain preferred embodiments, the alignment grooves 488, 490 taper toward one another so that the grooves are closer to one another at distal ends thereof and farther away from one another at proximal ends thereof.

FIGS. 30E and 30E-1 show the projection 484 on one of the four arms 482. As noted above, the projections 484 on the arms 482 engage the depressions in the protrusions of the top and bottom elements of the intervertebral discs.

FIG. 31 shows the inserter head 474 of FIG. 30A prior to assembly with an inserter handle 492. The inserter handle 492 includes a pusher rod 494 that may be advanced by a rotatable handle 496 coupled with the pusher rod 494. The handle includes a shaft 496 that is insertable into opening 486 of the inserter head. Referring to FIGS. 32A and 32B, after the inserter head 474 has been coupled with the inserter handle, the element 496 may be rotated for advancing the pusher rod 494. As will be described in more detail below, advancing the pusher rod 494 will disengage the top and bottom elements of an intervertebral disc with the arms 482 of the inserter head 474.

Figure 29A:
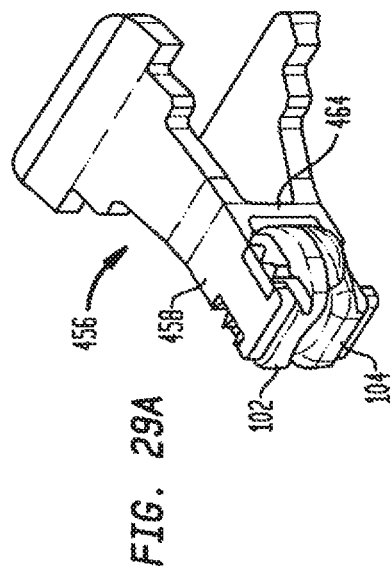
FIGS. 29A-29E show the implant dispenser of FIGS. 28A-28F, coupled with the intervertebral disc implant shown in FIG. 1.
Figure 29B:
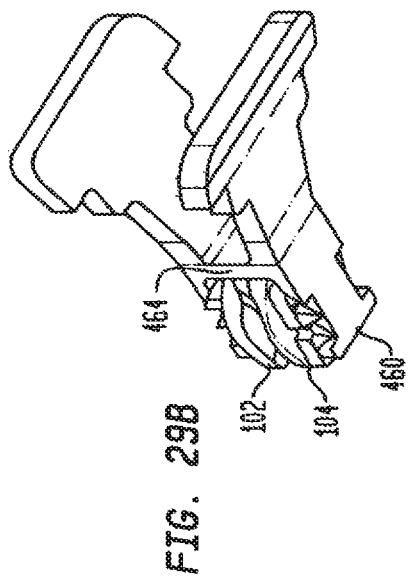
Figure 29C:
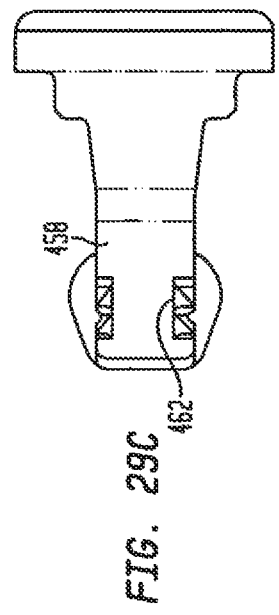
Figure 29E:
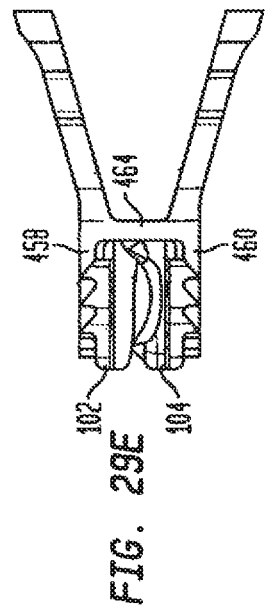
Figure 29D:
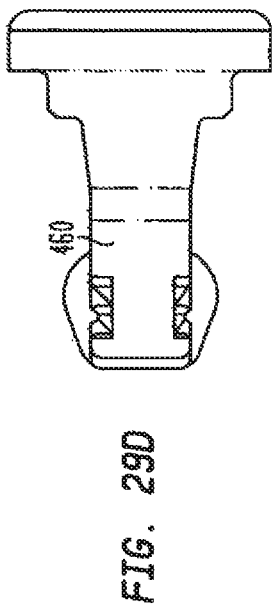

FIGS. 33A and 33B show the implant dispenser 456 of FIG. 29A holding an intervertebral disc implant 100. Referring to FIG. 33B, the depressions in the protrusions are coupled with the projections in the arms 482 of the inserter head 474. Referring to FIGS. 34A and 34B, after the implant 100 has been secured to the arms 482 of the inserter head 474, the implant dispenser may be removed. Referring to FIG. 34B, at this point, the implant 100 is held by the arms 482 of the inserter head. Referring to FIGS. 35A-35B, the pusher rod 494 may be advanced toward the distal end of the inserter head 474 for decoupling the implant 100 from the inserter head 474.

Referring to FIGS. 36A and 36B, in accordance with certain preferred embodiments of the present invention, a tamp 500 includes a distal end 502, a proximal end 504, a shaft 506 extending between the distal and proximal ends and a handle 508 adjacent the proximal end 504. The distal end 502 includes an abutting surface 510 that is adapted to engage the anterior end of an intervertebral disc implant. The tamp 500 also includes a striking surface 512 at the proximal end. A device such as the mallet shown and described above may be impacted against the striking surface 512 for applying force to the striking surface 510 of the tamp.

FIGS. 37A-37D show an extractor 514, in accordance with certain preferred embodiments of the present invention. The extractor 514 includes a distal end 516 having a hook 518, a proximal end 520, and a shaft 522 extending between the distal and proximal ends. The extractor 514 also preferably includes a handle 524 adjacent the proximal end 520 thereof. FIGS. 37C and 37D show shaft 522 with a hook 518 at a distal end of the shaft.

Disclosed herein are implants, surgical instruments and procedures in accordance with certain preferred embodiments of the present invention. It is contemplated, however, that the implants, instruments and procedures may be slightly modified, and/or used in whole or in part and with or without other instruments and procedures, and still fall within the scope of the present invention. Although the present invention may discuss a series of steps in a procedure, the steps may be accomplished in a different order, or may be used individually, or in conjunction with other methods, without deviating from the scope of the present invention.

Figure 38:
FIGS. 38-74 show a method of inserting an intervertebral disc implant, in accordance with certain preferred embodiments of the present invention.
Figure 39:
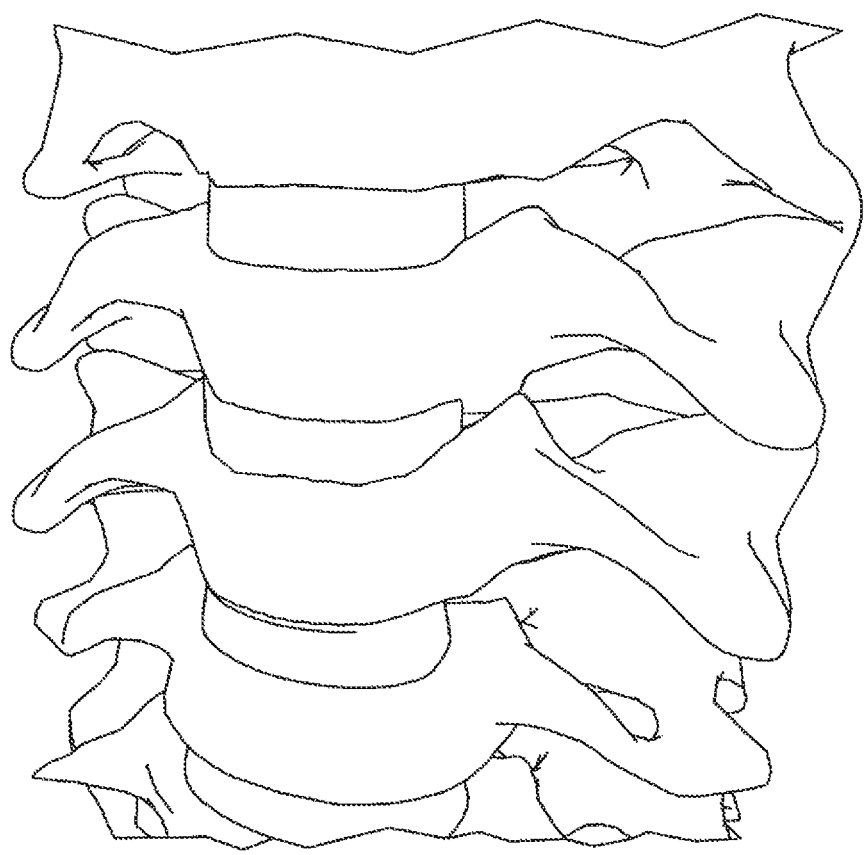

Prior to implanting the intervertebral disc implant, a review of X-rays, MRI or CT-myelogram is preferably conducted to assess the level to be treated for osteophytes and to compare the intervertebral disc height with the adjacent levels. Referring to FIG. 38, the patient is preferably positioned in the supine position to provide for an anterior surgical approach to the cervical spine. Steps should preferably be taken to stabilize the patient's spine in a neutral position and to prevent rotation during the procedure. In certain preferred embodiments, it may be preferable to place a towel or bean bag underneath the patient's shoulders. Tape, a halter or skeletal traction may be used to prevent rotation. Referring to FIGS. 38 and 39, a transverse skin incision is preferably made at the appropriate level to expose the targeted spinal segment including the discs above and below the target spinal segment. Care should be taken to avoid prolonged retraction pressure on vital structures, such as the esophagus.

Figure 40:
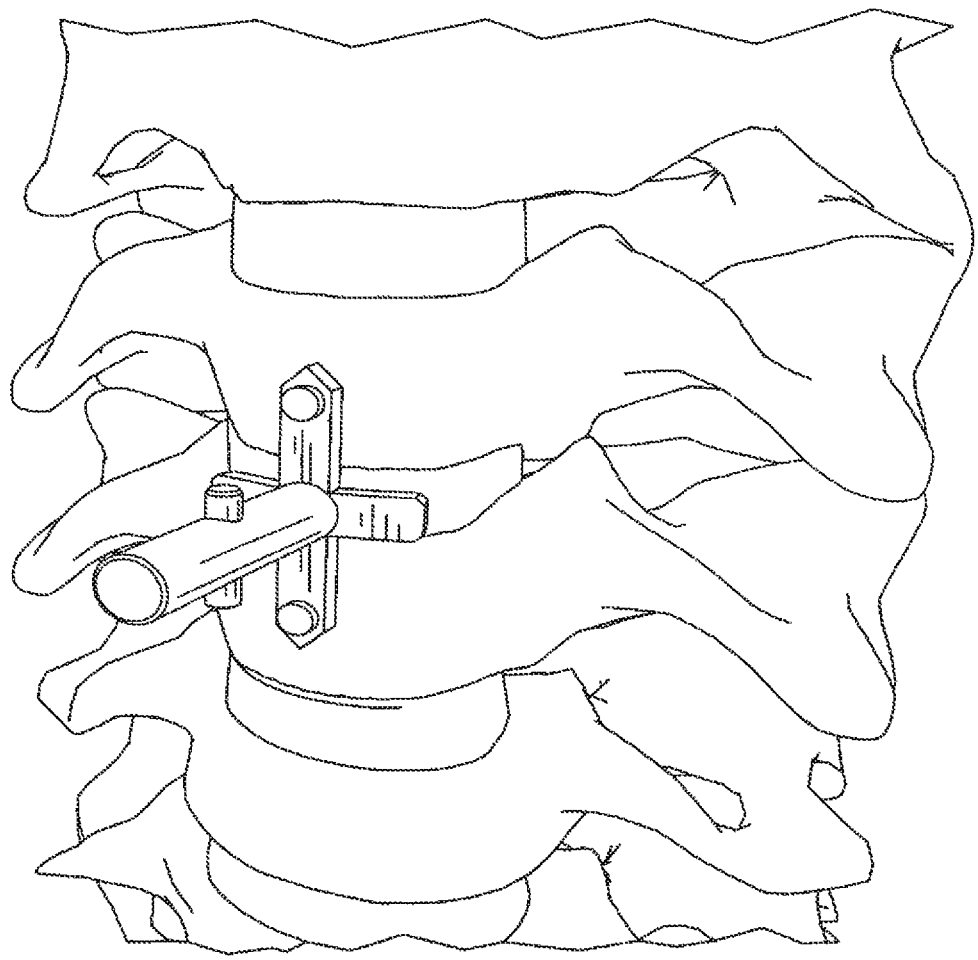

Another step in the intervertebral disc implantation procedure involves identifying and marking a midline on the target segment of the spine. In preferred embodiments, a template, such as the template shown and described above in FIGS. 7A-10D, is utilized to mark the midline. In certain preferred embodiments, the size and dimensions of the template may vary. The exact template selected may be based upon initial estimation of the appropriate implant size from pre-operative X-rays and/or MRI/CT. The template is preferably attached to the template handle, as described above in reference to FIGS. 9A-9B and 10A-10D. The template may have different sizes whereby the lateral arms of the template attachments approximate the width options of the implant (i.e., 14 mm and 16 mm). Referring to FIG. 40 and FIG. 9A, the central pin at the distal end of the template is inserted into the middle of the disc so that the upper and lower vertically extending arms are approximately aligned with the midline axis of the vertebral column. The tacks on the upper and lower vertical arms engage the vertebral bone to stabilize the template. The handle at the proximal end of the template handle may be tapped, such as by using a mallet, to push the tacks into the vertebral bone. The template handle may then be disengaged from the template, which remains attached to the vertebral bone. At this stage, fluoroscopy may be used to verify the midline and lateral margins of the disc space. In addition, the spinous processes are preferably centered.

Figure 41:
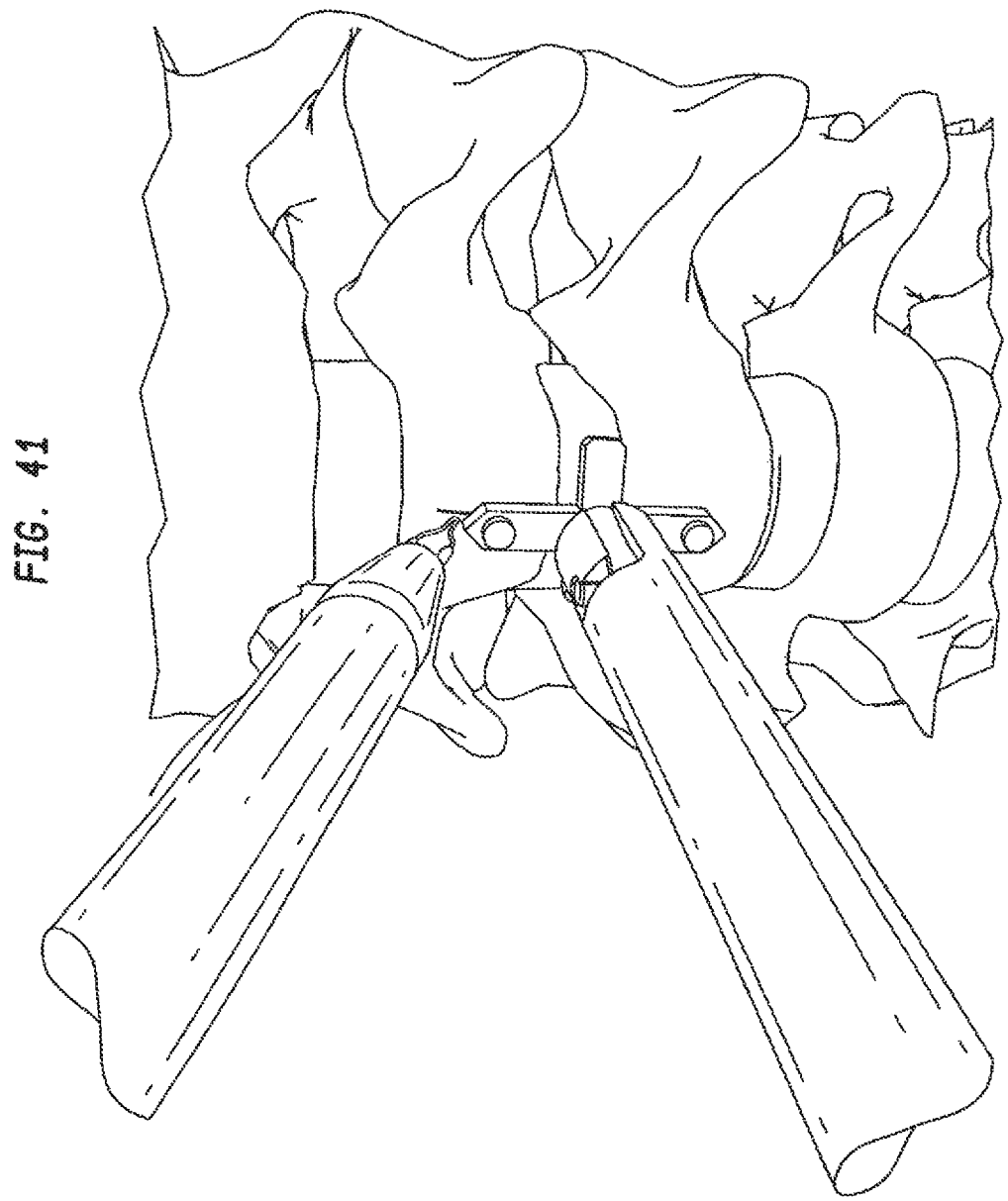
Figure 42:
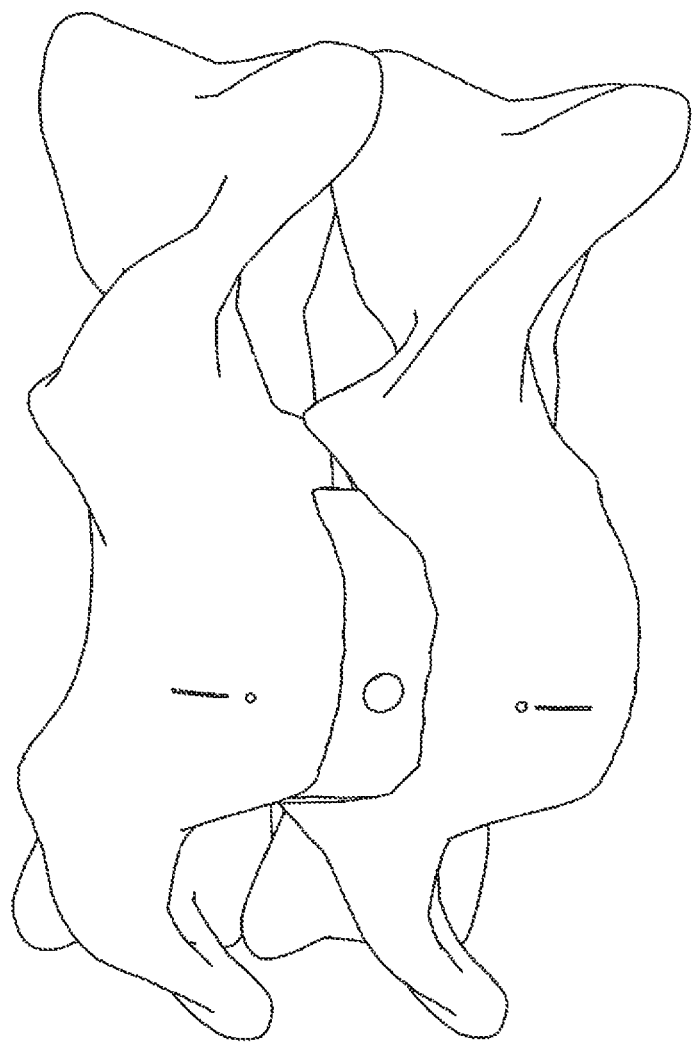

Referring to FIG. 41, a tool such as a scalpel or an electrocautery tool is preferably utilized to score the midline points on the anterior surfaces of the superior and inferior vertebral bodies. Care is preferably taken to ensure that the midline is well defined for all subsequent endplate preparation and implant insertion steps. Referring to FIGS. 41 and 42, after the midline points have been scored, the template handle may be reattached to the template for removing the template from engagement with the target area. FIG. 42 shows the target area of the spine with an opening formed in the disc space by the central pin of the template, and two smaller openings being formed in the respective superior and inferior vertebral bodies by the tacks of the template. In addition, the scoring of the midline points is evident at the anterior surfaces of the superior and inferior vertebral bodies.

Figure 43:
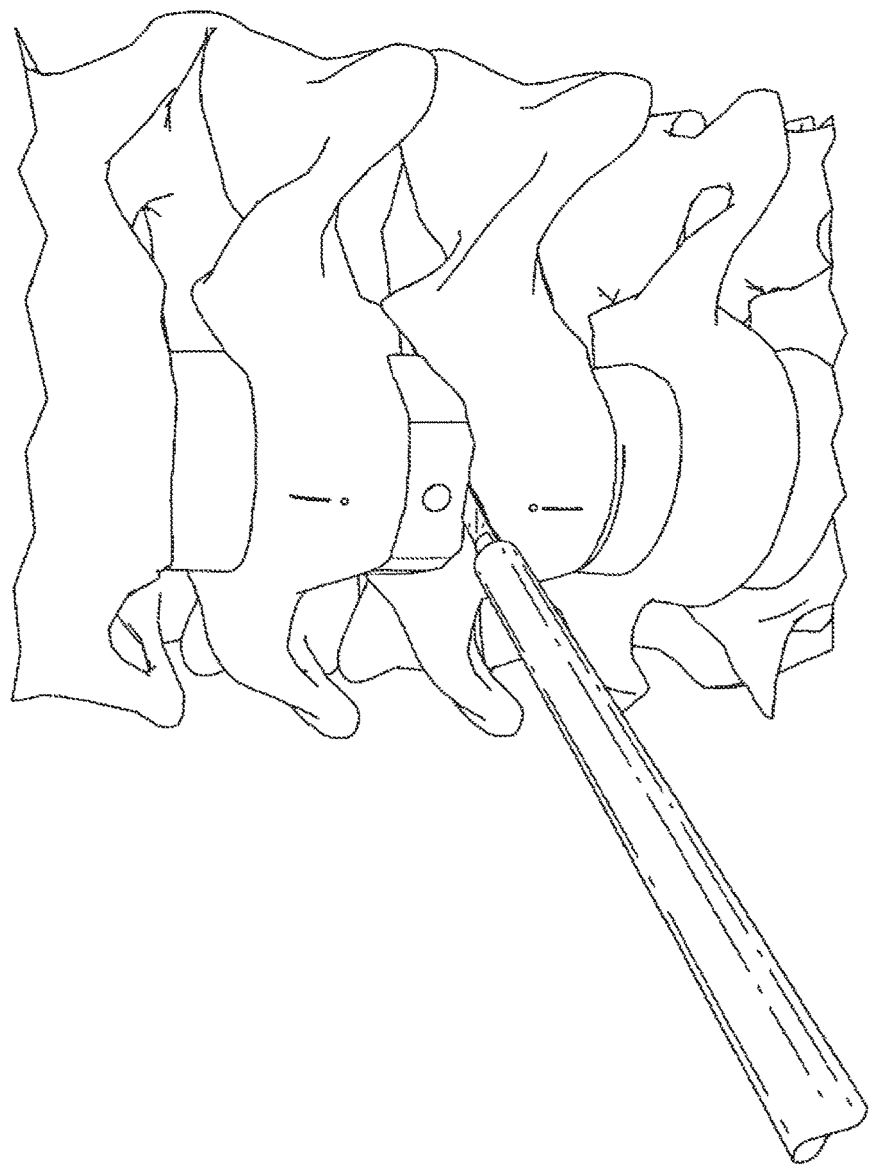
Figure 44:
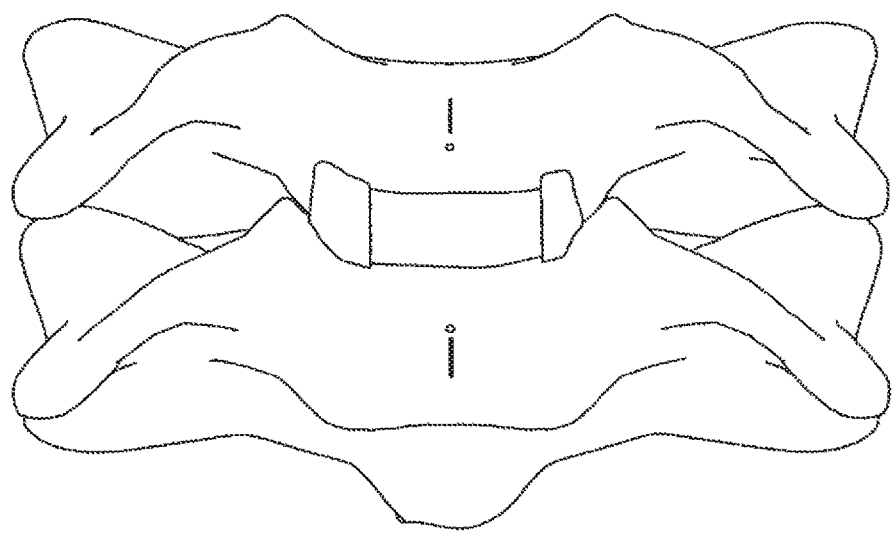

Referring to FIG. 43, a cutting tool such as a scalpel may be used to dissect a window in the annulus of the targeted disc. The size of the window dissected in the annulus preferably approximates the width of an intervertebral disc implant to be inserted therein. In certain preferred embodiments, radiographic imaging such as fluoroscopy may be used to identify osteophytes that extend anteriorly. Any osteophytes that extend anteriorly are preferably resected back to the vertebral body so that the surfaces of the superior and inferior vertebral bodies are flattened. Moreover, techniques such as radiographic imaging should be used to identify any osteophytes extending downwardly or upwardly into the anterior region of the disc space. Such osteophytes should be resected to the endplates. FIG. 44 shows the targeted disc space after the initial discectomy has been completed including resection of any anterior osteophytes present in the targeted disc area.

Figure 45:
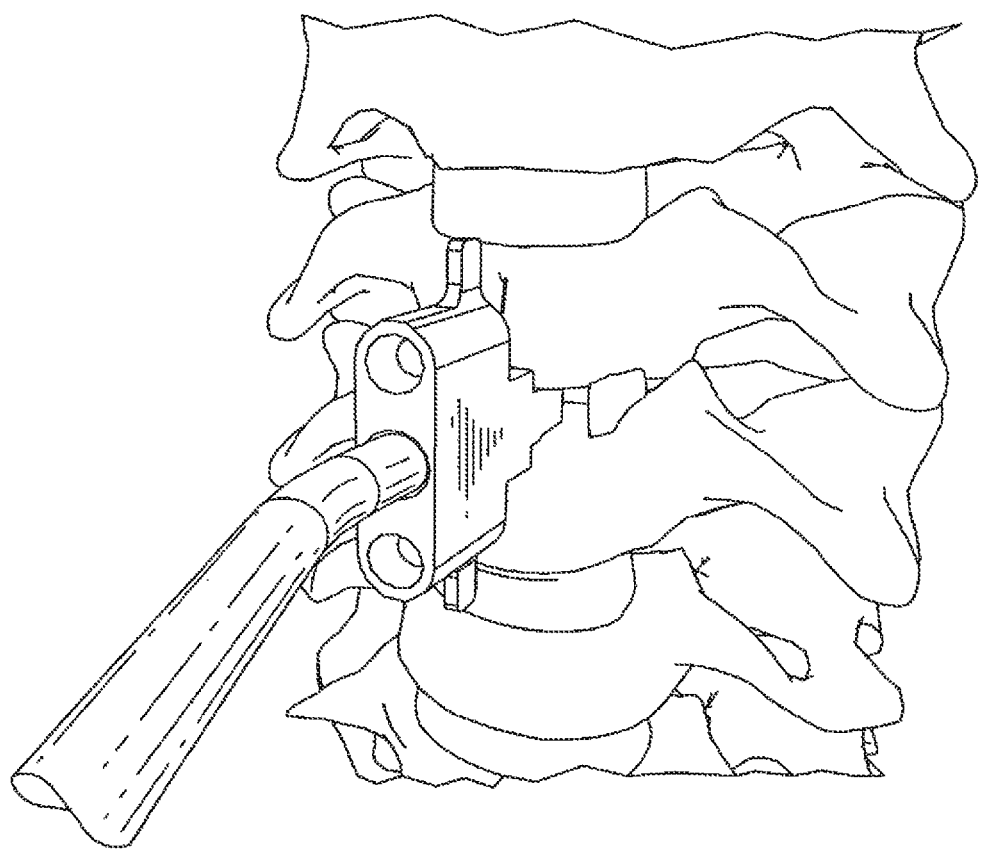
Figure 46:
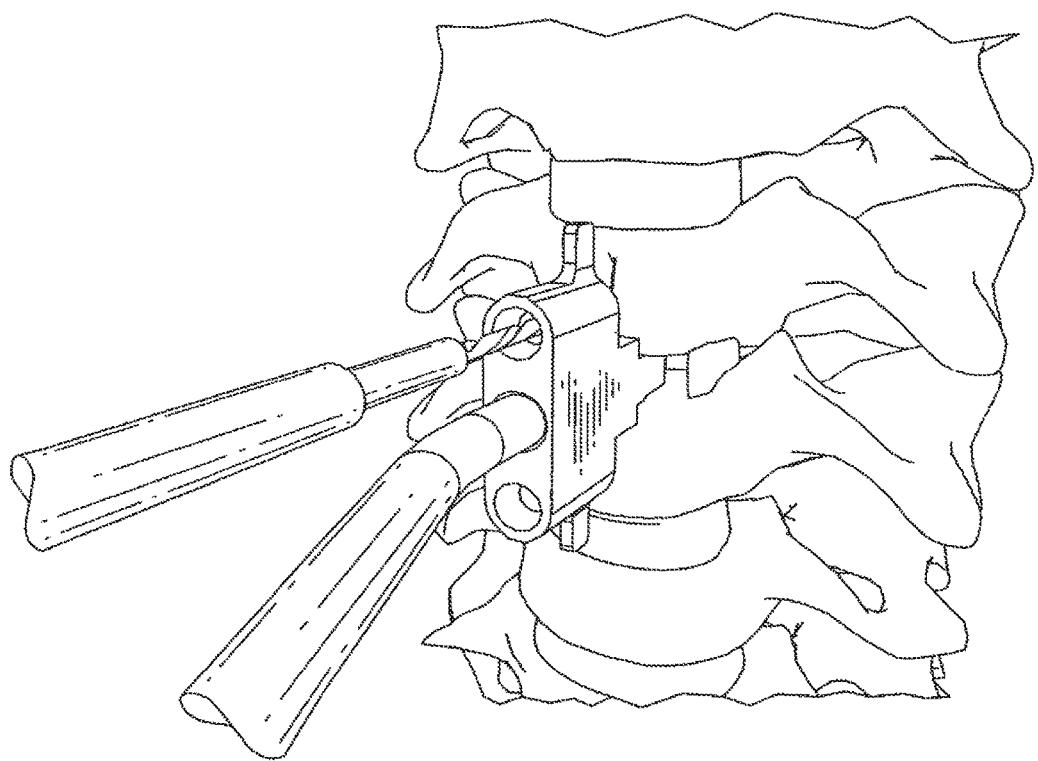
Figure 47:
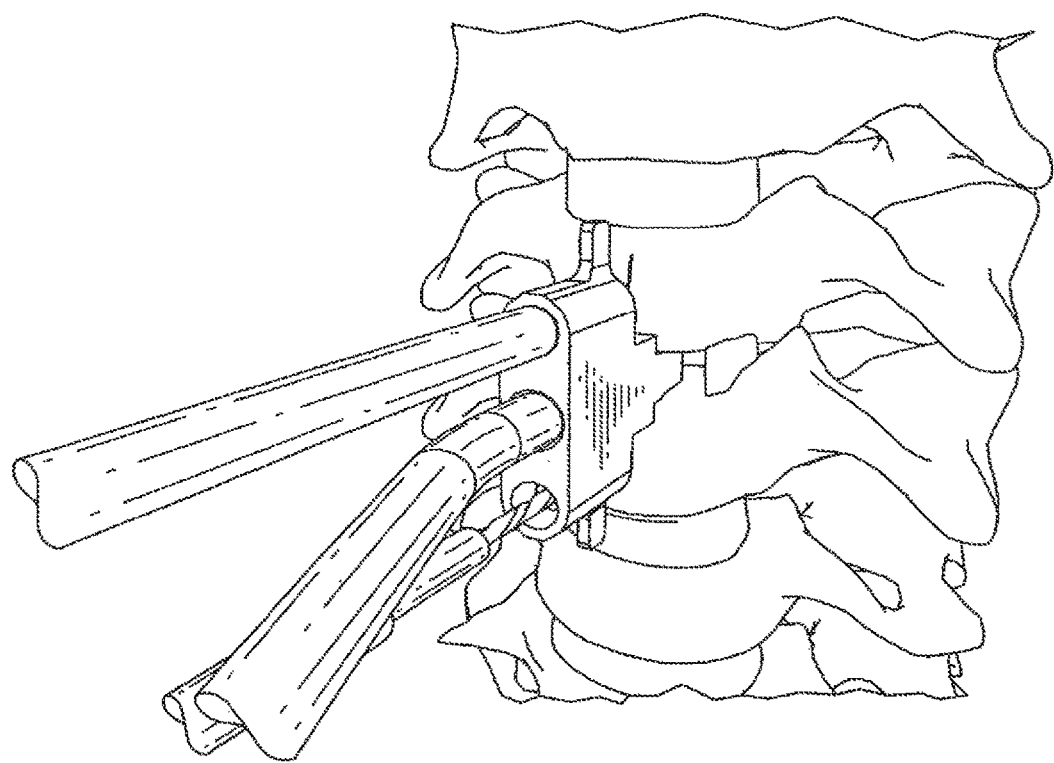
Figure 48:
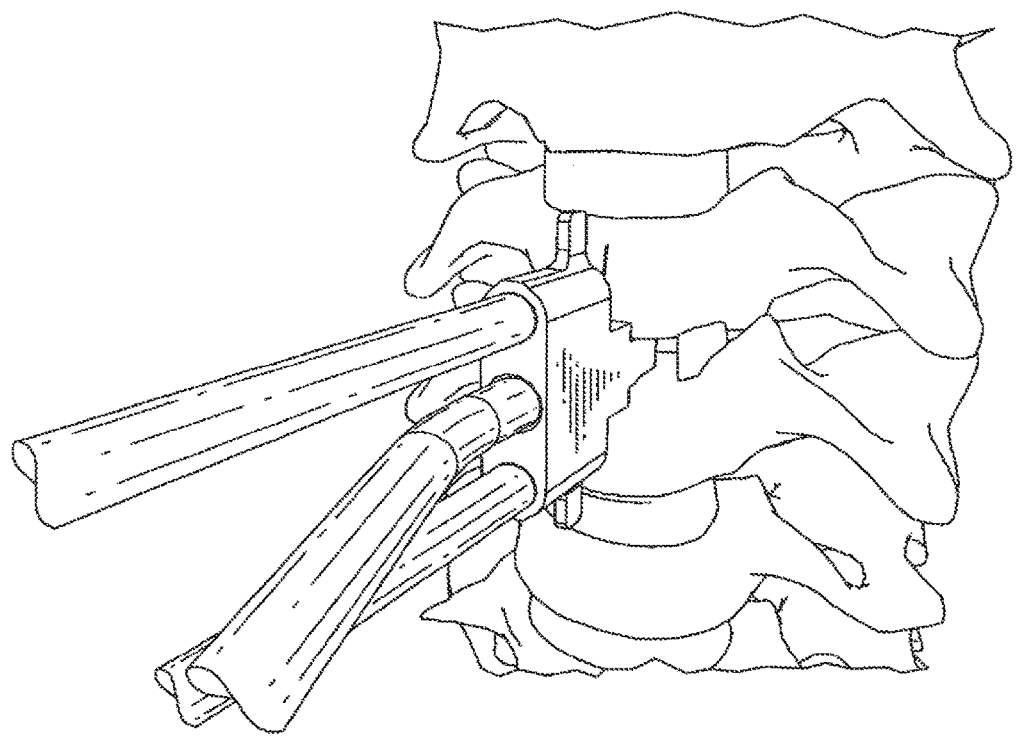

Referring to FIG. 45, after initial preparation of the disc space, reference pins may be attached to the anterior faces of the superior and inferior vertebral bodies. The midline score marks and the tack openings in the superior and inferior vertebral bodies are preferably used for proper placement of the reference pins. Care is preferably taken to ensure proper placement and alignment of the reference pins, which will guide subsequent steps of the procedure. Referring to FIG. 45, the reference pin drill guide described in FIGS. 11A-11D is inserted into the dissected disc space. Specifically, the head at the distal end of the reference pin drill guide is inserted into the disc space between the vertebral bodies. The head at the distal end is inserted until the vertebral body stops abut against the anterior faces of the superior and inferior vertebral bodies. At this stage, one of the openings in the main body of the reference pin drill guide is preferably in alignment with the superior vertebral body and another one of the openings is in alignment with the inferior vertebral body. The reference pin drill guide is preferably aligned with the midline of the vertebral bodies as marked by the score line markings. The alignment of the reference pin drill guide is preferably checked such as by using fluoroscopy. Referring to FIG. 46, with the reference pin drill guide in place, holes are drilled in the superior and inferior vertebral bodies using a drill bit, such as the drill bit shown in FIG. 12 above. FIG. 46 shows a hole being drilled in the superior vertebral body. FIG. 47 shows a hole being drilled in the inferior vertebral body. FIG. 48 shows the target spinal segment after holes have been drilled in both the superior and inferior vertebral bodies.

Figure 49:
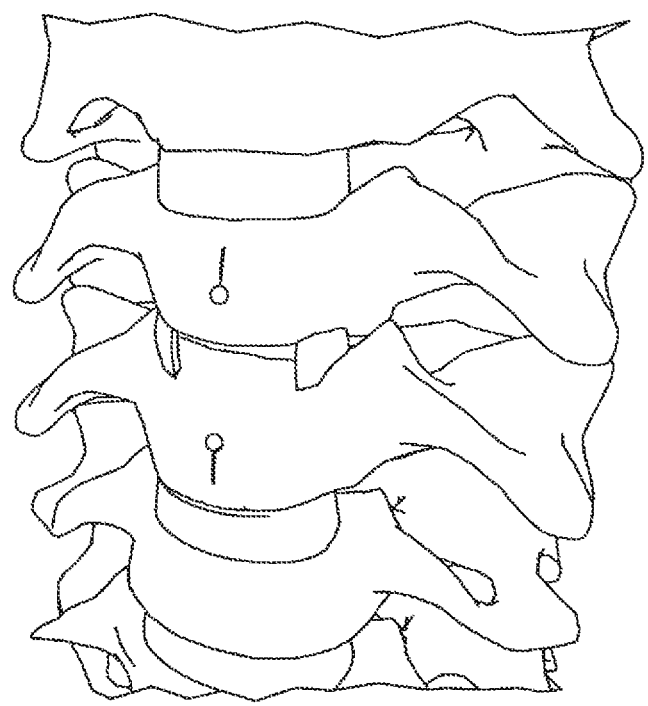

Referring to FIG. 49, after the holes are drilled, the reference pin drill guide is removed from the targeted disc segment. At this stage, a first hole for a first reference pin has been formed in the superior vertebral body and a second hole for a second reference pin has been formed in the inferior vertebral body. The first and second holes in the vertebral bodies are preferably in alignment with the score marks formed previously.

Figure 50:
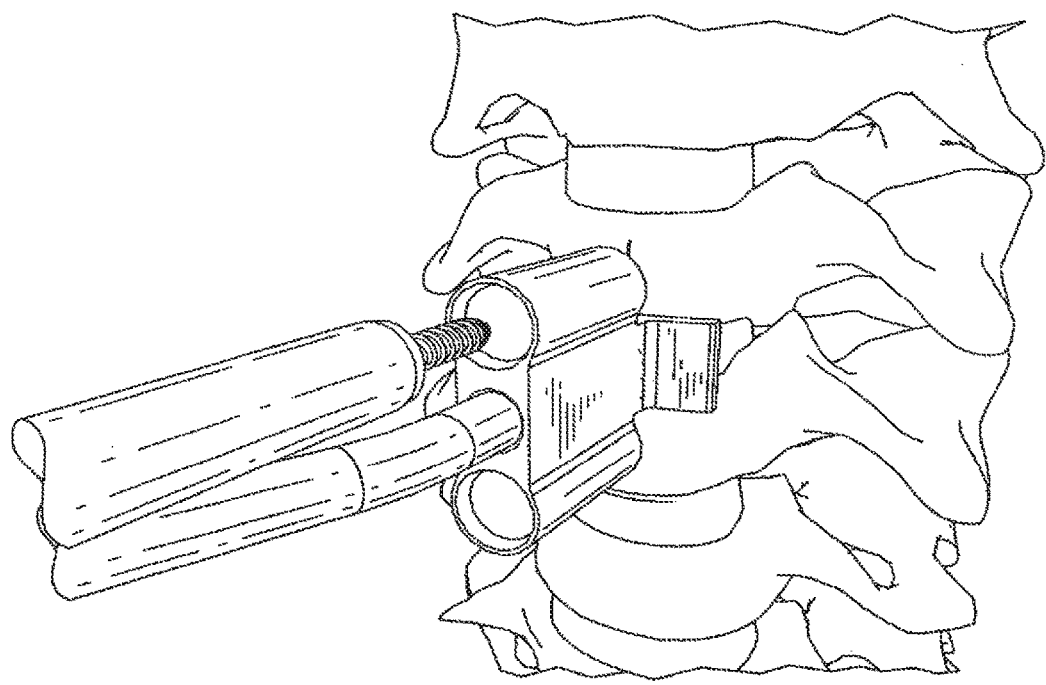

Referring to FIG. 50, the reference pins may be inserted using the reference pin insertion guide shown and described above in FIGS. 14A-14C. Preferably, the head at the distal end of the reference pin insertion guide is inserted into the disc space until the vertebral body stops abut against the anterior surfaces of the superior and inferior vertebral bodies. As shown in FIG. 50, the reference pin insertion guide preferably has a first opening in alignment with the opening formed in the superior vertebral body and a second opening aligned with the opening formed in the inferior vertebral body. A reference pin, such as the reference pin shown and described above in FIGS. 15A-15C is inserted into the first opening of the reference pin insertion guide. The threading at the distal end of the reference pin is threaded into the opening in the superior vertebral body. The reference pin driver shown in FIG. 17A-17C may be utilized for threading the reference pin into the vertebral body. The threads on the reference pins may be self-tapping threads.

Figure 51:
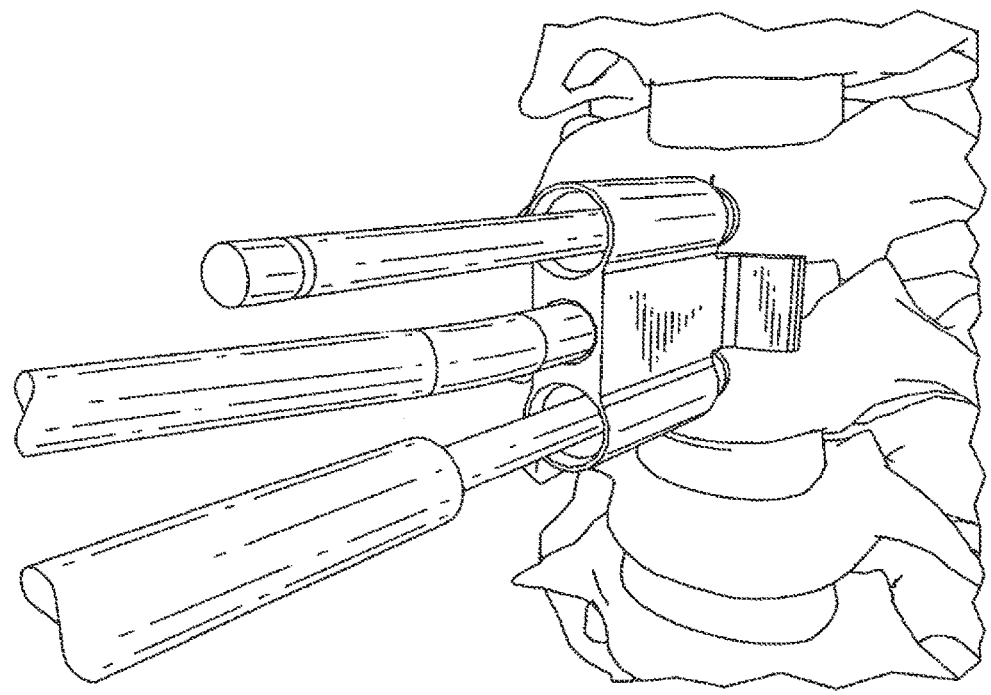

Referring to FIG. 51, after the first reference pin is inserted into bone, the second reference pin is passed through the lower opening in the reference pin insertion guide and driven into the inferior vertebral body using the reference pin driver. In other preferred embodiments, a first reference pin may be attached to the inferior vertebral body before attaching a second reference pin to the superior vertebral body. Thus, the insertion of the reference pins can be accomplished in any particular order.

Figure 52:
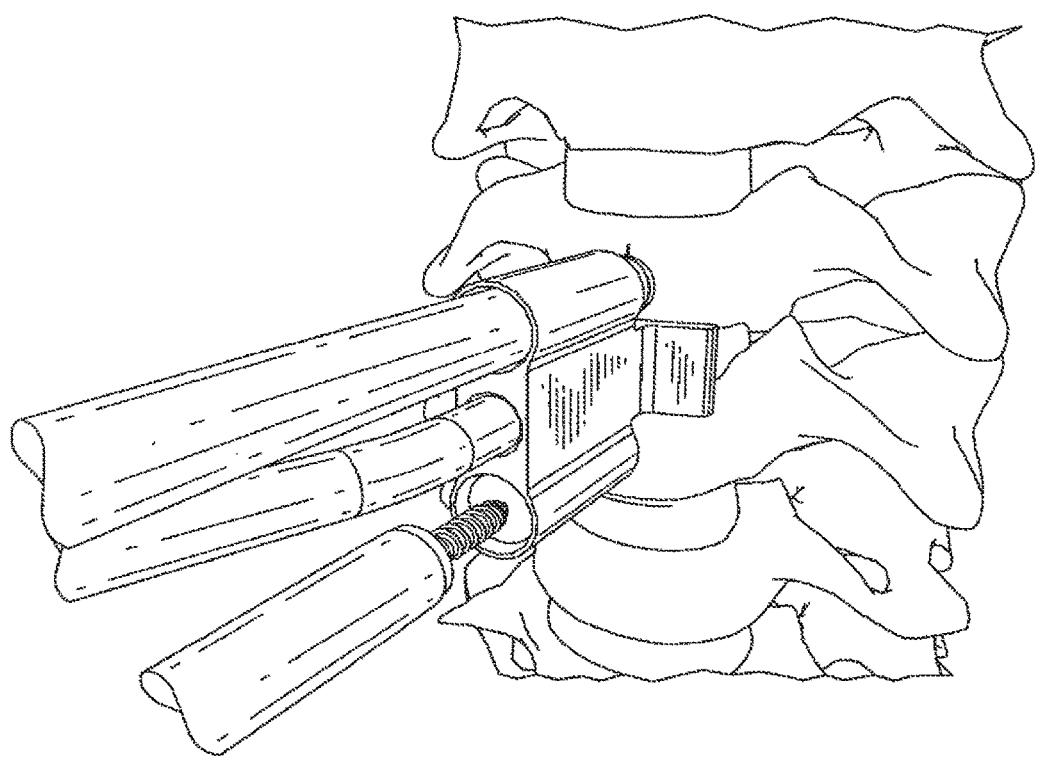

Referring to FIG. 52, in certain preferred embodiments, after a first reference is inserted into bone, a sleeve such as the sleeve shown and described in FIGS. 18A-18B may be slid over the attached reference pin so as to stabilize the reference pin insertion guide. As shown in FIG. 52, the sleeve preferably remains in place to prevent movement of the reference pin insertion guide during insertion of the second reference pin into the other vertebral body.

Figure 53:
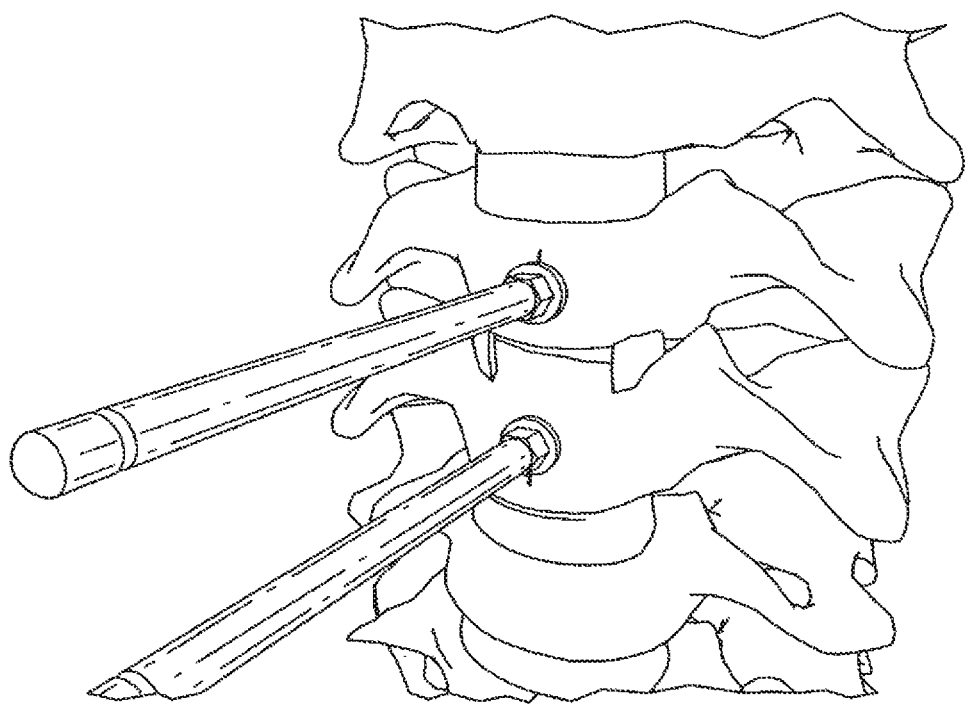

In particular preferred embodiments, different sized reference pins may be used. These different sized reference pins may include shafts having different diameters and/or lengths. In certain preferred embodiments, a small and a large set of reference pins are provided in an instrument tray. The smallest of the pair of reference pins should be inserted initially. If the smaller pair of reference pins proves unsatisfactory, the larger pair of reference pins may be utilized. As shown in FIG. 53, the reference pins are preferably parallel to each other and in alignment with the midline of the superior and inferior vertebral bodies.

Figure 54:
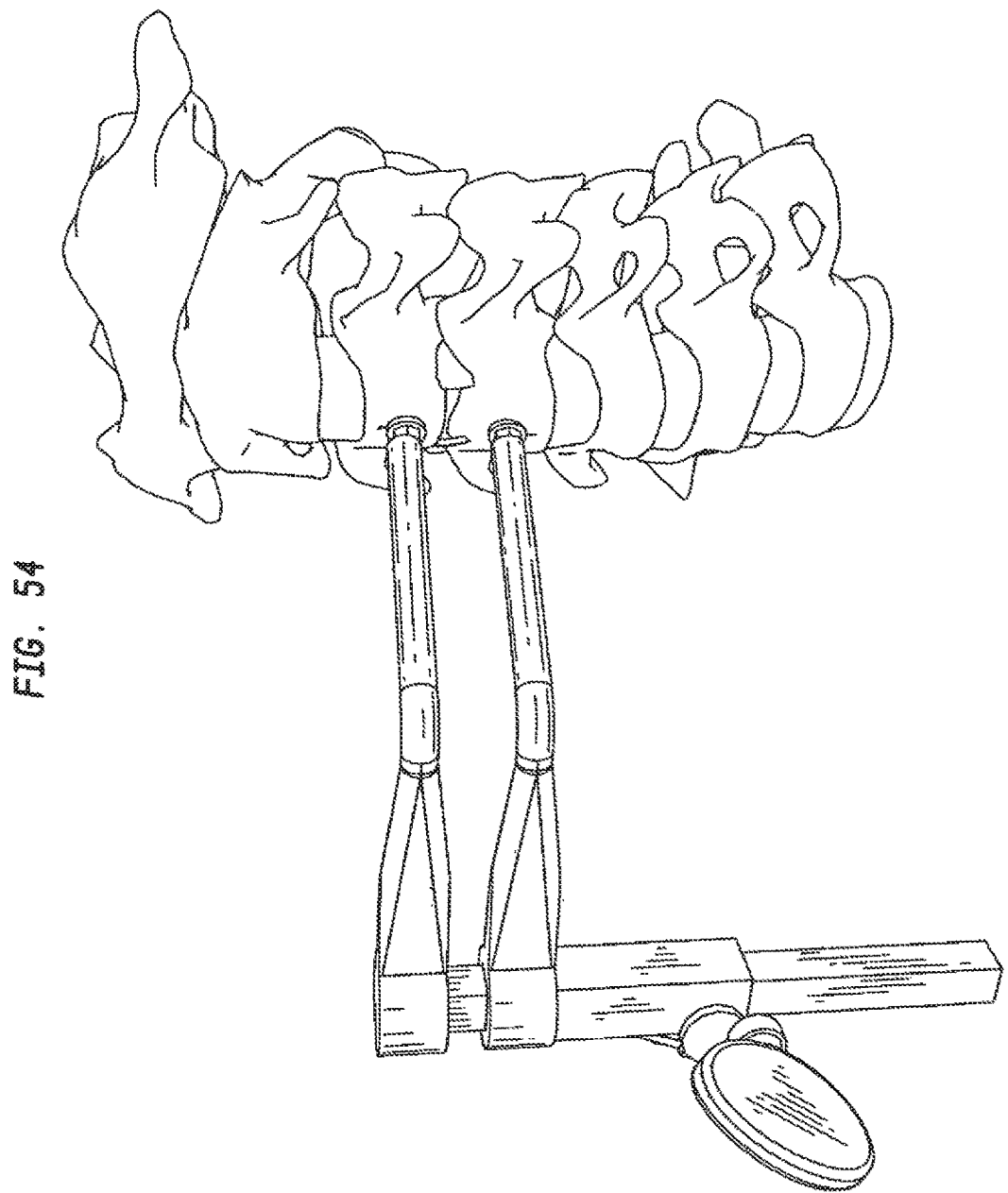

Once the reference pins are in place, a surgeon may preferably apply distraction to the disc space by using a distraction tool, such as a distractor as shown and described in FIGS. 19A-19C. Once distraction has occurred, the disc space may be cleared of any extraneous matter and restored to a desired height. Prior to distraction, the facets of the targeted spinal segment should be reviewed under fluoroscopy in order to monitor facet orientation during distraction. The distractor shown in FIGS. 19A-19C is preferably placed over the reference pin shown in FIG. 53. FIG. 54 shows the distractor after it has been placed over the reference pins. If the reference pins loosen at any time during the distraction procedure, the reference pins may be removed and replaced with the larger reference pins provided in the instrument set.

The distractor is then utilized to apply distraction to the targeted spinal segment. During the distraction procedure, the facets and the disc space are preferably monitored under fluoroscopy to ensure a complete distraction. The amount of distraction should not exceed the height of the adjacent disc space. As noted above, fluoroscopy should be used to monitor the distraction height so as to prevent over-distraction. As is well known to those skilled in the art, over-distraction may cause nerve and/or facet damage.

After the targeted spinal segment has been distracted, the discectomy procedure is completed. In preferred embodiments, the posterior and lateral margins of the disc space are cleared of any extraneous matter. The clearing of the posterior and lateral margins preferably extends to the uncinate processes and all the way back to the nerve root and canal. In certain preferred embodiments, lateral fluoroscopy is utilized to check the anterior aspects of the vertebral body for osteophytes. A cutting tool, such as a burr, may be used to further prepare the endplates of the opposing superior and inferior vertebral bodies. The cutting tool may be utilized to smooth out the curvature of the superior endplate. After the discectomy has been completed, the endplates of the adjacent vertebral bodies are preferably parallel to one another and relatively uniform, thereby preventing undersizing of the implant.

In certain preferred embodiments, the decompression of the targeted disc space may be completed by removing any posterior osteophytes or soft tissue material that may inhibit the full distraction of the posterior portion of the targeted disc space. In certain preferred embodiments, it may be necessary to remove the posterior longitudinal ligament (PLL) to achieve optimal restoration of the disc height, decompression and release for post-operative motion. In addition, the posteriolateral corners of the endplates may be resected as needed to provide neural decompression. In certain instances, it may be necessary to remove the posteriolateral uncovertebral joints. The lateral uncovertebral joints are preferably not removed unless they are causing nerve root compression. In addition, in certain preferred embodiments it may be necessary to perform a foraminotomy if there are symptoms of neural/foraminal stenosis.

Figure 55:
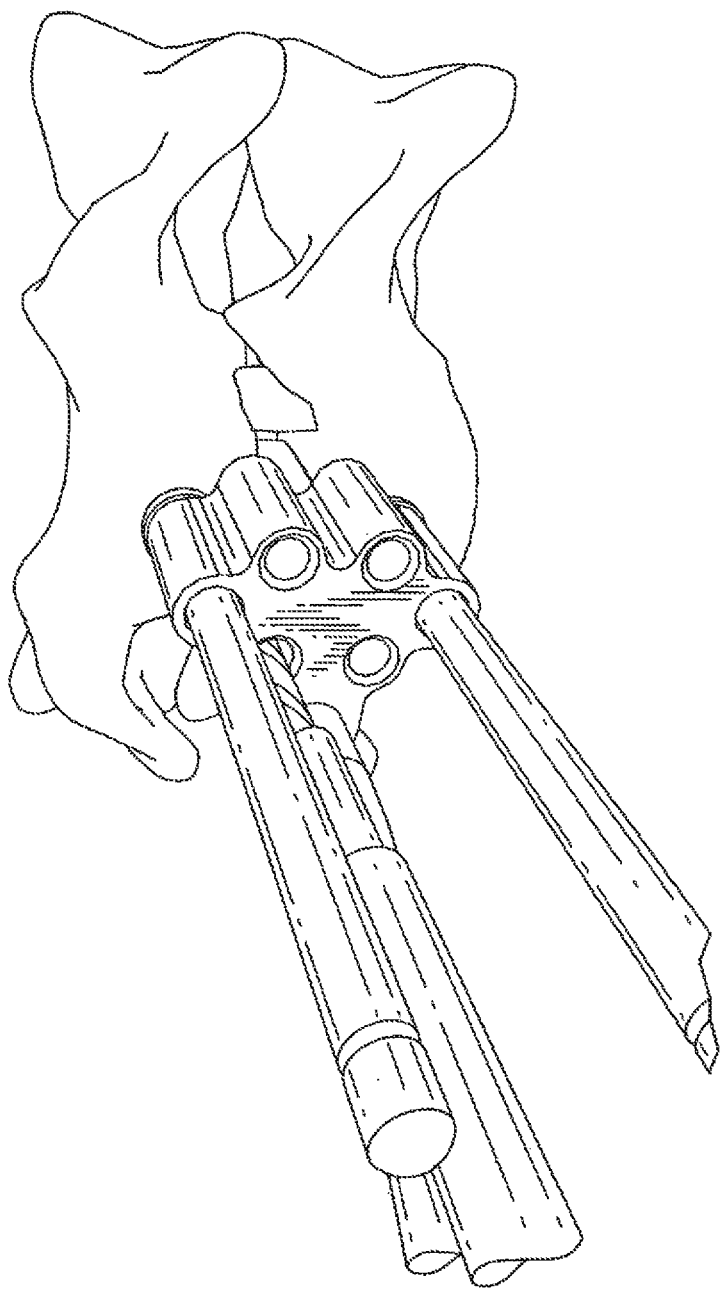

In certain preferred embodiments, another stage of the intervertebral disc implantation method involves initial endplate preparation including drilling pilot grooves in the superior and inferior vertebral bodies. After complete distraction has taken place, the distractor shown in FIG. 54 is removed. Referring to FIG. 55, the protrusion drill guide of FIGS. 20A-20D is inserted into the prepared disc space. The openings at the upper and lower ends of the drill guide are aligned with the proximal ends of the reference pins. As shown in FIG. 55, the reference pins engage the openings for guiding the drill guide toward the prepared disc space. The head at the distal end of the drill guide is inserted into the prepared disc space until the vertebral body stops abut against the anterior faces of the superior and inferior vertebral bodies. In preferred embodiments, the surgeon should visually check that the vertebral body stops of the drill guide come into full contact with the superior and inferior vertebral bodies. The handle of the drill guide is preferably parallel with the inferior and superior endplates and aligned in the sagittal plane.

As shown in FIG. 55, a drill bit is utilized to drill four pilot holes for the implant protrusions at precise locations in the vertebral bodies. As shown in FIG. 55, the drill guide includes two openings for drilling a pair of pilot holes in the superior vertebral body and two openings for drilling pilot holes in the inferior vertebral body. In certain preferred embodiments, the drill includes a stop to limit the length of the pilot holes. In particular preferred embodiments, there is a stop on the drill so as to ensure that the pilot holes are no more than 10 mm in length.

Figure 56:
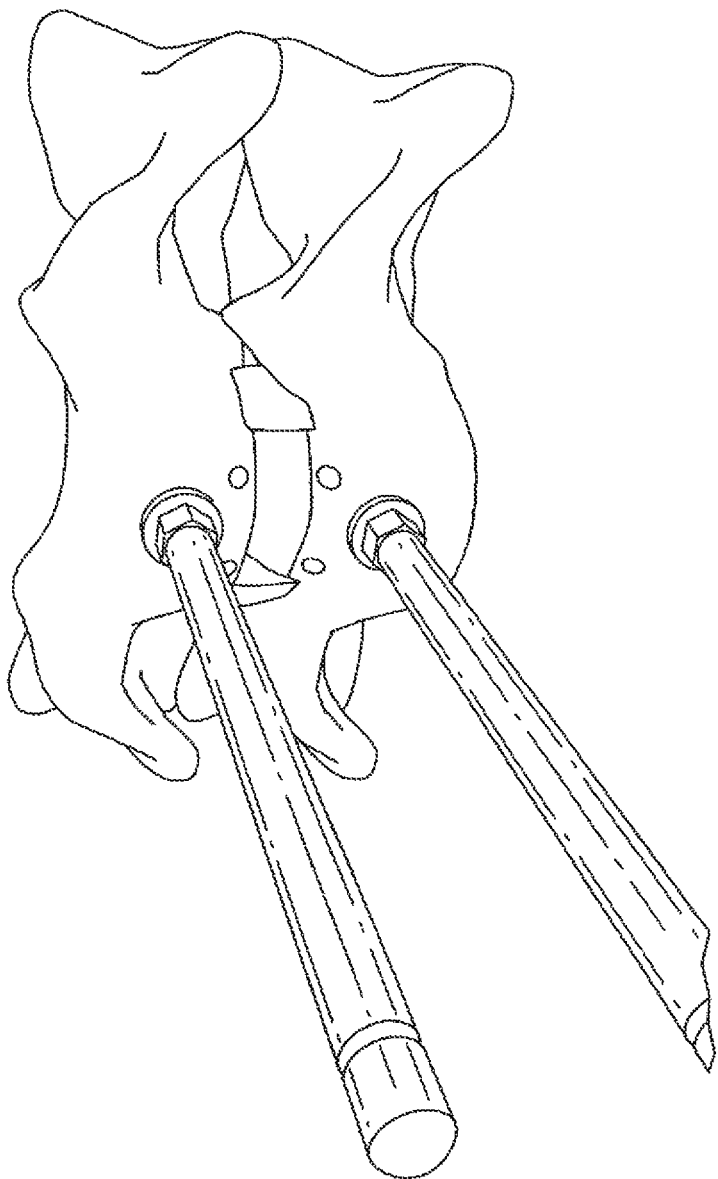

Referring to FIG. 56, after the pilot holes have been formed in the superior and inferior vertebral bodies, the drill guide is retracted from the targeted disc space and decoupled from the two reference pins. As shown in FIG. 56, two pilot holes are formed in the superior vertebral body and two pilot holes are formed in the inferior vertebral body. The two pilot holes on the left of the adjacent vertebral bodies are preferably in vertical alignment with one another and the two pilot holes on the right of the vertebral bodies are preferably in vertical alignment with one another.

Figure 57:
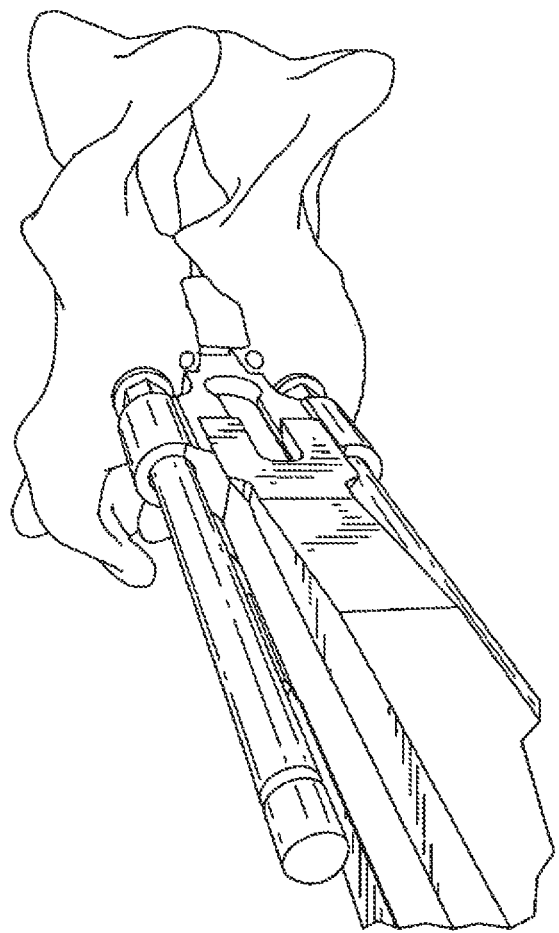

In certain preferred embodiments, channels for the protrusions of the intervertebral disc implant are formed in the endplates of the superior and inferior vertebral bodies. Referring to FIG. 57, the chisel guide shown and described in FIGS. 21A-21D is inserted into the targeted disc space. The alignment openings in the chisel guide are slid over the reference pins. The head at the distal end of the chisel guide is inserted into the targeted disc space until the vertebral body stops come into contact with the anterior surfaces of the vertebral bodies. The handle of the chisel guide is preferably parallel with the superior and inferior endplates and aligned in the sagittal plane. As shown in FIG. 55, the chisel described in FIGS. 22A-22D is coupled with one of the tracks of the chisel guide and advanced toward the disc space. The cutting blades of the chisel are preferably advanced toward the superior and inferior vertebral bodies while positive pressure is applied to the chisel guide to ensure that it does not back out of the disc space. FIG. 23 shows the chisel 374 coupled with the chisel guide 350 with the cutting blades at the distal end of the chisel opposing the superior and inferior vertebral bodies. A striking instrument, such as the mallet shown and described in FIGS. 24A-24B, may be utilized to strike the distal end of the chisel so as to cut channels in the superior and inferior vertebral bodies.

Figure 58:
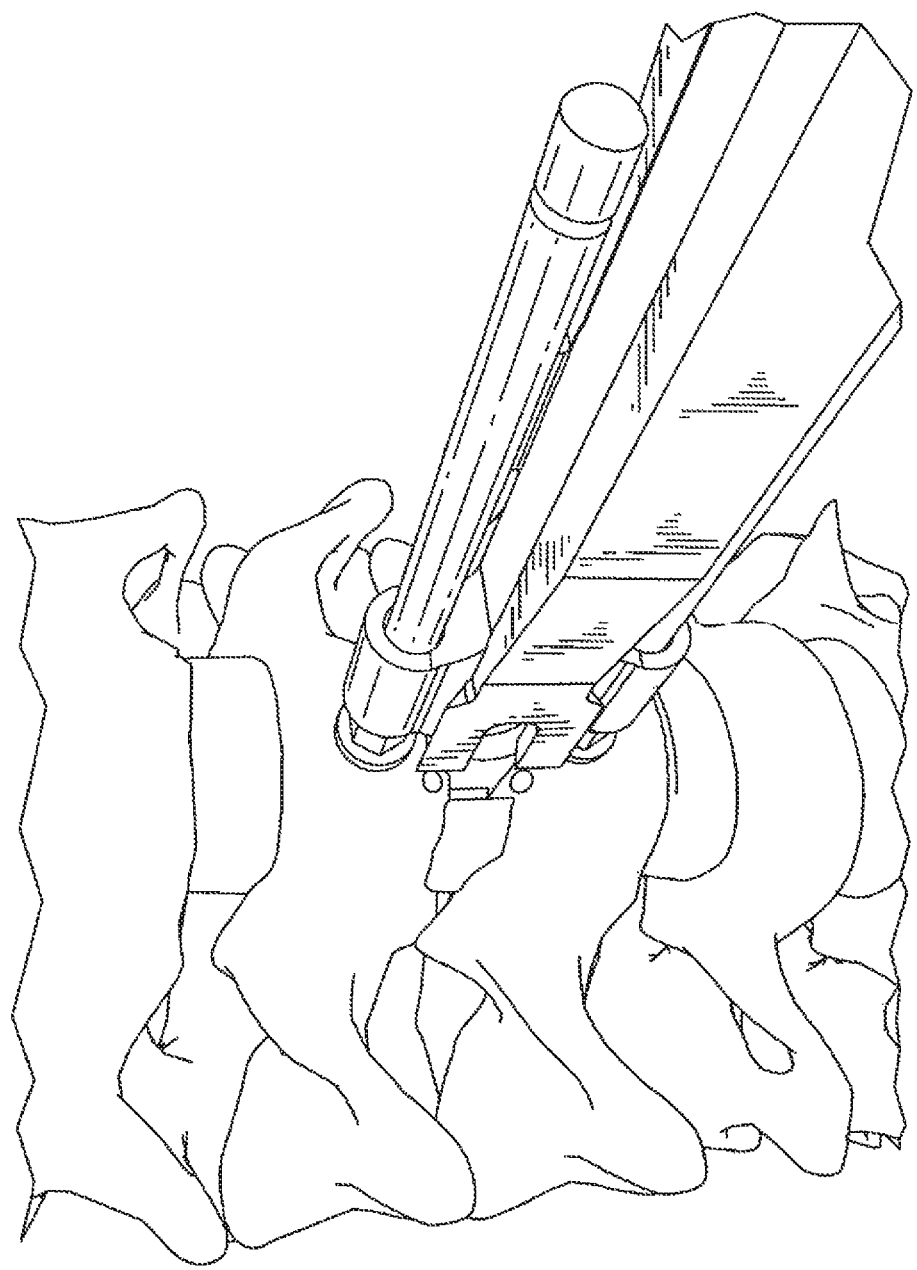
Figure 59:
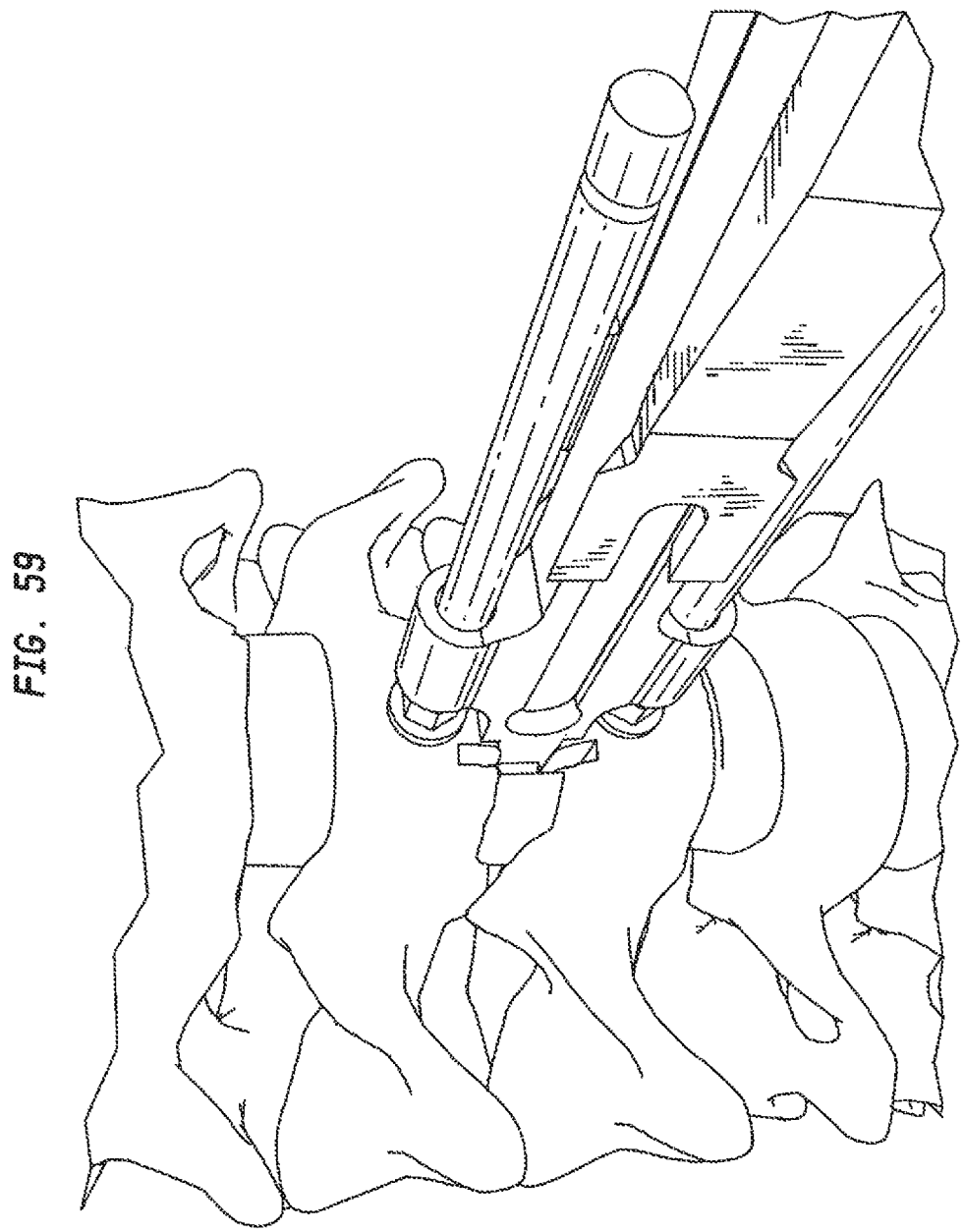
Figure 60:
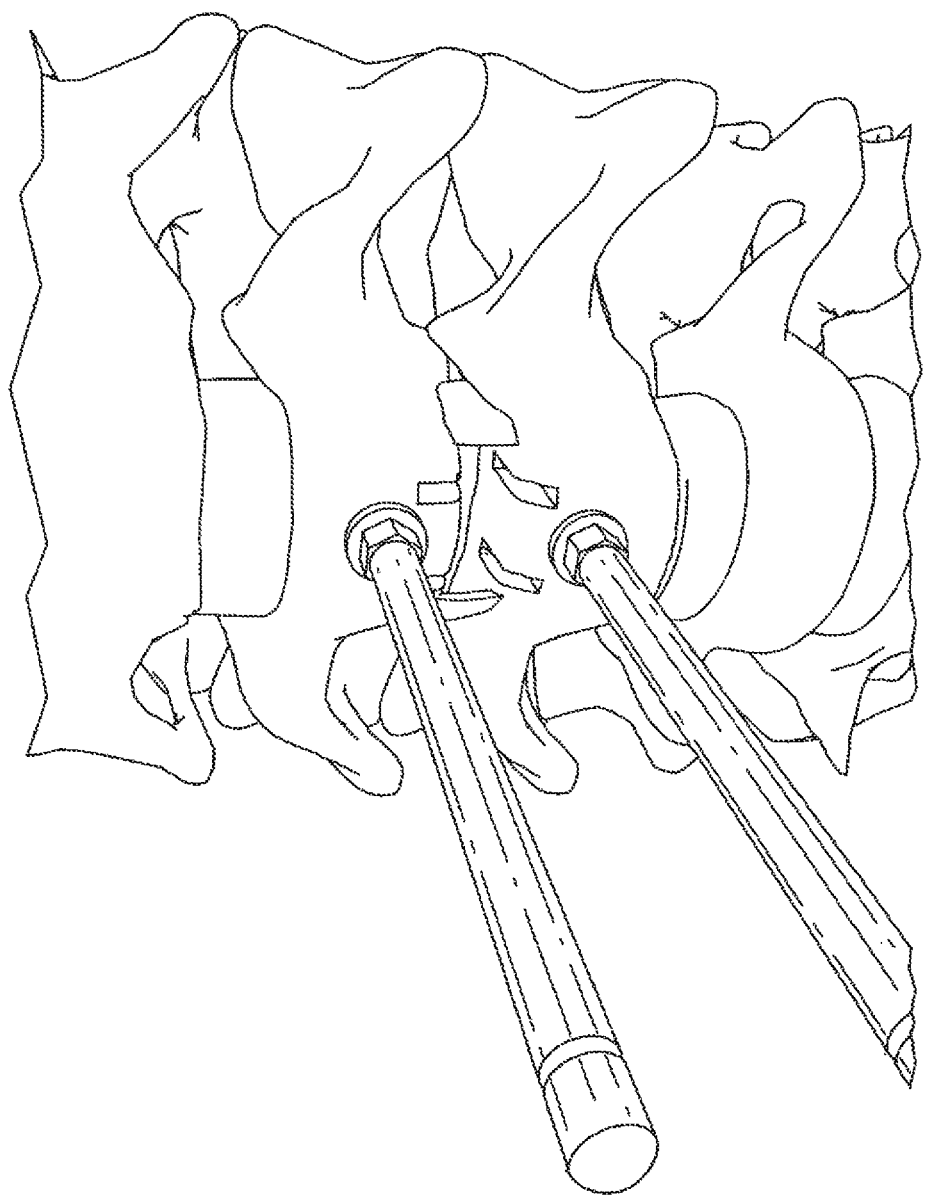

Referring to FIG. 58, after the first chisel has cut the channels on one side of the chisel guide, a second chisel is preferably utilized in the same manner as described above with respect to the first chisel to cut a second set of channels in the vertebral bodies. FIG. 59 shows the targeted spinal segment after a set of channels has been cut into the superior and inferior vertebral bodies. FIG. 60 shows the targeted spinal segment after the channels have been cut in the vertebral bodies and the chisel guide has been removed from the reference pins.

Figure 61:
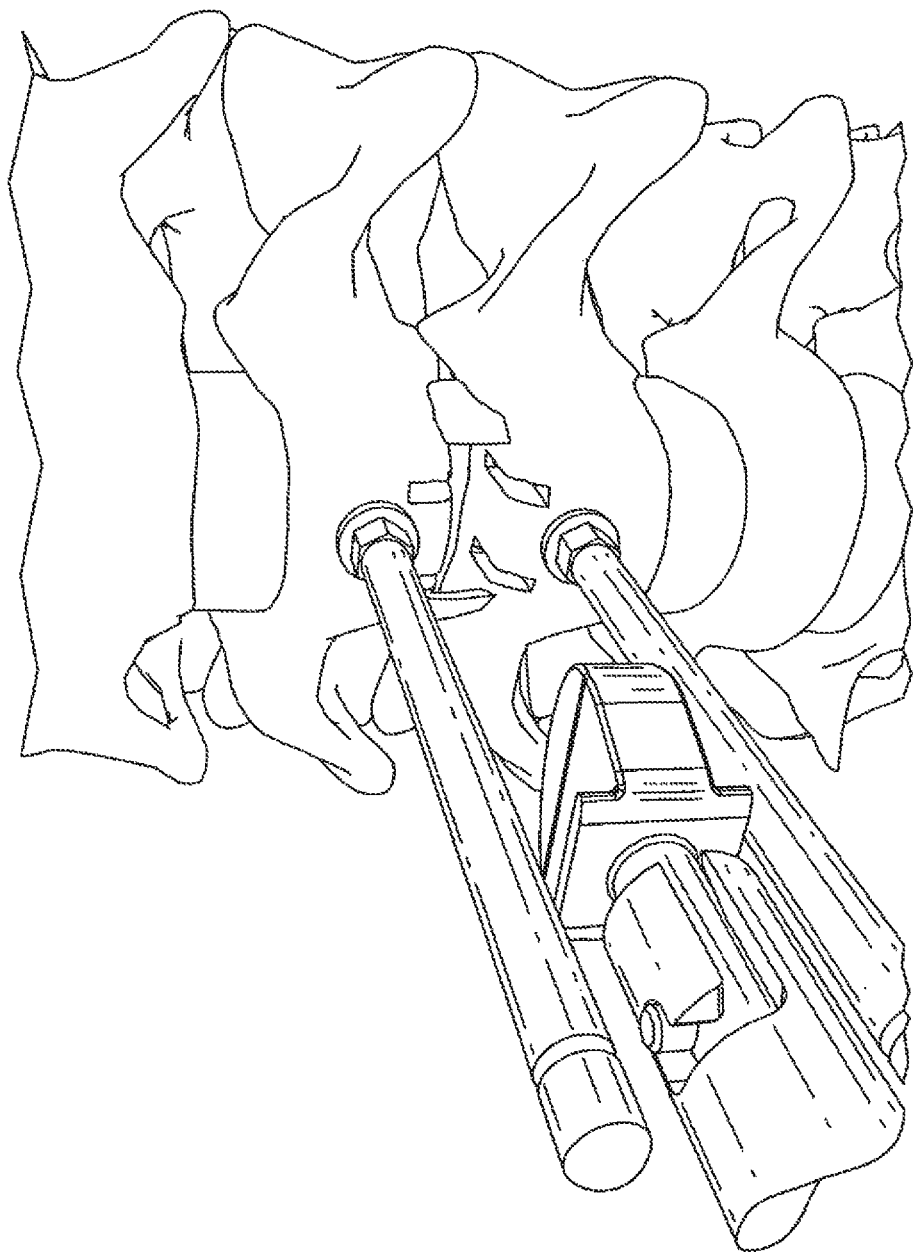
Figure 62:
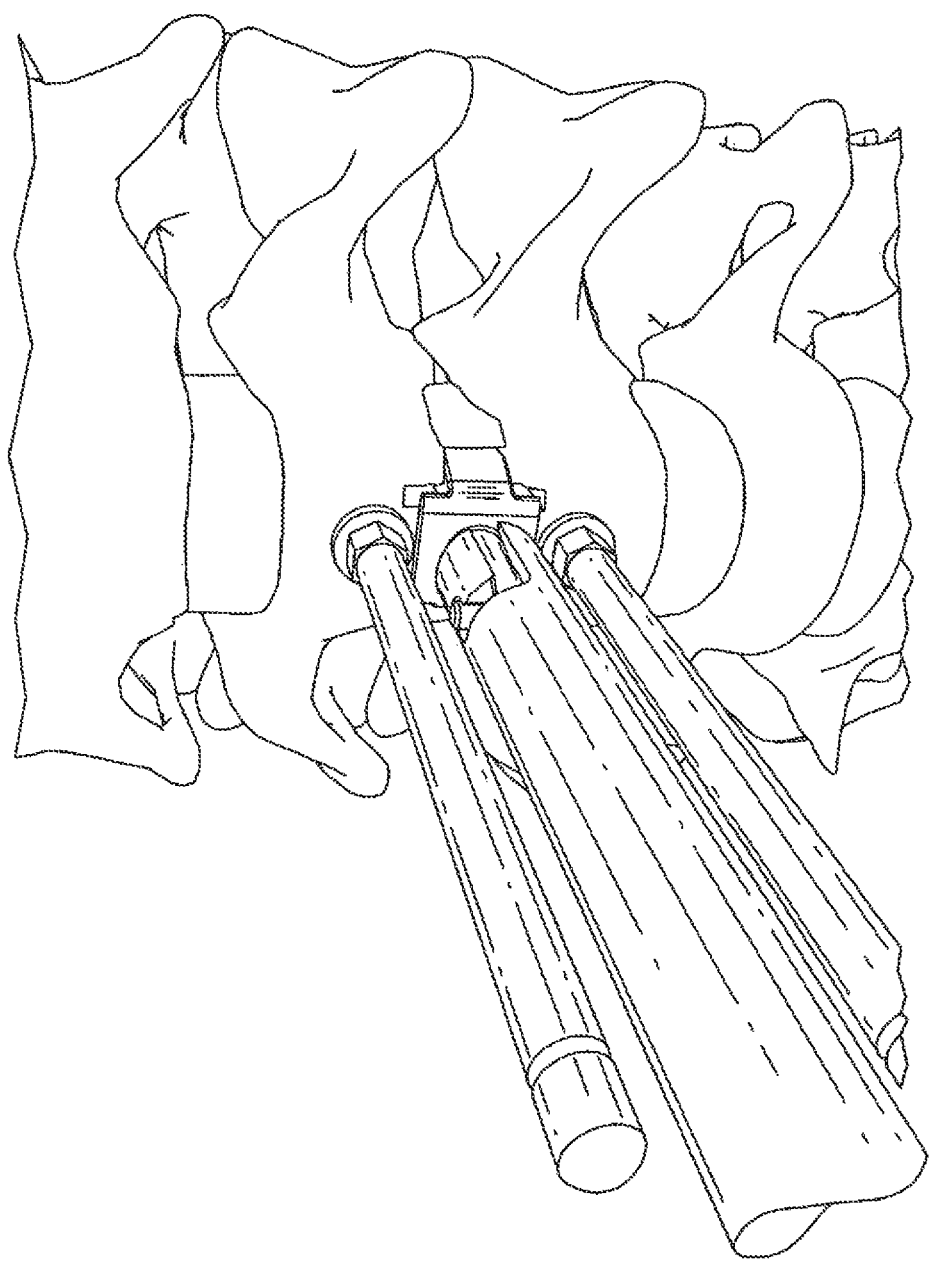

In certain preferred embodiments, a sizing operation is conducted to determine the proper size of the intervertebral disc that will be placed into the targeted disc space. Referring to FIG. 61, a sizer such as the sizer shown and described above in FIGS. 25A-26B may be inserted into the disc space. The sizers may have different heights (e.g., 5-9 mm) and different base plate widths (e.g., 14 mm and 16 mm). In preferred embodiments, a sizer having a height of 5 mm is used initially. The sizer is preferably attached to the handle shown and described above in FIGS. 26A-26D. The sizer is then advanced into the disc space as shown in FIG. 62. The sizer is preferably advanced until the vertebral body stops on the sizer abut against the anterior surfaces of the superior and inferior vertebral bodies.

After starting with a sizer having a height of 5 mm, sequentially larger sizers are utilized to determine the desired implant height that will best fit into the disc space without over tensioning the annulus. The correct height for the sizer is preferably determined when the sizer fits snugly into the disc space with mild to moderate resistance to retraction of the sizer. The width of the disc space may also be checked by using a sizer having a different width and inserting the sizer into the disc space. In certain preferred embodiments, the sizer may include alignment openings that engage the reference pins for guiding the sizer as it is advanced toward the disc space.

Figure 63:
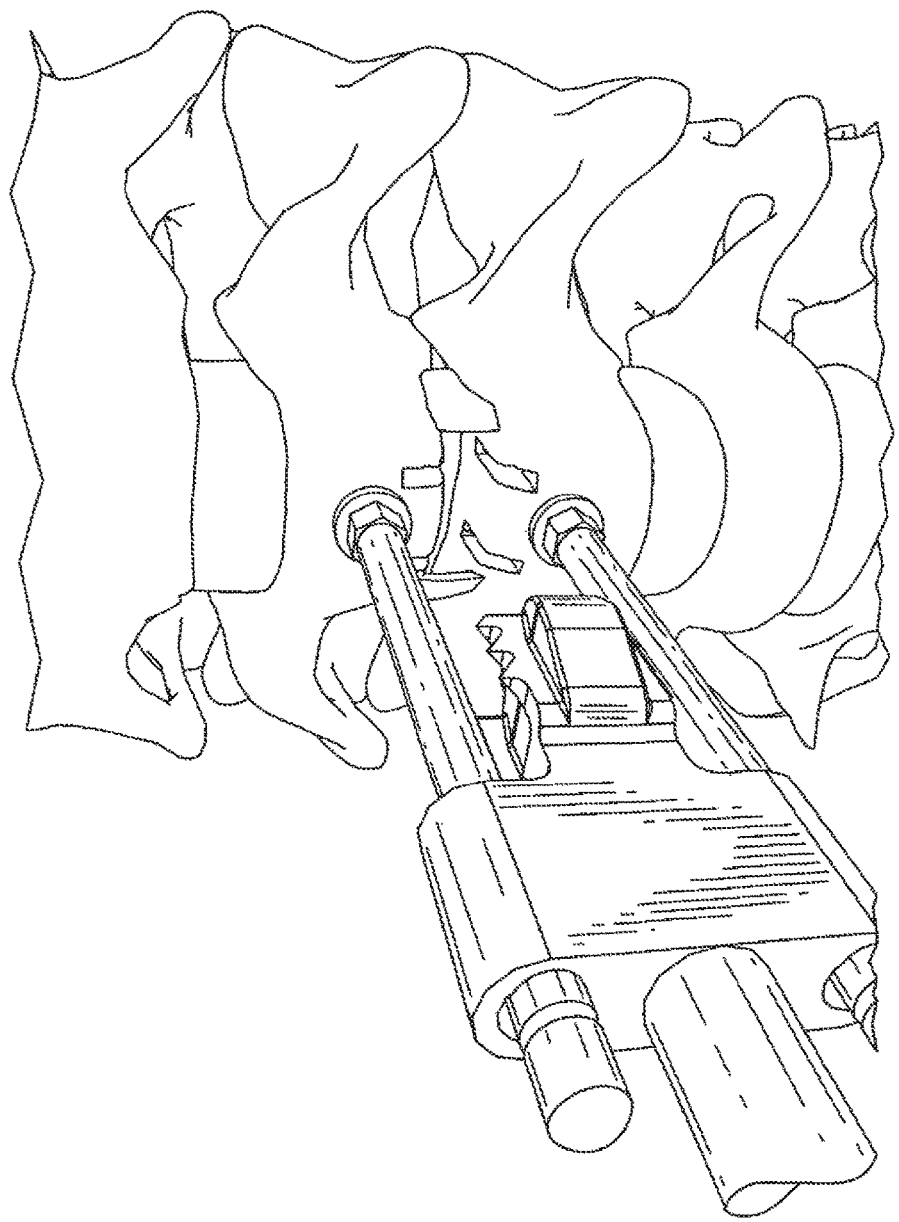

In certain preferred embodiments, a trial is inserted into the disc space to complete preparation of the channels for the protrusions of the intervertebral disc. Referring to FIG. 63, a trial such as that shown and described above in FIGS. 28A-28D is advanced toward the disc space. As described above, the trial includes alignment openings that are slid over the reference pins for guiding advancement of the trial. The particular size of the trial is selected based upon the corresponding size of the sizer that produced the best fit within the disc space. In certain preferred embodiments, the particular trial selected is based upon the following chart:

| Sizer | Trial Size |
| --- | --- |
| 5-6 mm height 14 mm × 12 mm baseplate | Small, 14 mm |
| 7-9 mm height 14 mm × 12 mm baseplate | Large, 14 mm |
| 5-6 mm height 16 mm × 14 mm baseplate | Small, 16 mm |
| 7-9 mm height 16 mm × 14 mm baseplate | Large, 16 mm |

Figure 64:
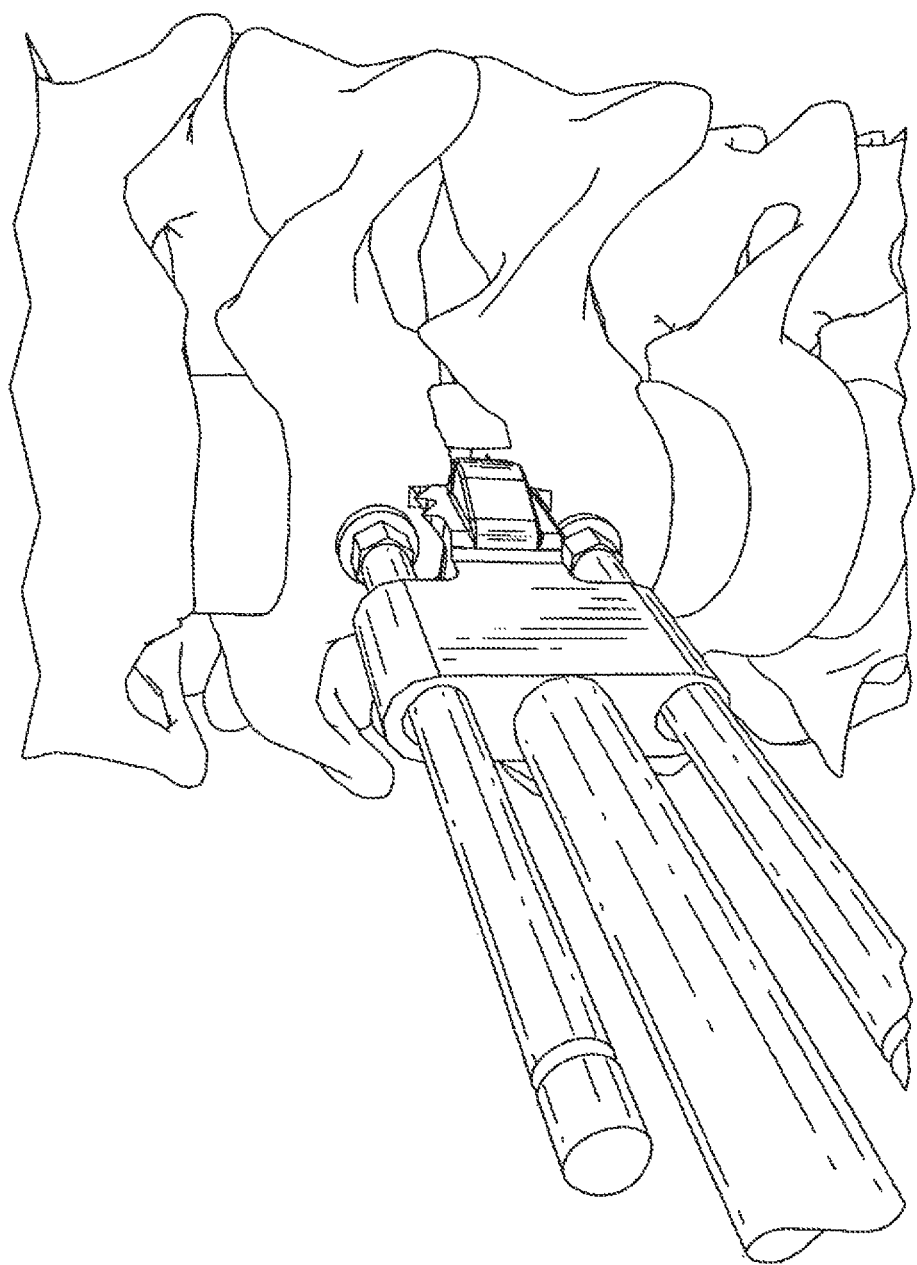

Referring to FIG. 64, the trial is advanced along the reference pins and into the intervertebral space. The protrusions on the trial are preferably aligned with the channels previously formed in the opposing endplates. A mallet may be impacted against the proximal end of the trial for advancing the trial into the disc space. If necessary, a slap hammer may be utilized to remove the trial from the disc space. In preferred embodiments, the trial is inserted at an angle that is parallel to the endplates so as to prevent damage to the endplates and avoid creating bone fragments. One or more trials may be inserted into the disc space until a proper fit is achieved.

Figure 65:
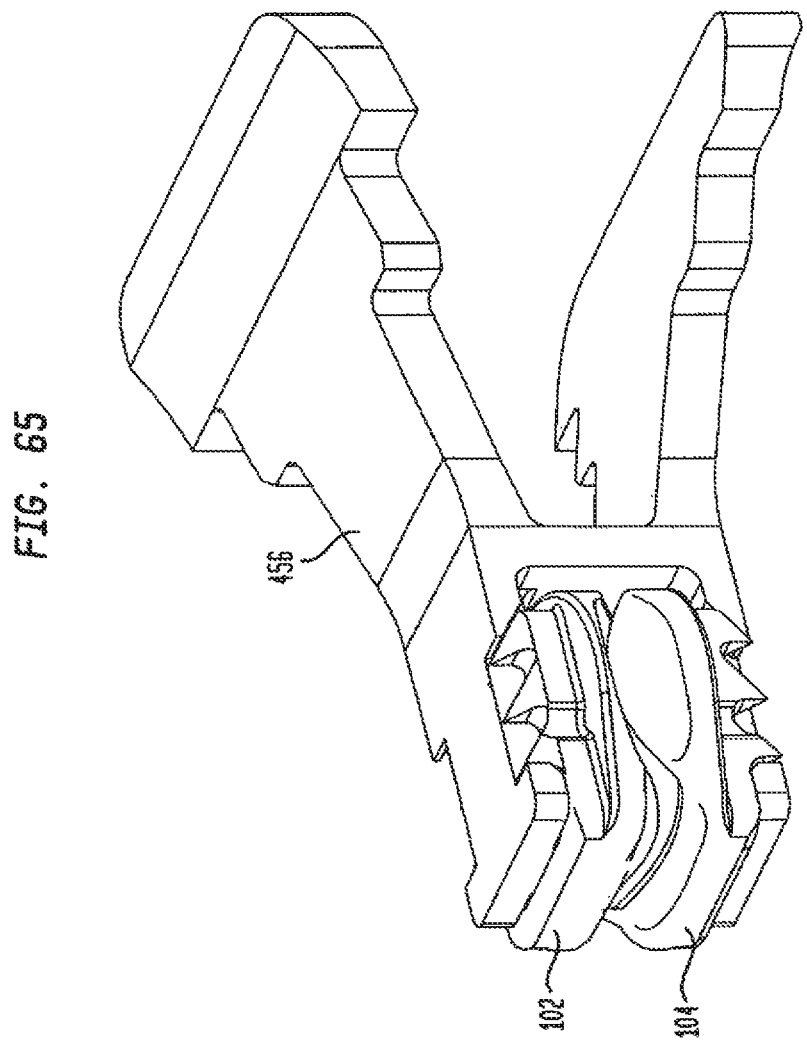

In certain preferred embodiments, an appropriately sized intervertebral disc implant is then selected and inserted into a targeted disc space. Referring to FIG. 65, in certain preferred embodiments, the intervertebral disc implant is provided as a single unit with the top and bottom elements of the implant being held together by an implant dispenser 456. In preferred embodiments, the implant dispenser is color coded to correspond to the height of the implant. In addition, the implant dispenser is preferably marked with the height of the implant and the width of the top and bottom elements. The outer surface of the implant may also be marked with the height and width of the implant. In particular preferred embodiments, the anterior face of the implant is marked with the height and width of the implant.

In preferred embodiments, prior to insertion of the intervertebral disc implant, the size label on the implant is inspected and the size label on the implant dispenser is also inspected to ensure that the correctly sized implant was selected and that the top or superior element of the implant is oriented for proper insertion. In preferred embodiments, an implant is selected having a height and baseplate dimensions that match the corresponding sizer that restored the desired height of the disc space without over-tensioning the annulus or damaging the facets.

After an appropriately sized intervertebral disc implant has been selected, an inserter head, such as the inserter head shown and described above in FIGS. 30A-30B, is selected. The selected inserter head preferably has a height and/or dimensions that match the particular dimensions of the selected implant and selected implant dispenser. Thus, the inserter head may also be color coded to correspond to the height of the implant and the particular dimensions of the implant dispenser. The inserter head may be a single use component that is discarded after the implantation procedure. In certain preferred embodiments, each inserter head may be used for either a 14 mm or 16 mm width implant that is preferably matched to the implant height.

Figure 66:
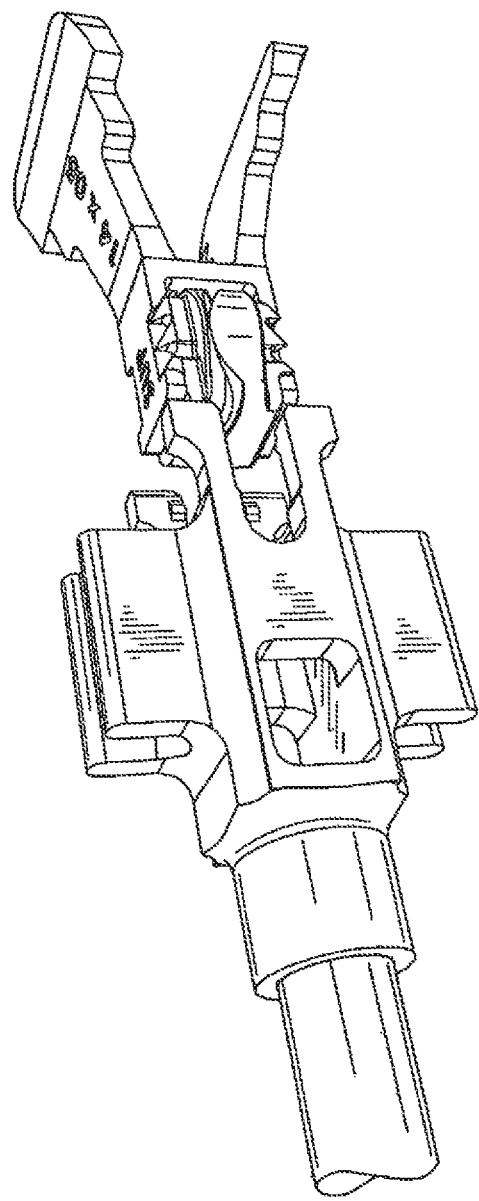
Figure 67:
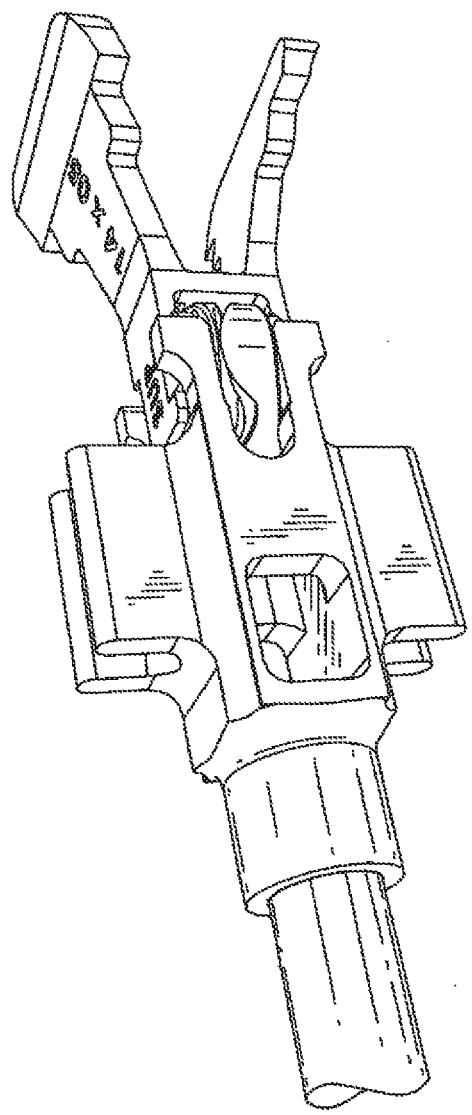

Referring to FIGS. 66 and 67, the implant and implant dispenser are juxtaposed with the distal end of the inserter head.

In certain preferred embodiments, the inserter head is attached to a handle. The attachment may include a threaded attachment whereby a t-bar or handle is rotated to threadably engage the inserter head with the handle.

Referring to FIG. 67, in certain preferred embodiments, the implant is attached to the inserter head by first matching the superior and inferior labels on the implant dispenser with the inserter head. The four arms of the inserter head are then slid along the outer lateral sides of the implant protrusions. The inwardly extending projections on the arms are preferably engaged with the depressions formed in the outer lateral sides of the protrusions. The implant is preferably secured to the inserter head when the projections are seated in the depressions in the outer lateral sides of the protrusions. Once the implant has been secured to the inserter head, the implant dispenser may be decoupled from the implant. Once secured, the posterior part of the implant preferably extends beyond the ends of the arms of the inserter head. The implant dispenser may then be detached from engagement with the implant.

Figure 68:
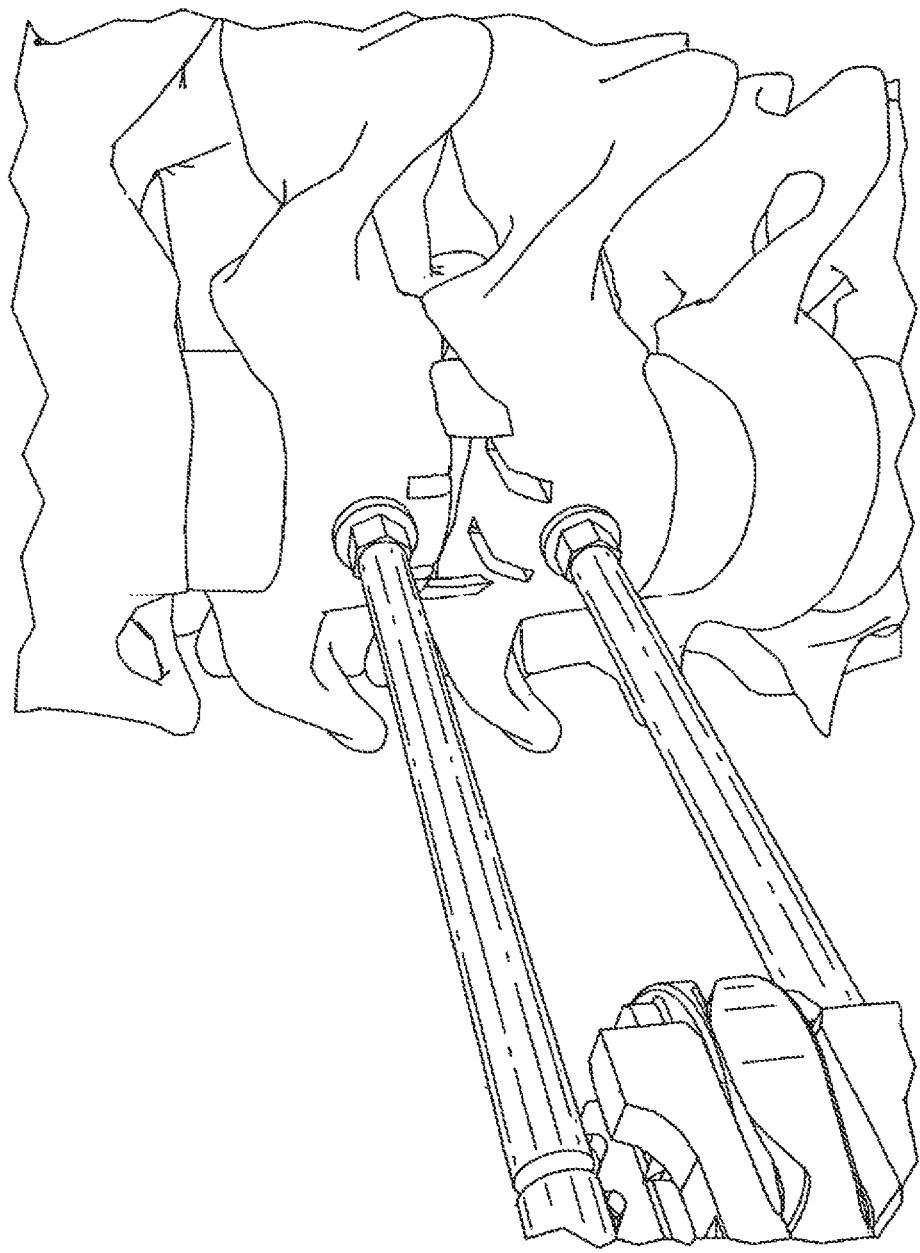
Figure 69:
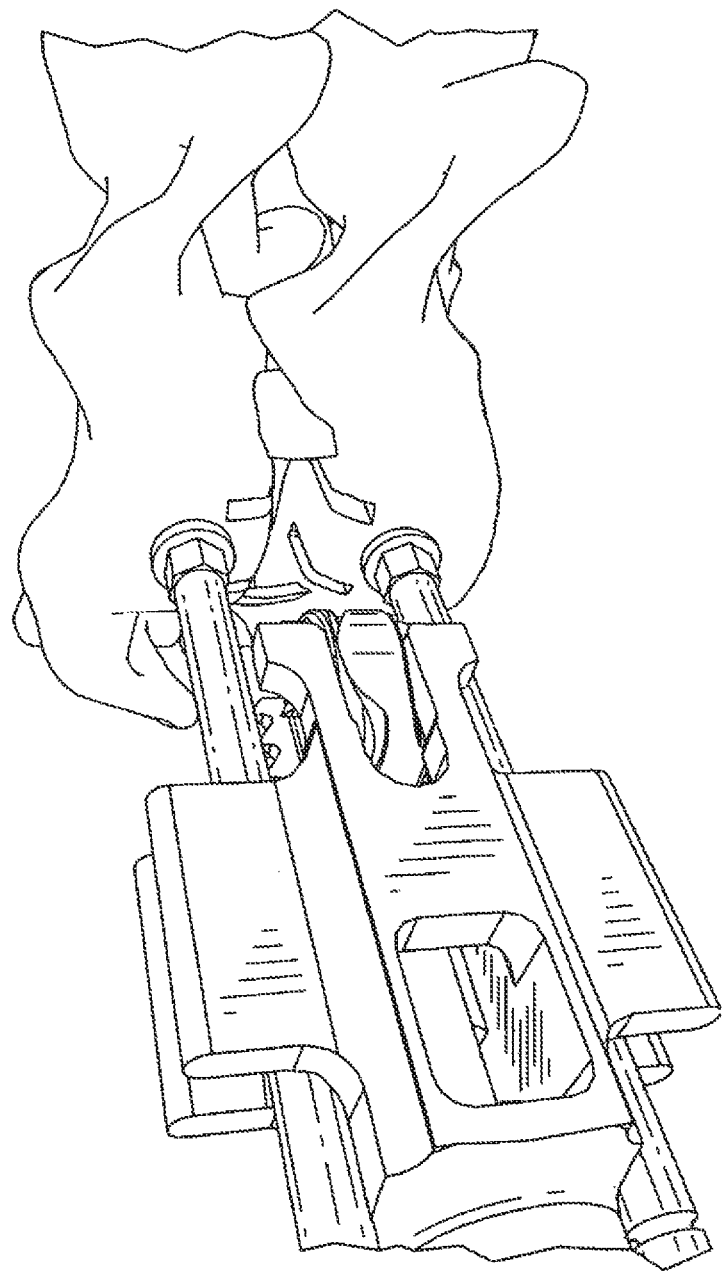

In certain preferred embodiments, the intervertebral disc implant is inserted into a prepared disc space. Referring to FIGS. 68 and 69, the inserter head is properly oriented with the disc space. In preferred embodiments, the inserter head includes at least one label or marking that is oriented relative to the superior or inferior vertebral bodies. Preferably, a superior label of the inserter head is oriented on top and an inferior label is oriented on the bottom. The reference pins are then utilized to guide the inserter head toward the disc space. The guide channels formed at the top and bottom of the inserter head preferably engage the reference pins. Referring to FIG. 69, as the intervertebral disc is advanced toward the disc space, the implant protrusions are preferably aligned with the protrusion channels previously formed in the endplates. In certain preferred embodiments, fluoroscopy is utilized to check the angle of insertion of the implant. The inserter head is preferably advanced toward the disc space until the four arms of the inserter head come into contact with the anterior surfaces of the vertebral bones.

Figure 70:
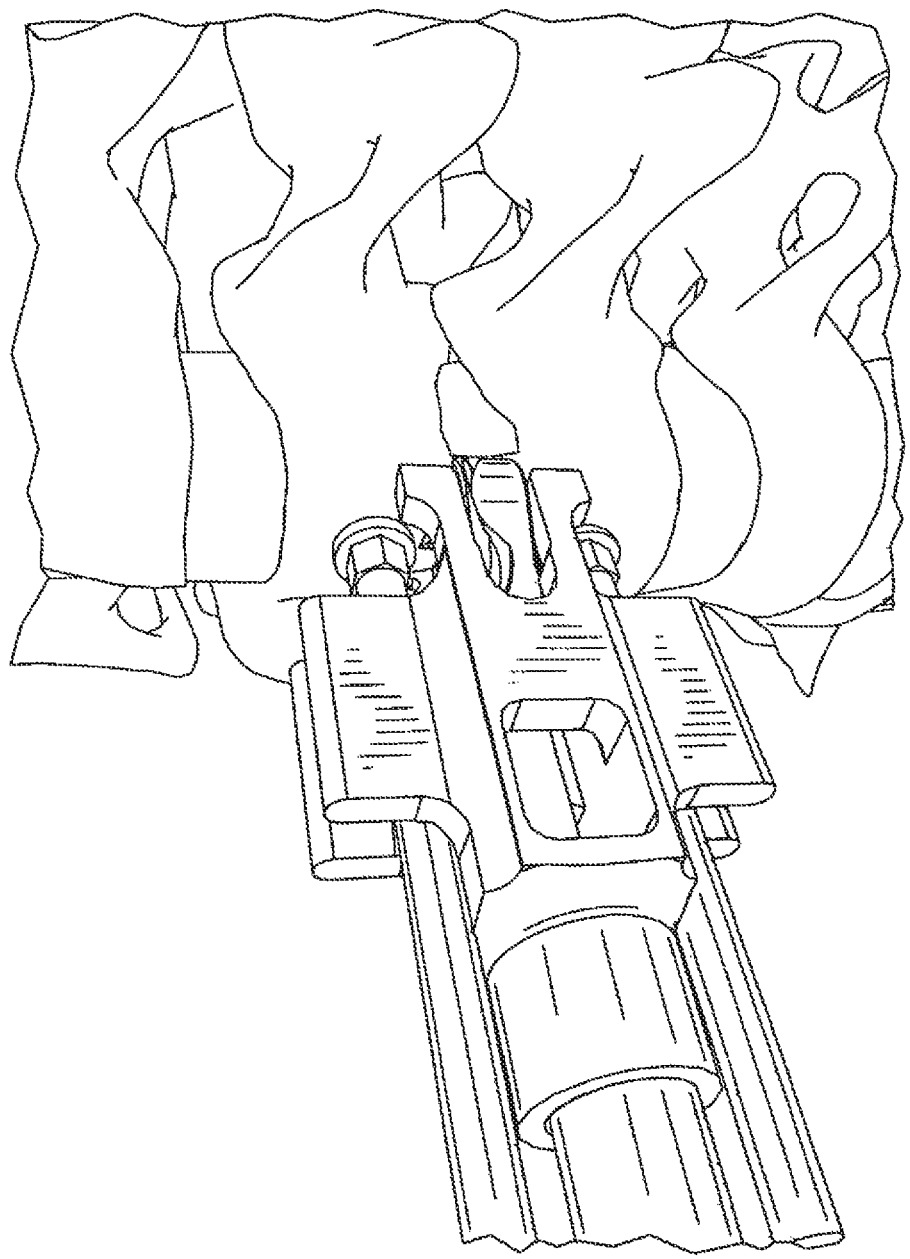

Referring to FIG. 70, a T-handle 496 (FIG. 31) may then be rotated for advancing a pusher rod 494 which pushes the implant off the distal end of the inserter head. This procedure is shown and described above with respect to the description of FIGS. 33A-35B. FIG. 35B shows pusher rod 494 decoupling intervertebral disc 100 from the distal end of inserter head 474.

Figure 71:
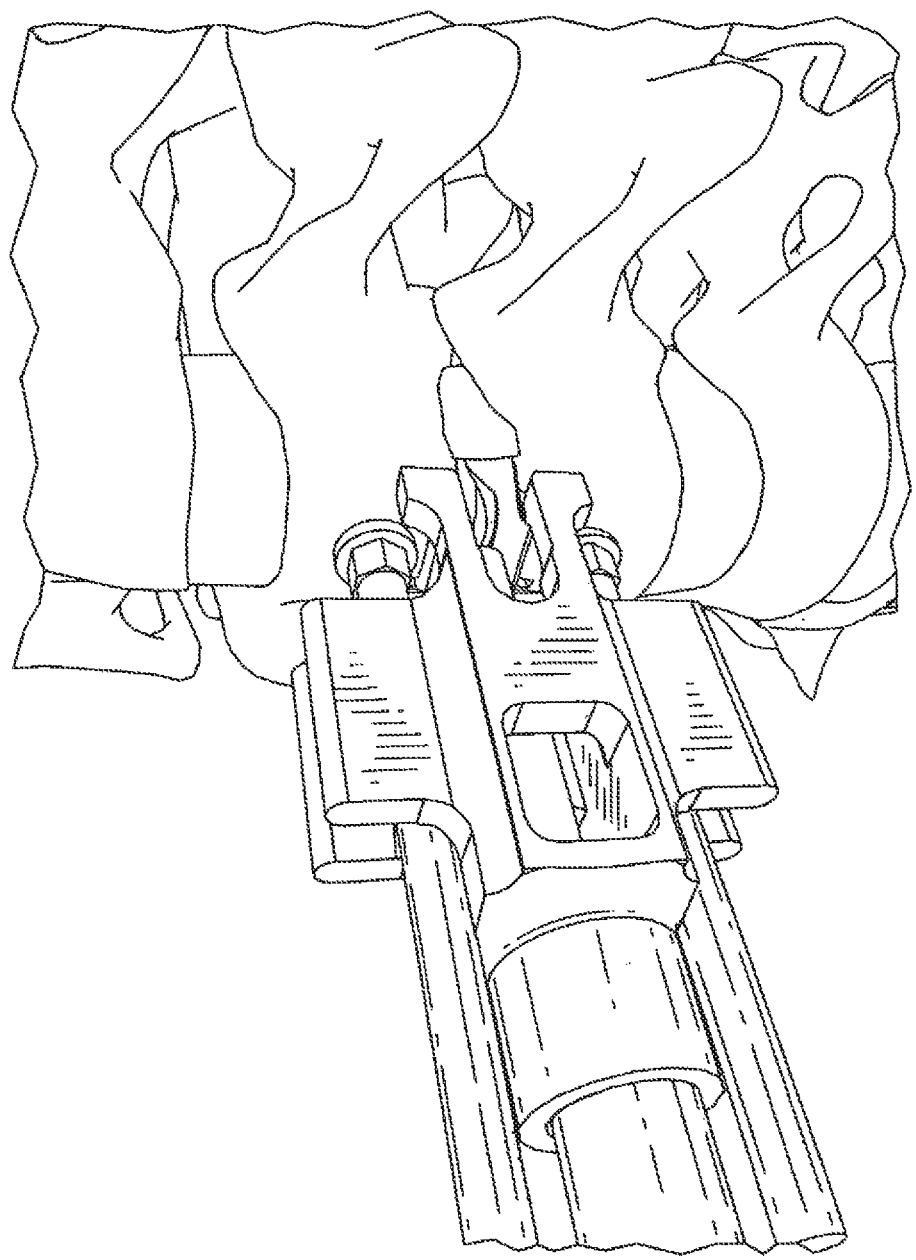

In certain preferred embodiments, the T-handle may be rotated approximately three or four turns for advancing the intervertebral disc implant 100 into the disc space. The proximal end of the handle for the inserter head may be impacted to ensure that the intervertebral disc implant continues into the disc space as the four arms of the inserter head remain in contact with the vertebral bodies. FIG. 71 shows further advancement of the intervertebral disc implant into the disc space. In certain preferred embodiments, immediately prior to insertion of the intervertebral disc implant, the disc space may be distracted approximately 2 mm wider than the base plates of the implant to facilitate insertion. The distraction may result from the grooves on the inserter head being angled relative to one another, as described above in certain preferred embodiments.

Figure 72:
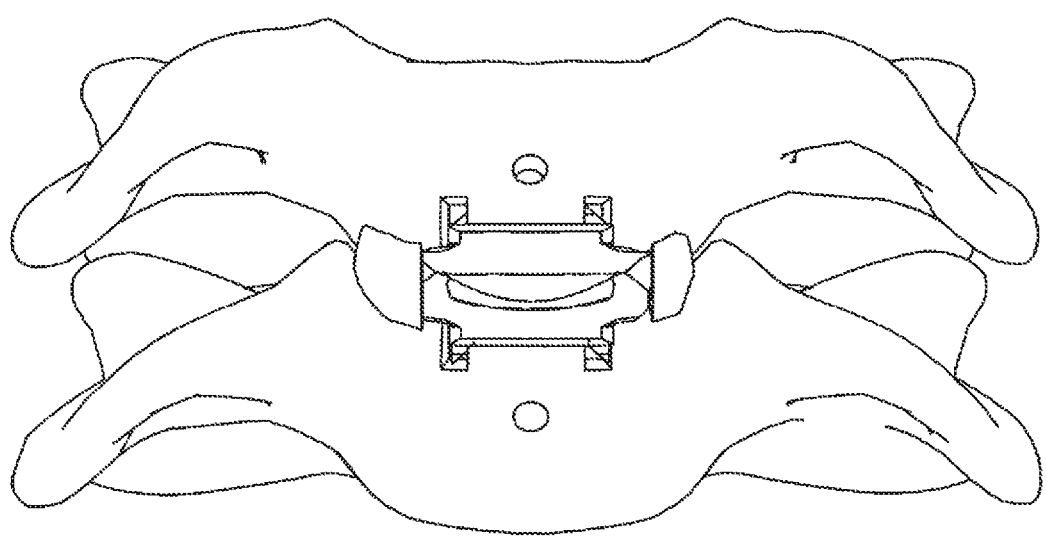
Figure 73:
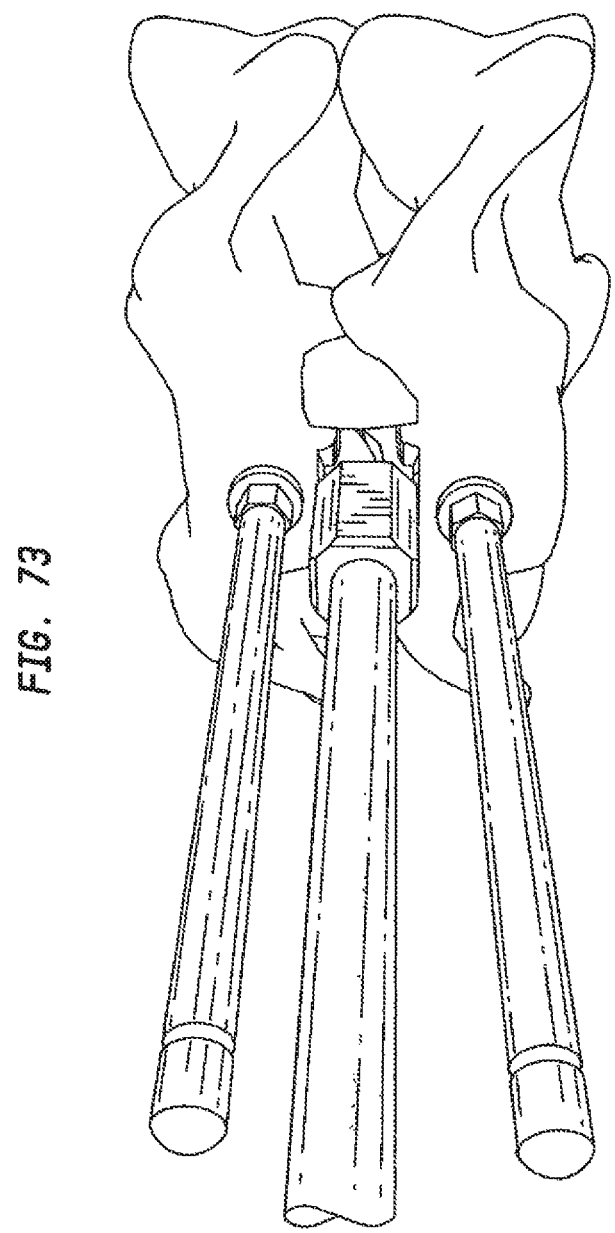

Referring to FIG. 72, insertion is completed when the implant is fully disengaged from the inserter head and the posterior faces of the anterior walls of the intervertebral disc's top and bottom elements are in contact with the anterior surfaces of the superior and inferior vertebral bodies. The anterior/posterior positioning of the implant and the baseplate size are preferably confirmed to be satisfactory using fluoroscopy. Referring to FIG. 73, if more posterior positioning of either the top element or the bottom element of the intervertebral disc implant is required, a tamp such as that shown and described above in FIG. 36A may be utilized for adjusting the position of the implant. In preferred embodiments, the tamp may be impacted to adjust the anterior/posterior depth of the top and bottom elements of the implant. The anterior walls of the top and bottom elements serve as vertebral body stops to prevent the implant from being impacted too far posteriorly. After final insertion and adjustments have been completed, the posterior faces of the anterior walls should be flush with the anterior faces of the respective vertebral bodies.

Referring to FIG. 72, once all relevant tests have been performed to ensure that the intervertebral disc is properly positioned within the disc space, the reference pins may be removed. A biocompatible material, such as a small amount of bone wax, may be applied to the reference pin openings remaining in the anterior surfaces of the superior and inferior vertebral bodies.

Figure 74:
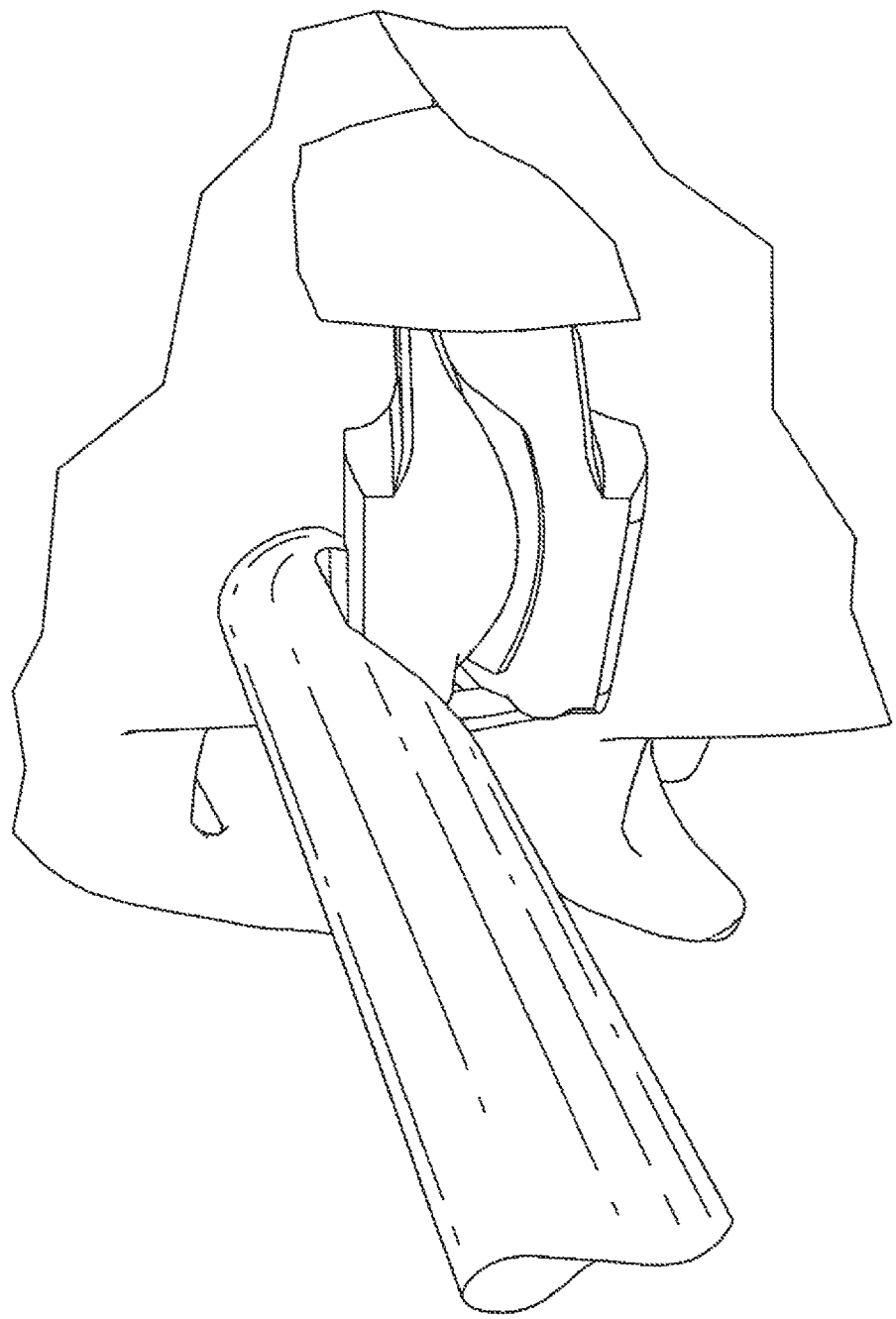
Figure 75A:
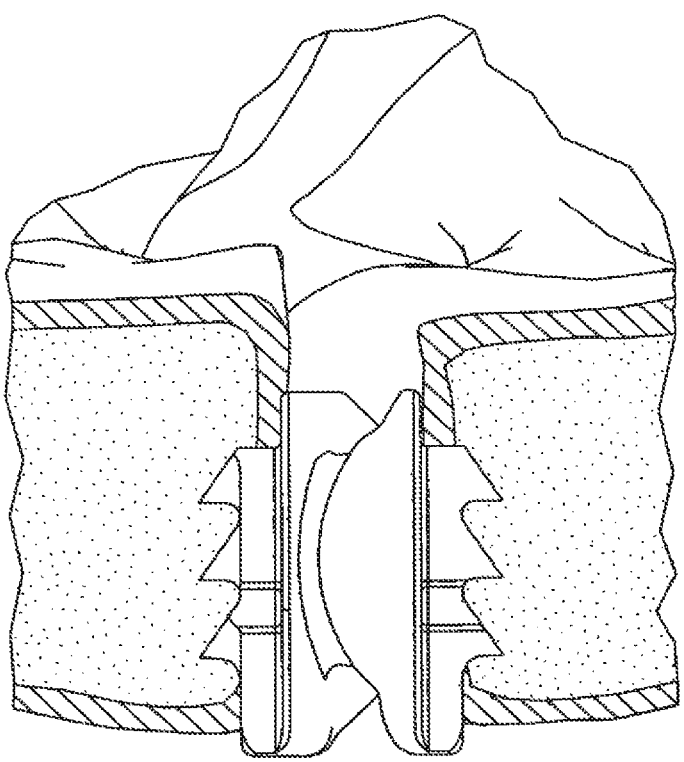
FIG. 75A shows a side view of the intervertebral disc implant shown in FIG. 72.
Figure 75B:
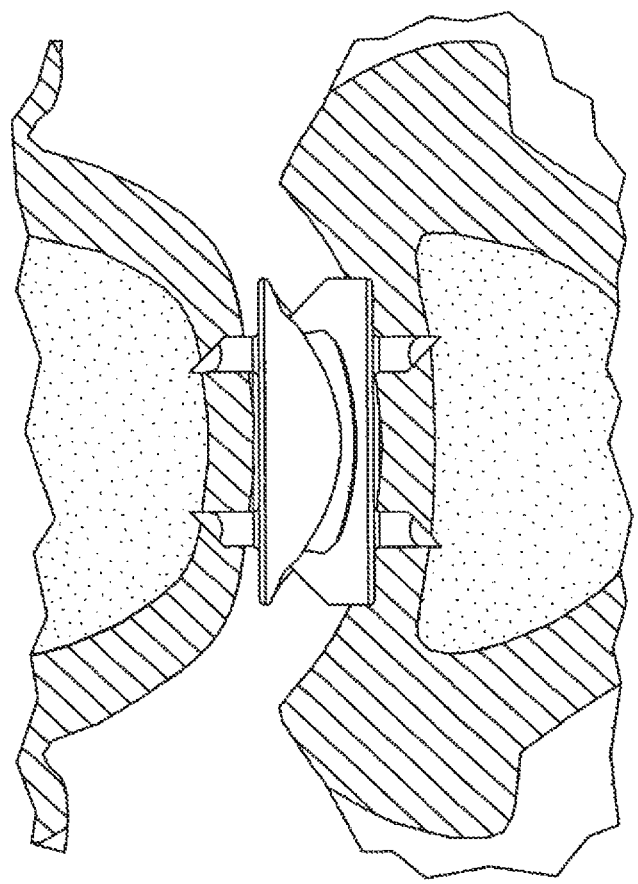
FIG. 75B shows an anterior end view of the intervertebral disc implant shown in FIG. 73.

Referring to FIGS. 75A and 75B, an intraoperative lateral and anterior/posterior image of the implant is preferably obtained to observe its final position. If the implant is not properly positioned, it may be removed such as by using the extractor shown and described above in FIGS. 37A-37D. In FIG. 74, a hook of the extractor is engaged with an anterior wall of a top element of the intervertebral disc implant. Once it has been confirmed that the intervertebral disc is properly positioned within the disc space, a standard surgical closure procedure for anterior spinal surgery may be performed. Prior to discharge from the hospital, a lateral and anterior/posterior X-ray with the patient in the standing and/or sitting position is preferred.

Following surgery, in certain preferred embodiments, a goal of post-operative rehabilitation is to return the patient to normal activity as soon as possible without jeopardizing soft and hard tissue healing. Preferably, the patient should wear a soft collar for approximately 1-2 weeks to support healing of the incision. The patient's rehabilitation program may be modified under the direction of a surgeon to take into consideration the patient's age, stage of healing, general health, physical condition, life-style, and activity goals. Adherence to a recommended rehabilitation program is highly desirable.

Figure 76A:
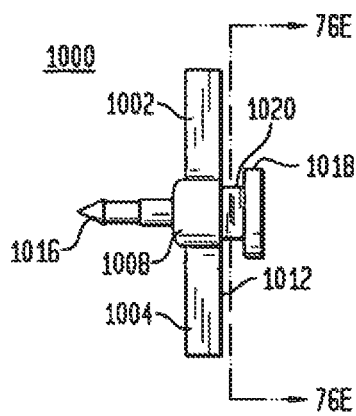
FIGS. 76A-76E show a midline marker, in accordance with certain preferred embodiments of the present invention.
Figure 76B:
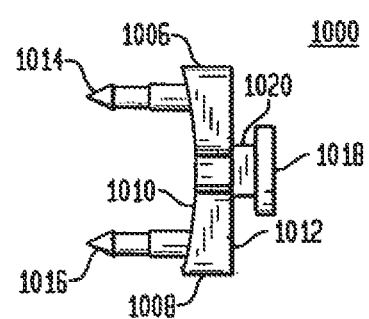
Figure 76C:
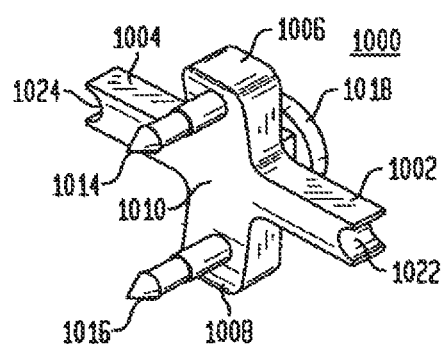
Figure 76D:
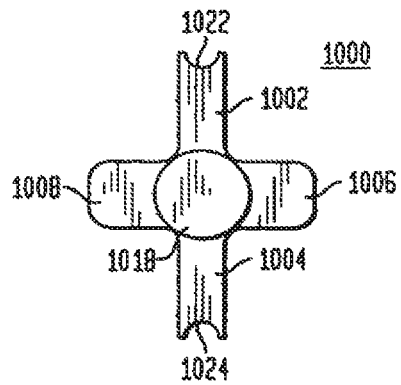
Figure 76E:
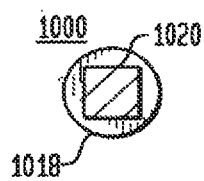

FIGS. 76A-76E show a midline marker 1000 that is used for determining a midline of a disc space between two vertebrae. The midline marker 1000 has a cruciform shape with a first vertical extension 1002, a second vertical extension 1004, a first lateral extension 1006, and a second lateral extension 1008. The midline marker has a leading face 1010 and a trailing face 1012. As shown in FIG. 76B, the leading face 1010 has a concave curved surface that extends between the first and second lateral arms 1006, 1008. The first lateral arm 1006 has a first barbed spike 1014 projecting therefrom, and the second lateral arm 1008 has a second barbed spike 1016 projecting therefrom. The midline marker 1000 includes a button 1018 projecting from the rear surface 1012 there, which is connected to the midline marker via connector segment 1020. As shown in FIG. 76E, the connector segment 1020 has a rectangular or square cross section, for reasons that will be described below.

Referring to FIG. 76D, the upper end of the first vertical extension 1002 has a concave recess 1022 and the lower end of the second vertical extension 1004 has a concave recess 1024. The concave recesses 1022, 1024 provide an alignment feature for marking vertebral bone and/or making openings in bone, as will be described in more detail below.

Figure 77A:
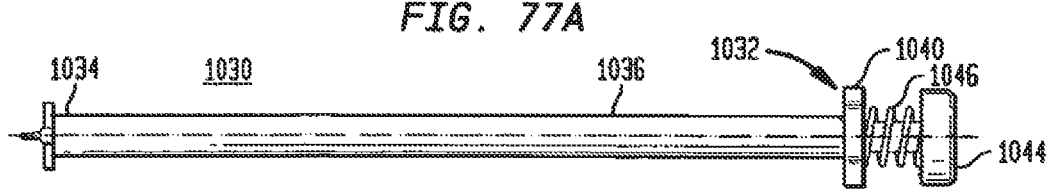
FIGS. 77A-77E show a midline marker handle for the midline marker shown in FIGS. 76A-76E, in accordance with certain preferred embodiments of the present invention.
Figure 77B:
Figure 77C:
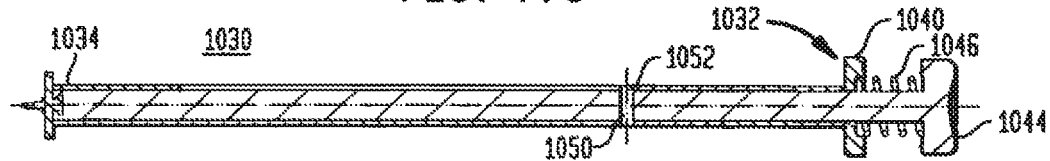
Figure 77D:
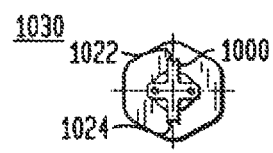
Figure 77E:
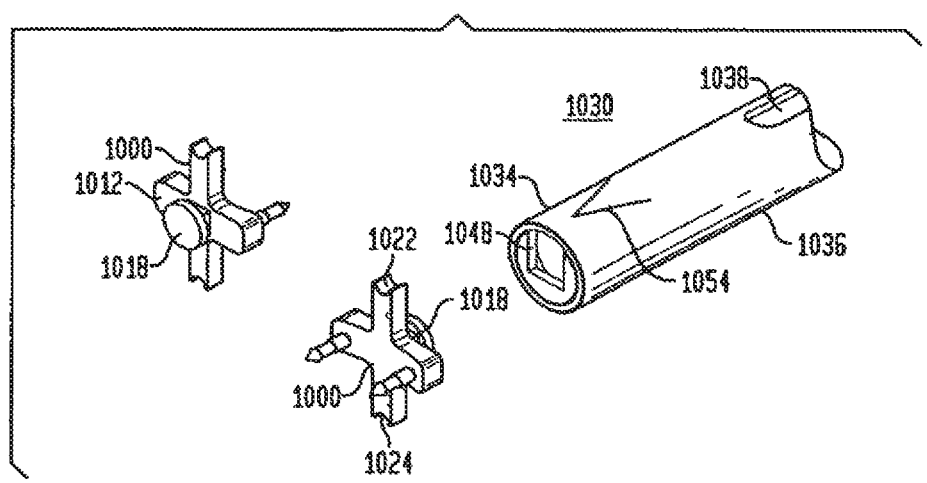

FIGS. 77A-77E show a midline marker handle 1030 for securing the midline marker 1000 shown in FIGS. 76A-76E. The midline marker handle 1030 includes a proximal end 1032 and a distal end 1034. The midline marker handle 1030 includes an outer shaft 1036 that extends between the proximal end 1032 and the distal end 1034. Referring to FIGS. 77B and 77E, the outer shaft 1036 has at least one slot 1038 formed therein. The slot 1038 serves as a guide slot, as will be described in more detail below. The proximal end 1032 of the outer shaft 1036 has a flange 1040 extending therefrom. The flange 1040 is preferably integrally formed with the outer shaft 1036. Referring to FIG. 77C, the midline marker handle includes a plunger 1042 that is disposed within the outer shaft 1036. The plunger 1042 has a knob 1044 secured to a proximal end thereof. The midline marker handle 1030 also includes a spring 1046 disposed between the flange 1040 and the knob 1044 for normally urging the plunger into a retracted position.

Referring to FIG. 77E, the distal end of the plunger 1042 includes a U-shaped opening 1048 that is adapted to receive the button 1018 projecting from the rear surface 1012 of the midline marker 1000 (FIG. 76B).

Referring to FIG. 77C, the plunger 1042 has an aperture 1050 extending therethrough and a pin 1052 is disposed within the apertures 1050. Referring to FIG. 77B, the pin 1052 moves with the plunger 1042, and is positioned within the slot 1038 provided in the outer shaft 1036 for guiding advancement of the plunger relative to the outer shaft 1036.

Referring to FIGS. 77B and 77E, the outer shaft 1036 includes an alignment feature 1054 that assists the surgeon in properly aligning the midline marker handle 1030 during a surgical procedure. Referring to FIGS. 77D and 77E, when the midline marker 1000 is secured to the midline marker handle 1030, the concave shaped recesses 1022, 1024 are preferably aligned with the alignment feature 1052.

Referring to FIGS. 77A-77C and 77E, the U-shaped opening 1048 at the proximal end of the plunger 1042 is normally urged into the retracted position by spring 1046. In order to overcome the force of the spring 1046 and advance the U-shaped opening 1048 so that it projects beyond the distal end of the outer shaft 1036, a surgeon will grasp the flange 1040 and urge the knob 1044 toward the distal end 1034 of the midline marker handle 1030. When the surgeon overcomes the force of the spring 1046, the plunger 1042 will move toward the distal end 1034 of the tool so as to project the U-shaped opening 1048 beyond the distal end of the outer shaft 1036.

Figure 78A:
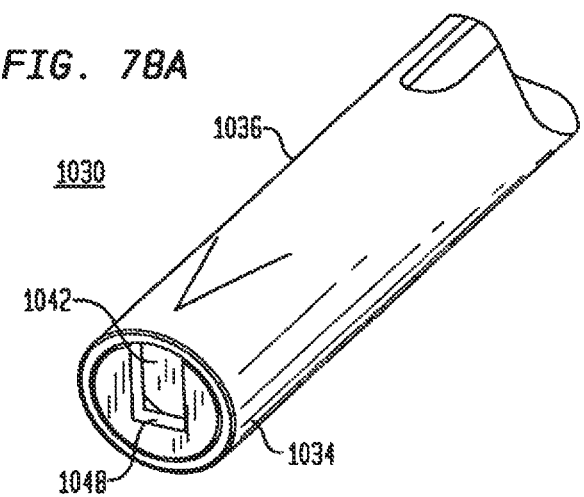
FIG. 78A shows the distal end of the midline marker handle shown in FIG. 77E.
Figure 78B:
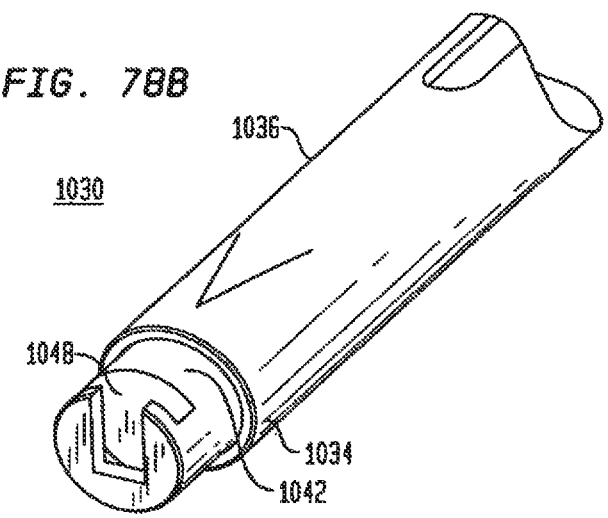
FIG. 78B shows an U-shaped capture element extendible from the distal end of the midline marker handle shown in FIG. 78A.

FIGS. 78A and 78B show advancement of the U-shaped opening 1048 beyond the distal end of the outer shaft 1036. In FIG. 78A, the plunger 1042 is in its normal retracted position so that the U-shaped opening 1048 lies within the distal end 1034 of the tool 1030. In FIG. 78B, the plunger 1042 is urged toward the distal end 1034 of the tool so that the U-shaped opening 1048 is moved beyond the distal end of the tool. At that point, the button 1018 (FIG. 76B) of the midline marker may be inserted into the U-shaped opening 1048. The plunger 1042 is then allowed to retract toward the proximal end of the tool so that the plunger moves back to the position shown in FIG. 78A. At that point, the button of the midline marker is captured in the U-shaped opening 1048 whereby the midline marker is coupled to the distal end of the midline marker handle 1030. FIGS. 77A-77C show the midline marker after it has been secured to the distal end 1034 of the midline marker handle 1030.

After the midline marker 1000 has been secured to the distal end of the midline marker handle 1030, the spikes 1014, 1016 (FIG. 76B) are preferably inserted into an intervertebral disc between opposing vertebrae.

FIGS. 79A-79D show a reference pin drill and insertion guide, in accordance with certain preferred embodiments of the present invention. The reference pin drill and insertion guide 1060 has a proximal end 1062, a distal end 1064, a handle 1066 at the proximal end 1062, a shaft 1068 that projects from a leading end of the handle 1066, and a head 1070 secured to a leading end the shaft 1068.

Figure 79A:
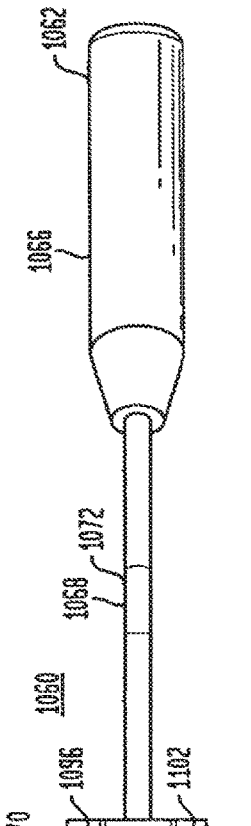
FIG. 79A-79D show a reference pin insertion guide, in accordance with certain preferred embodiments of the present invention.
Figure 79B:
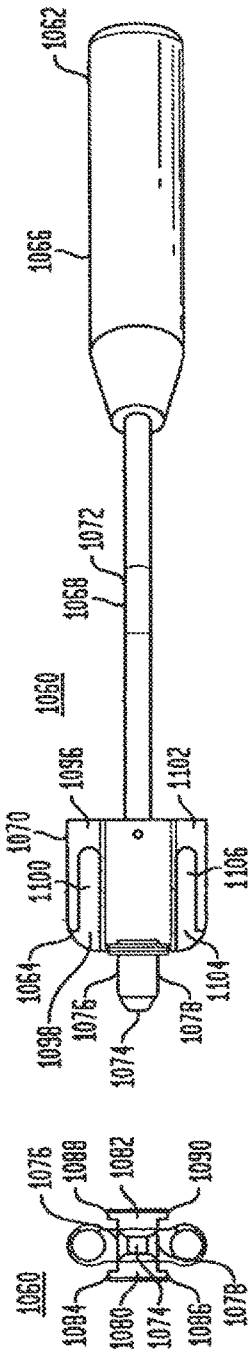

Referring to FIGS. 79A and 79B, the shaft 1068 preferably has an elbow 1072 forming an angle of approximately one hundred fifty (150) degrees. The elbow provides an angled shaft that enables the handle 1066 to be located out of alignment with the head 1070 for enhancing visibility of the head 1070 duping a surgical procedure.

Figure 79C:
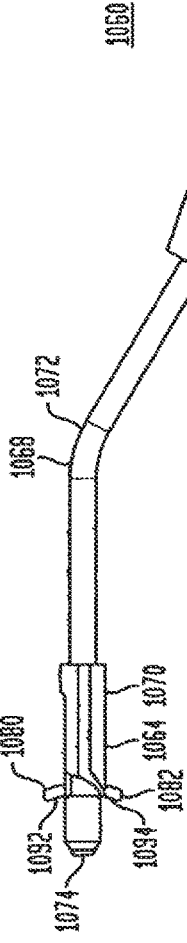
Figure 79D:
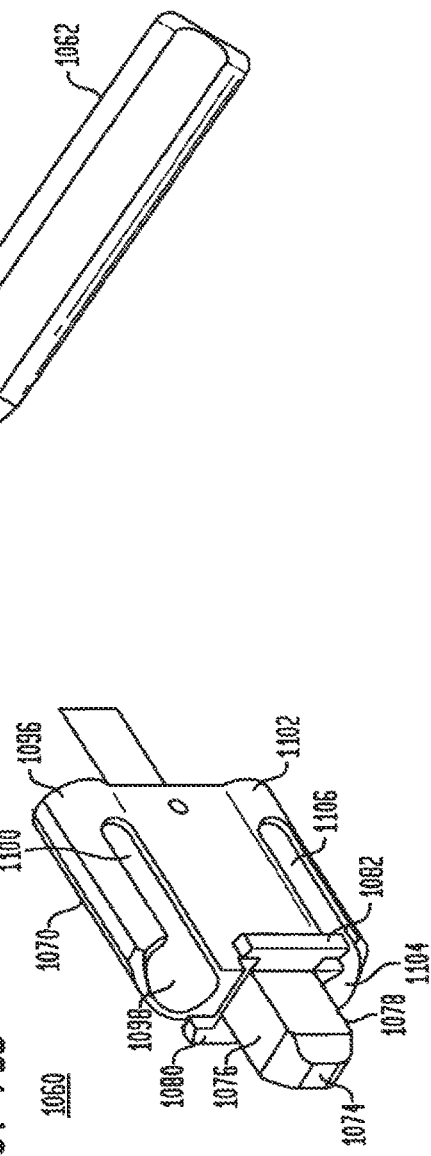

Referring to FIG. 79D, the head 1070 of the reference pin drill and insertion guide 1060 includes a tapered nose 1074 that is insertable into a disc space. The tapered nose 1074 includes a top surface 1076 adapted to engage an upper vertebral body and a bottom surface 1078 adapted to engage a lower vertebral body. The tapered nose 1074 is inserted into the disc space with the top surface 1076 engaging a first vertebral body and the bottom surface 1078 engaging a second vertebral body. The head 1070 includes a first vertebral body stop 1080 extending along one side of the head and a second vertebral body stop 1082 extending along an opposite side of the head 1070. The vertebral body stops are adapted to engage vertebral bone for preventing over-insertion of the guide 1060 into a disc spaces.

Referring to FIG. 79C, the first vertebral body stop 1080 has an upper end 1084 that extends above the top surface 1076 of the tapered nose 1074 and a lower end 1086 that extends below the bottom surface 1078 of the tapered nose 1074. Similarly, the second vertebral body stop 1082 has an upper end 1088 that extends above the top surface 1076 of the tapered nose 1074 and a lower end 1090 that extends below the bottom surface 1078 of the tapered nose 1074. The upper ends 1084, 1088 of the respective vertebral body contacts 1080, 1082 extend approximately two (2) millimeters above the top surface 1076 of the tapered nose 1074. The lower ends 1086, 1090 of the respective vertebral body stops 1080, 1082 extend approximately two (2) millimeters below the bottom surface 1078 of the tapered nose 1074. In the preferred embodiment, the vertebral body stops preferably have a height of approximately two (2) millimeters. The enhanced size of the vertebral body stops improves the stability of the reference pin drill and insertion guide when drilling holes in the vertebral bone and inserting reference pins.

Referring to FIG. 79B, the leading faces 1092, 1094 of the vertebral body stops 1080 1082 have concave curved surfaces that generally conform to the outer surfaces of the vertebrae. The concave curved surfaces also enhance stability of the guide 1060 as described above.

Referring to FIGS. 79A and 79D, the head 1070 includes a first protective sheath 1096 including a central opening 1098 and a slot 1100. The first protective sheath 1096 is disposed over the top surface 1076 of the tapered nose 1074. The head 1070 also includes a second protective sheath 1102 having a central 1104 extending therethrough and a slot 1106.

Referring to FIG. 79D, the first and second protective sheaths 1096, 1102 enable reference pin holes to be safely and effectively drilled in vertebral bone. The sheaths 1096, 1102 protect the surrounding tissue as drill bits reference pins and/or driving instruments are inserted through the sheaths. The openings 1098, 1104 extending through the respective sheaths 1096, 1102 are adapted to receive drill bits, sleeves, and reference pin drivers that enable reference pins to be inserted into openings formed in the vertebrae. Although the present invention is not limited by any particular theory of operation, it is believed that the slots 1100, 1106 provided on the sheaths enable a surgeon to visibly observe advancement of drill bits, reference pin drivers, sleeves, and/or any tools used to formed the openings in the vertebral bone or insert the reference pins in the openings.

Figure 80A:
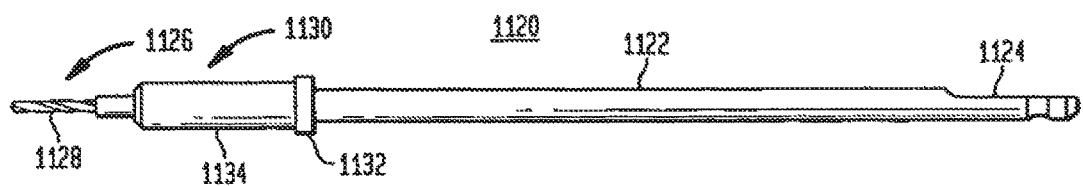
FIGS. 80A-80B show a step drill for use with the reference pin insertion guide shown in FIGS. 79A-79D.
Figure 80B:
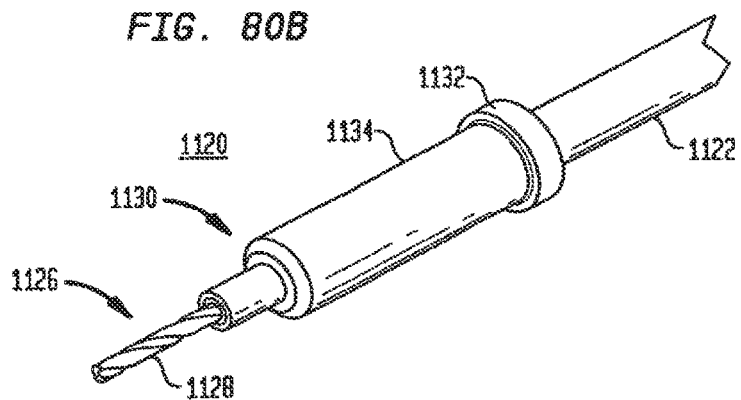

FIGS. 80A and 80B show a step drill for use with the reference pin drill and insertion guide 1060 shown in FIGS. 79A-79B. The step drill 1120 includes a shaft 1122 having a proximal end 1124 and a distal end 1126. The proximal end 1124 is adapted to be coupled with an instrument that rotates the shaft 1122. The proximal end of the step drill includes a drill bit 1128 and a step structure 1130 that extends between the drill bit 1128 and a stop flange 1132. The step drill 1120 includes a cylindrical surface 1134 having an outer diameter that substantially matches the inner diameter of the openings 1098, 1104 of the protective sheaths 1096, 1102 (FIG. 79D).

Figure 81:
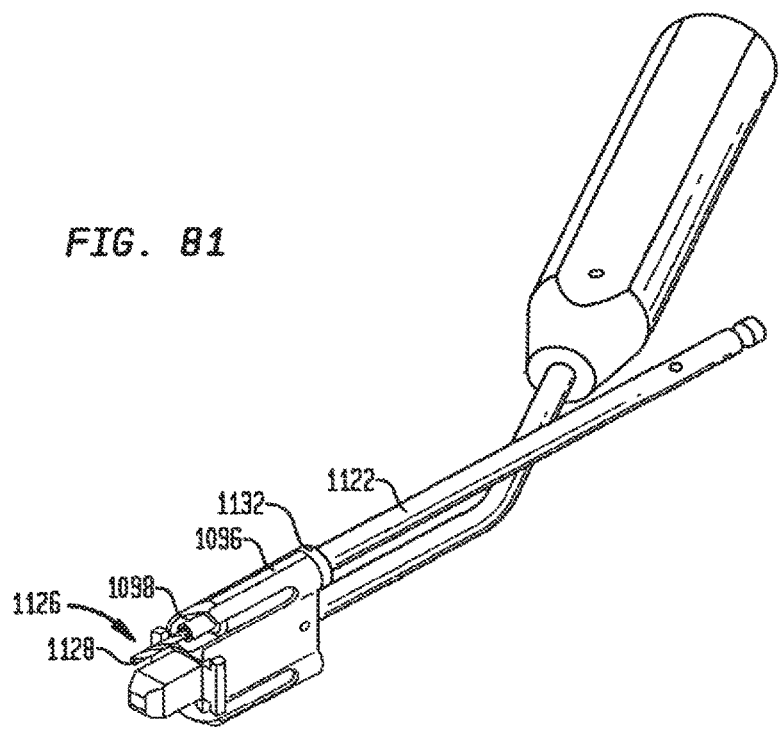
FIG. 81 shows the step drill of FIGS. 80A-80B coupled with the reference pin insertion guide of FIGS. 79A-79D.

Referring to FIG. 81, after the distal end 1126 of the step drill 1122 is inserted into the opening 1098 of the protective sheath 1096, the step drill may be advanced until the stop flange 1132 abuts against the sheath 1096. As the step drill is rotated, the drill bit 1128 forms an opening in the vertebral body for receiving a reference pin.

Figure 82:
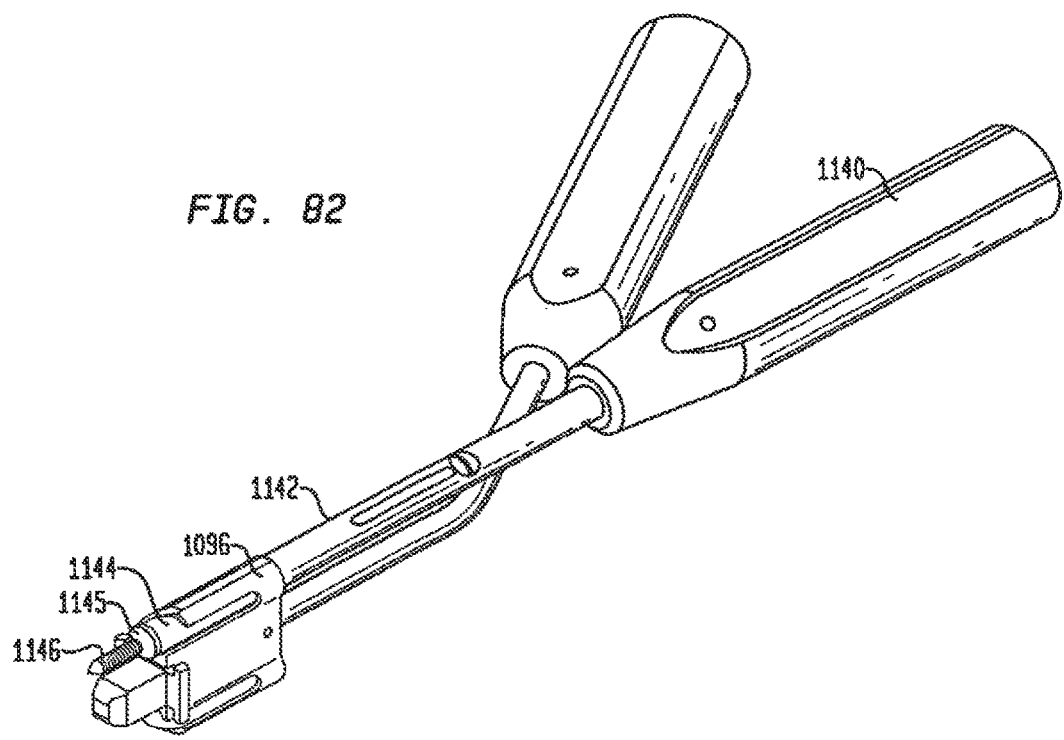
FIG. 82 shows the reference pin insertion guide of FIGS. 79A-79D coupled with a reference pin and a driver for advancing the reference pin.

FIG. 82 shows a driver 1140 having a shaft 1142 extending from a forward end of a handle. The shaft 1142 has an opening at a distal end 1144 thereof. The opening at the distal end 1144 receives a reference pin 1145 having threads 1146. The shaft 1142 of the driver 1140 is insertible into the opening of the protective sheath 1096 for anchoring the reference pin 1145 in vertebral bone. The handle of the driver 1140 is rotated for threading the reference pin 1145 into the opening in the vertebral body.

FIG. 83 shows a step drill 1220 in accordance with another preferred embodiment of the present invention. The step drill 1220 includes a shaft 1222 having a proximal end 1224 and a distal end 1226. The step drill includes a drill bit 1228 at the distal end 1226, a first section 1230 having a first diameter that is larger than the diameter of the drill bit section 1228, and a second section 1232 having a second diameter that is larger than the first diameter of the first section 1230.

Referring to FIGS. 84A and 84B, a reference pin drill guide 1260 used for forming openings in vertebral bone has a proximal end 1262 and a distal end 1264. The reference pin drill guide includes a handle 1266, a shaft 1268 and a head 1270. The shaft includes an elbow 1272 that provides an angle in the shaft of approximately one hundred fifty (150) degrees. The head 1270 includes a tapered nose 1274 insertible into a disc space. The plug includes a top surface 1276 and a bottom surface 1278, which are adapted to be inserted between opposing faces of vertebrae.

The head 1270 includes a first vertebral body stop 1280 projecting from one side of the head 1270 and a second vertebral body stop 1282 projecting from an opposite side of the head. The first vertebral body stop 1280 includes an upper end 1284 that projects above the top surface 1276 of the tapered nose 1274 and a lower end 1286 that projects below the bottom surface 1278 of the tapered nose 1274. The second vertebral body stop 1282 includes an upper end 1288 that projects above the top surface 1276 of the tapered nose 1274 and a lower end 1290 that projects below the bottom surface 1278 of the tapered nose 1274. Referring to FIG. 84A, the leading faces 1292, 1294 of the respective first and second vertebral body stops 1280, 1282 have a concave curve for conforming to the outer surfaces of the vertebral bone. The upper ends 1284, 1288 of the respective vertebral body contacts 1280, 1282 extend approximately two (2) millimeters above the top surface 1276 of the tapered nose 1274. The lower ends 1286, 1290 of the respective vertebral body stops 1280, 1282 extend approximately two (2) millimeters below the bottom surface 1278 of the tapered nose 1274. In the preferred embodiment, the vertebral body stops preferably have a height of approximately two (2) millimeters.

Referring to FIGS. 85A and 85B, the head 1270 of the reference pin drill guide 1260 includes a first protective sheath 1296 having an opening extending therethrough and a slot 1300 formed in the side of the first protective sheath. The head 1270 includes a second protective sheath 1302 having an opening extending therethrough and a slot 1306 formed in the side of the second protective sheath. The openings in the respective first and second protective sheaths 1296, 1302 are designed to receive the step drill 1220 shown in FIG. 83.

FIGS. 85A and 85B show the step drill 1220 inserted into the opening extending through the first protective sheath 1296. The step drill 1220 may be advanced until the shoulder between the first step section 1230 and the second step section 1232 (FIG. 83) engages the trailing end of the first protective sheath 1296. The step drill 1220 may be rotated so that the drill bit 1228 forms an opening in vertebral bone.

FIGS. 86A and 86B show the formation of openings in vertebral bone for reference pins, in accordance with certain preferred embodiments of the present invention. Referring FIG. 86A, the tapered nose 1274 of the reference pin drill guide 1260 shown in FIG. 85A is inserted into a disc space between opposing vertebrae. The tapered nose 1274 is advanceable into the disc space until the vertebral body stop 1282 abuts against vertebral bone. Once the vertebral body stop abuts against the vertebral bone, the head 1270 cannot be further advanced into the disc space. The step drill 1220 is then inserted into the opening of the first protective sheath 1296, and advanced into vertebral bone to form reference pin openings in the vertebral bone. The slot 1300 in the protective sheath 1296 enables the surgeon to visibly monitor the advancement of the drill bit 1228 into the vertebral bone. The slot 1300 may also be used to monitor the advancement of a reference pin into the bone.

FIGS. 87A-87D show a fin drill guide 1314 that is generally similar to the drill guide shown above in FIGS. 20A-20D described above. The fin drill guide 1314 shown in FIGS. 87A-87D includes vertebral body stops 1380, 1382 that extend laterally from opposite sides of head 1370. Referring to FIGS. 87C and 87D, the first vertebral body stop 1380 includes an upper end 1384 that extends above a top surface 1376 of tapered nose 1374 and a lower end 1386 that extends below the bottom surface 1378 of tapered nose 1374. The second vertebral body stop 1382 includes an upper end 1388 that extends above the top surface 1376 and a lower end 1390 that extends below the bottom surface 1378. In the preferred embodiment, the vertebral body stops have a height of approximately two (2) millimeters. Referring to FIG. 87B, the leading faces 1392, 1394 of the respective first and second vertebral body stops 1380, 1382 have concave surfaces that generally conform to the outer surfaces of vertebral bodies. The upper ends 1384, 1388 of the respective vertebral body contacts 1380, 1382 extend approximately two (2) millimeters above the top surface 1376 of the tapered nose 1374. The lower ends 1386, 1390 of the respective vertebral body stops 1380, 1382 extend approximately two (2) millimeters below the bottom surface 1378 of the tapered nose 1374.

During a surgical procedure for preparing a disc space for receiving an implant, the tapered nose 1374 is inserted into a disc space until the first and second vertebral body stops 1380, 1382 abut against the outer surfaces of vertebral bodies. The engagement of the first and second vertebral body stops 1380, 1382 with the vertebral bone prevents further advancement of the tool. A drill 1322 may then be advanced through the openings in the head 1370 for preparing the disc space, as described above.

FIGS. 88A-88D show a chisel guide 1450 that is similar to the chisel guide shown and described above in FIGS. 21A-21D. The chisel guide 1450 includes a head 1466 that is insertible into a disc space, a first vertebral body stop 1480 provided on a first lateral side of the head 1466 and a second vertebral body stop 1482 provided on a second lateral side of the head 1466. The first vertebral body stop 1480 has an upper end 1484 that extends above a top surface of the head 1466 and a lower end 1486 that extends below a bottom surface of the head 1466. The second vertebral body stop 1482 includes an upper end 1488 that extends above the top surface of the head 1466 and a lower end 1490 that extends below the bottom surface of the plug 1466. The respective upper ends 1484, 1488 of the vertebral body stops 1480, 1482 extend approximately two (2) millimeters over the top surface of the head 1466, and the respective lower ends 1486, 1490 of the first and second vertebral body stops 1480, 1482 extend approximately two (2) millimeters below the bottom surface of the head 1466. The vertebral body stops preferably abut against the outer surfaces of the opposing vertebrae for providing lateral stability for the chisel guide. As a result, the chisel guide will generally remain stable, in place and will not move relative to the vertebral bodies during a bone chiseling step.

Referring to FIG. 88A, the chisel guide 1450 also includes a handle 1494 provided at a proximal end thereof and a depression 1496 formed in the handle 1494. As will be described in more detail below, the depression 1496 provides additional room for advancement of a chisel toward the distal end of the chisel guide 1450.

FIG. 89 shows the head 1466 at the distal end of the chisel guide 1450 after being inserted into a disc space. Reference pin 1464 (anchored in a vertebral body) guides advancement of the chisel guide toward the disc space. The distal end of the chisel guide is advanced into the disc space until the first and second vertebral body stops 1480, 1482 abut against the outer surfaces of the vertebral bodies. A chisel 1474, similar to that described above in FIGS. 22A-22D, is coupled with the chisel guide. The chisel 1474 is advanced into bone by striking the knob 1475 at the distal end thereof. The depression 1496 provided at the proximal end of the handle 1494 enables further advancement of the chisel 1474 toward the disc space. The depth of the cut ultimately made is limited by the chisel impaction head contacting the handle of the chisel guide.

FIGS. 90A-90D show a sizer 1508 that is generally similar to the sizer shown above in FIGS. 25A-25D. The sizer 1508 includes a main body 1510 having a distal end 1512, a top surface 1514, and a bottom surface 1516. The main body includes beveled surfaces 1518, 1519 extending between the distal end 1512 and the top and bottom surfaces 1514, 1516 to ease insertion of the sizer between opposing vertebrae. The sizer 1508 includes an adapter shaft 1520 and first and second projections 1522A, 1522B provided on the adapter shaft 1520.

The sizer 1508 also includes vertebral body stop 1524 and 1526 for limiting insertion of the sizer into a disc space. The first vertebral body stop 1524 includes a depression or cutout 1525 that provides clearance for reference pins 264 or other tools. The second vertebral body stop 1526 also includes a depression or cutout 1527 for providing clearance for a reference pin 264. The upper and lower beveled surfaces 1518, 1519 extend approximately one (1) millimeter from the distal end 1512. The beveled surfaces 1518, 1519 form an angle of approximately twenty seven (27) degrees.

FIGS. 91A-91C show a handle 1532 that is generally similar to that shown and described above in FIGS. 26C-26D. The sizer of FIGS. 90A-90D is secured to the distal end of the handle 1532. FIGS. 92A and 92B show the distal end of the handle 1532 with the sizer 1508 coupled to the handle. The sizer 1508 may be attached to the handle 1532 by sliding the projections 1522A, 1522B into the grooves extending from the distal end 1530 of the handle 1532. Referring to FIG. 91C, after the sizer 1508 is coupled with the handle 1532, a rotatable element 1534 may be rotated for locking the sizer 1508 to the handle 1532.

Referring to FIGS. 93A-93D, in certain preferred embodiments of the present invention, a trial or serrated broach 1636 includes a proximal end 1638, a distal end 1640, a shaft 1642 extending between the distal and proximal ends, and a striking surface 1644 located at the proximal end 1638 thereof. The serrated broach also includes a head 1646 secured to the distal end 1638. The head 1646 includes protrusions 1648 having teeth 1650 that are positioned to coincide with the protrusions of an intervertebral implant in order to ensure proper orientation. The size of the serrated broach 1636 that is selected for use is based upon the largest sizer that safely fit within the intervertebral disc space. The serrated broach 1636 also includes reference pin alignment openings 1652 and 1654, which are adapted to slide over reference pins secured to vertebral bone.

The serrated broach 1636 includes a first vertebral body stop 1680 and a second vertebral body stop 1682 projecting from opposite sides of the head 1646. The first vertebral body stop 1680 includes an upper end 1688 that projects above a top surface of the head 1646 and a lower end 1690 that projects below a bottom surface of the head 1646. The second vertebral body stop 1682 includes an upper end 1688 that projects above a top surface of the head 1646 and a lower end 1690 that projects below a bottom surface of the head 1646. The upper ends of the vertebral body stops 1680, 1682 project approximately two (2) millimeters over the top surface of the head 1646. The lower ends 1686, 1690 extends approximately two (2) millimeters below the bottom surface of the head 1646. The vertebral body stops 1680, 1682 preferably have a height of about two (2) millimeters.

Referring to FIGS. 94A-94F, in accordance with certain preferred embodiments of the present invention, an implant dispenser 1756 is adapted to hold the top and bottom elements of an intervertebral disc implant 100 as a single unit with the articulating surfaces held together. Referring to FIGS. 94A-94C, the implant dispenser 1756 is preferably flexible and includes a superior arm 1758 for engaging a top element of an intervertebral disc implant and an inferior arm 1764 for engaging a bottom element of an intervertebral disc implant. The superior and inferior arms preferably have lateral notches 1762 formed therein for receiving the teeth of the top and bottom elements. The implant dispenser preferably includes a central support 1764 that enables the superior and inferior arms 1758, 1760 to flex relative to one another and to move away from one another for releasing an intervertebral disc implant.

Referring to FIGS. 94A, 94B, 94D and 94E, the superior arm 1758 includes a slot 1775 formed therein. Referring to FIG. 94C, the inner surface of the superior arm 1758 has a first notch 1777 formed therein and the interior surface of the inferior arm 1760 has a second notch 1779 formed therein.

Figure 95A:
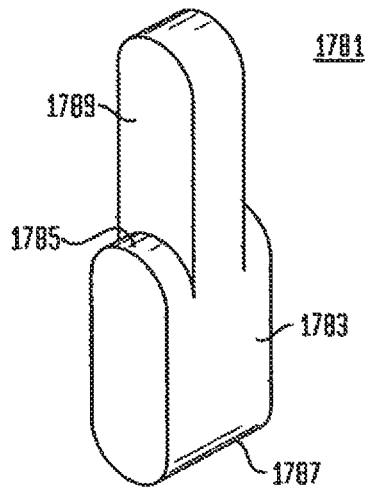
FIGS. 95A-95C show a clip used with the implant dispenser shown in FIGS. 94A-94F.
Figure 95B:
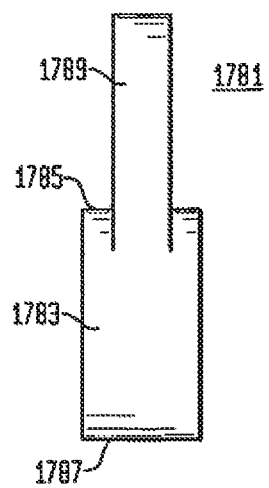
Figure 95C:
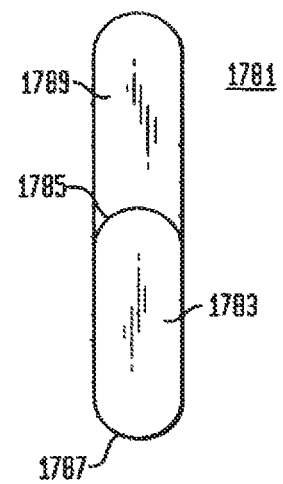

FIGS. 95A-95C show a clip 1781 that is insertible between the superior and inferior arms of the implant dispenser shown in FIGS. 94A-94F. The clip 1781 includes a main body 1783 having an upper end 1785 and a lower end 1787. The upper and lower ends 1785, 1787 of the main body 1783 preferably conform to the notches 1777, 1779 formed in the inner surfaces of the superior and inferior arms 1758, 1760 of the implant dispenser 1756. The clip 1781 includes a projection 1789 that extends upwardly from the main body 1783. The projection 1789 is adapted to fit within the slot 1775 formed in the superior arm 1758 of the implant dispenser 1756 so as to prevent the superior and inferior arms from being moved toward one another.

Figure 96A:
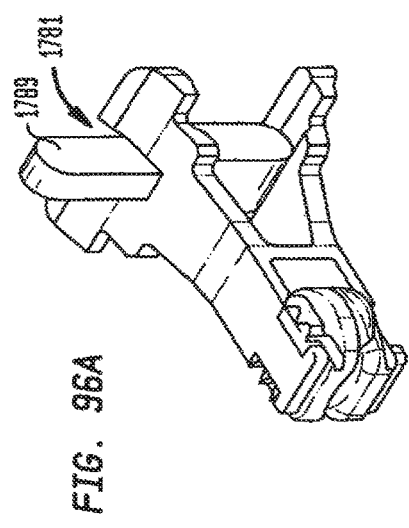
FIGS. 96A-96E show an intervertebral disc secured by the implant dispenser of FIGS. 94A-94E, whereby the implant dispenser is coupled with the clip of FIGS. 95A-95C.
Figure 96B:
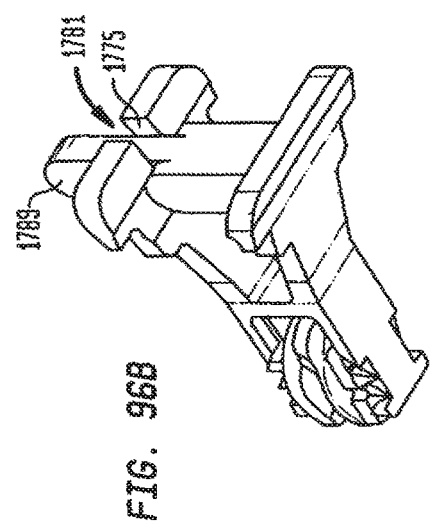
Figure 96D:
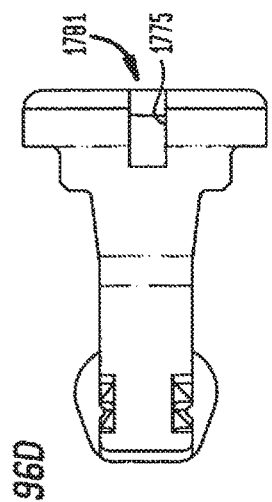
Figure 96C:
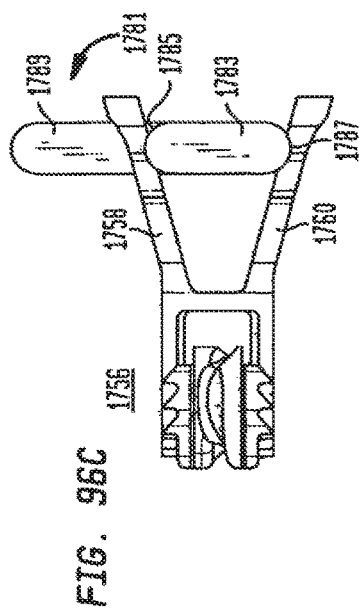
Figure 96E:
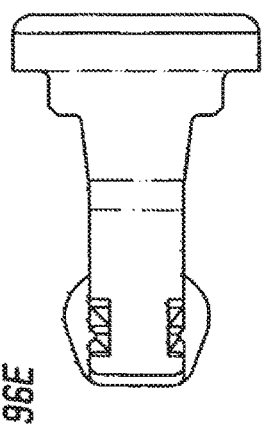

FIGS. 96A-96E show the clip 1781 disposed between the superior arm 1758 and the inferior arm 1760 of the implant dispenser 1756, whereby the main body 1783 of the clip 1781 is positioned between the superior and inferior arms 1758, 1760. The upper end 1785 of the main body 1783 preferably engages the notch formed in the inner surface of the superior arm 1758, and the lower end 1787 of the main body 1783 is preferably engaged with the notch formed in the inner surface of the inferior arm 1760. Referring to FIGS. 96A-96C, the projection 1789 preferably extends through the slot 1775 formed in the superior arm 1758. When in place between the arms 1758, 1760, the clip 1781 prevents the superior and inferior arms 1758, 1760 from moving toward one another. The clip 1781 is preferably in place between the arms during transport and storage of the implant/implant dispenser assembly. As a result, when the clip is in place, the superior and inferior arm 1758, 1760 cannot be moved towards one another so as to accidentally dispense or dislodge the implant.

FIGS. 97A-97F and 98A-98B show an implant insertion tool 1800 for inserting an intervertebral disc implant, such as the implant shown above in FIGS. 1-6B. Referring to FIGS. 97A-97C, the implant insertion tool 1800 includes an inserter body 1802 having a proximal end 1804 and a distal end 1806. The implant insertion tool 1800, which is preferably made of a biocompatible material such as titanium, includes an inserter head 1876 that is integrally connected with the inserter body 1802. The distal end 1878 of the inserter head 1876 includes four spaced arms 1882 having inwardly facing surfaces with projections 1884 that are adapted to fit within the depressions formed within the protrusions of the top and bottom elements of the intervertebral disc implant. Referring to FIG. 97D, the inserter head 1876 includes a central opening 1886 extending therethrough. Referring to FIGS. 97A and 97D, the inserter head 1876 includes an upper alignment groove 1888 and a lower alignment groove 1890. The alignment grooves 1888, 1890 are adapted to engage the reference pins for guiding advancement of the inserter head. In certain preferred embodiments, the alignment grooves 1888, 1890 taper toward one another so that the grooves are closer to one another at distal ends thereof and farther away from one another at proximal ends thereof. The taper of the grooves 1888, 1890 will cause the anchored reference pins to move away from one another as the insertion tool is moved toward the disc space thereby providing distraction in order to aid in implant insertion.

FIG. 97E shows the projection 1884 on one of the four arms 1882. As noted above, the projections 1884 on the arms 1882 engage the depressions (e.g. reference number 121 in FIG. 2C) in the protrusions of the top and bottom elements of the intervertebral discs.

FIGS. 98A and 98B show vertebral body stops 1892 provided at the distal ends of the arms 1882. The vertebral body stops 1892 are designed to abut against vertebral bone to prevent over-insertion of an intervertebral implant into a disc space.

FIGS. 99A and 99B show the implant dispenser 1756 of FIG. 96C holding an intervertebral disc implant 1000, and transferring the implant 1900 to the arms 1882 of the implant insertion tool 1800. Referring to FIG. 99B, the depressions formed in the protrusions of the implant are coupled with the projections on the arms 1882 of the inserter head 1874. The insertion tool 1800 is coupled to an insertion tool handle 1893 having a plunger rod 1894 extending therethrough. The distal end of the plunger rod 1894 includes a knob 1895 having a contact surface 1896 that may be engaged for advancing the plunger rod 1894 toward the distal end of the tool. Referring to FIGS. 100A and 100B, after the implant 1900 has been secured to the arms 1882 of the inserter head 1876, the implant dispenser may be removed. Referring to FIG. 100B, at this point, the implant 1000 is held by the arms 1882 of the inserter head. Referring to FIGS. 101A-101B, the pusher rod 1894 may be advanced toward the distal end of the inserter head 1874 for decoupling the implant 1000 from the arms 1882 of the inserter head 1874. Central slot 1806' (shown in FIG. 97B) preferably allows the arms to flex laterally, thereby allowing insertion and release of the implant.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An implant dispenser for holding the top and bottom elements of an intervertebral disc implant, the dispenser comprising:
 a superior arm for contacting the top element of the intervertebral disc implant and having a first notch;
 an inferior arm for engaging the bottom element of the intervertebral disc implant and having a second notch;
 a central support connecting the superior and inferior arms, the central support allowing for the superior and inferior arms to move relative to one another; and
 a clip disposed between the superior and inferior arms to prevent the superior and inferior arms from moving towards one another, wherein the clip includes a main body having an upper end and a lower end, the upper end disposed within the first notch and the lower end disposed within the second notch.

2. The implant dispenser of claim 1, wherein superior and inferior arms include lateral notches for receiving teeth of the top and bottom element of the intervertebral disc implant.

3. The implant dispenser of claim 1, wherein the superior arm includes a slot and the clip includes a projection extending from the main body, the projection being disposed within the slot of the superior arm.

4. An implant dispenser for holding an intervertebral disc implant, the dispenser comprising:
 first and second arms;
 a central support connecting the first and second arms so that ends of the first and second arms are biased toward a first position in which the first and second arms are adapted to hold the intervertebral disc implant therebetween, the central support defining a pivot about which the first and second arms are configured to pivot between the first position and a second position, wherein in the second position, the bias of the first and second arms is overcome to release the intervertebral implant held by the arms in the first position; and
 a clip removably engaged to the first and second arms so as to prohibit movement of the first and second arms between the first and second positions,
 wherein when the clip engages first ends of the first and second arms, the intervertebral disc implant is held between second ends of the first and second arms, and the central support is disposed between the first and second ends of the first and second arms.

5. The implant dispenser of claim 4, wherein the clip is disposed between the first and second arms.

6. The implant dispenser of claim 4, wherein the first arm includes a slot and the clip includes a main body and a projection extending from the main body, the projection being received by the slot of the first arm, and the main body being disposed between the first and second arms when the clip is engaged thereto.

7. The implant dispenser of claim 4, wherein the first and second arms each include lateral notches configured to receive opposing rows of bone engaging features of the intervertebral disc implant.

8. An implant dispenser for holding first and second elements of an intervertebral disc implant, the dispenser comprising:
- a first arm;
- a second arm, the first and second arms movable with respect to each other between first and second positions;
- a locking mechanism for maintaining the first and second arms in the first position, wherein in the first position, the first and second arms are positioned such that the first and second elements are secured by the first and second arms when the first and second elements are engaged by the dispenser and, in the second position, the first and second arms are positioned such that the first and second elements can be removed from the dispenser
- wherein the locking mechanism is a clip inserted between the first and second arms to prevent the first and second arms from moving towards each other.

9. The implant dispenser of claim 8, wherein the first and second arms are pivotally attached.

10. The implant dispenser of claim 8, further comprising a central support connecting the first and second arms, the central support allowing for the first and second arms to move relative to one another.

11. The implant dispenser of claim 10, wherein the central support is disposed between first and second ends of the first and second arms so that moving the first ends of the first and second arms towards each other pivots the first and second arms about the central support so that the second ends of the first and second arms move farther from each other.

12. The implant dispenser of claim 8, wherein, in the first position, the first and second elements are held between ends of the first and second arms when the first and second elements are engaged by the dispenser and, in the second position, the ends of the first and second arms are positioned farther from each other than in the first position so as to release the first and second elements from therebetween.

13. The implant dispenser of claim 8, wherein the first arm includes a slot and the clip includes a main body and a projection extending from the main body, the projection being received by the slot of the first arm, and the main body being disposed between the first and second arms when engaged thereto.

14. The implant dispenser of claim 8, wherein the locking mechanism is selectively engageable to the first and second arms so as to allow the first and second arms to move to the second position when disengaged therefrom.

* * * * *